US012350325B2

(12) United States Patent
Muster et al.

(10) Patent No.: US 12,350,325 B2

(45) Date of Patent: Jul. 8, 2025

(54) RECOMBINANT HIGH GROWTH RATE INFLUENZA VIRUS COMPRISING MUTATIONS IN M1, NS2, AND PB2

(71) Applicants: BlueSky Immunotherapies GmbH, Vienna (AT); Vivaldi Biosciences Inc., Fort Collins, CO (US)

(72) Inventors: Thomas Muster, Vienna (AT); Amy Aspelund, Fort Collins, CO (US); Markus Wolschek, Vienna (AT)

(73) Assignees: VIVALDI BIOSCIENCES INC., Fort Collins, CO (US); BLUESKY IMMUNOTHERAPIES GMBH, Vienna (AU)

( * ) Notice: Subject to any disclaimer, the term of this patent is extended or adjusted under 35 U.S.C. 154(b) by 940 days.

(21) Appl. No.: 17/425,944

(22) PCT Filed: Jan. 24, 2020

(86) PCT No.: PCT/EP2020/051728

§ 371 (c)(1),
(2) Date: Jul. 26, 2021

(87) PCT Pub. No.: WO2020/152318

PCT Pub. Date: Jul. 30, 2020

(65) Prior Publication Data

US 2022/0160863 A1 May 26, 2022

Related U.S. Application Data

(60) Provisional application No. 62/796,544, filed on Jan. 24, 2019.

(30) Foreign Application Priority Data

Mar. 6, 2019 (EP) .................................... 19160992

(51) Int. Cl.
*A61K 39/12* (2006.01)
*C12N 7/00* (2006.01)

(52) U.S. Cl.
CPC ................ *A61K 39/12* (2013.01); *C12N 7/00* (2013.01); *C12N 2760/16221* (2013.01); *C12N 2760/16222* (2013.01); *C12N 2760/16234* (2013.01); *C12N 2760/16251* (2013.01)

(58) Field of Classification Search
CPC .......... A61K 39/12; C12N 2760/16221; C12N 2760/16222; C12N 2760/16234; C12N 2760/16251
See application file for complete search history.

(56) References Cited

FOREIGN PATENT DOCUMENTS

CN 101903043 A 1/2014

OTHER PUBLICATIONS

Ping, J., et al., Dec. 2016, Development of high-yield influenza B virus vaccine viruses, PNAS E8296-E8305.*
International Search Report and Written Opinion for Interntational Patent Application No. PCT/EP2020/051728 dated Aug. 6, 2020; 8 pages.
Alymova et al., "Immunogenicity and Protective Efficacy in Mice of Influenza B Virus Vaccines Grown in Mammalian Cells or Embryonated Chicken Eggs", Journal of Virology, May 1998, vol. 72, No. 5, pp. 4472-4477.
Couch, Robert B., "Advances in Influenza Virus Vaccine Research", Acad. Sci, vol. 685, 1993, pp. 803-812.
Dauber, Bianca. et al. "Double-Stranded RNA Binding of Influenza B Virus Nonstructural NS1 Protein Inhibits Protein Kinase R but Is Not Essential to Antagonize Production of Alpha/Beta Interferon", Journal of Virology, vol. 80, No. 23, Dec. 2006, pp. 11667-11677.
Ferko, Boris. et al. "Live Attenuated Influenza Virus Expressing Human Interleukin-2 Reveals Increased Immunogenic Potential in Young and Aged Hosts", Journal of Virology., vol. 80, No. 23, Dec. 2006, pp. 11621-11627.
Glezen, W. Paul et al. "Mortality and Influenza", The Journal of Infectious Diseases, vol. 146, No. 3, Sep. 1982, pp. 313-321.
Joyce MG et al. "Vaccine-Induced Antibodies that Neutralize Group 1 and 2 Influenza A Viruses", Cell, 2016, vol. 166, No. 3, Jul. 18, 2016, pp. 609-623.
Ping, Jihui et al. "Development of high-yield influenza A virus vaccine viruses", Nature Communications, 6:8148, 2015, 15 pgs.
Ping, Jihui et al. "Development of high-yield influenza B virus vaccine viruses", PNAS, 2016, vol. 113, No. 51, Dec. 5, 2016, pp. E8296-E8305.
Williams, Walter W. et al. "Immunization Policies and Vaccine Coverage Among Adults", Annals of Internal Medicine, 1988, vol. 108, pp. 616-625.
Zhang Yao, et al., The Effect of Influenza Type B Inter-lineage Reassortment on the Growth Characteristics of Influenza, Chinese Journal of Virology, vol. 32, No. 6, pp. 768-772 (2016).

* cited by examiner

*Primary Examiner* — Jeffrey S Parkin
(74) *Attorney, Agent, or Firm* — LOZA & LOZA, LLP; Michael Fedrick

(57) ABSTRACT

The present invention provides high growth influenza reassortant virus and high growth influenza reassortant virus vectors comprising amino acid modifications in the PB2, PB1, M1 and/or NS2 proteins which exhibit highly increased growth rates compared to unmodified influenza virus. Further provided are pharmaceutical compositions comprising reassortant virus and viral vectors comprising said modifications and their use for vaccination purposes.

14 Claims, 20 Drawing Sheets

Figure 1:
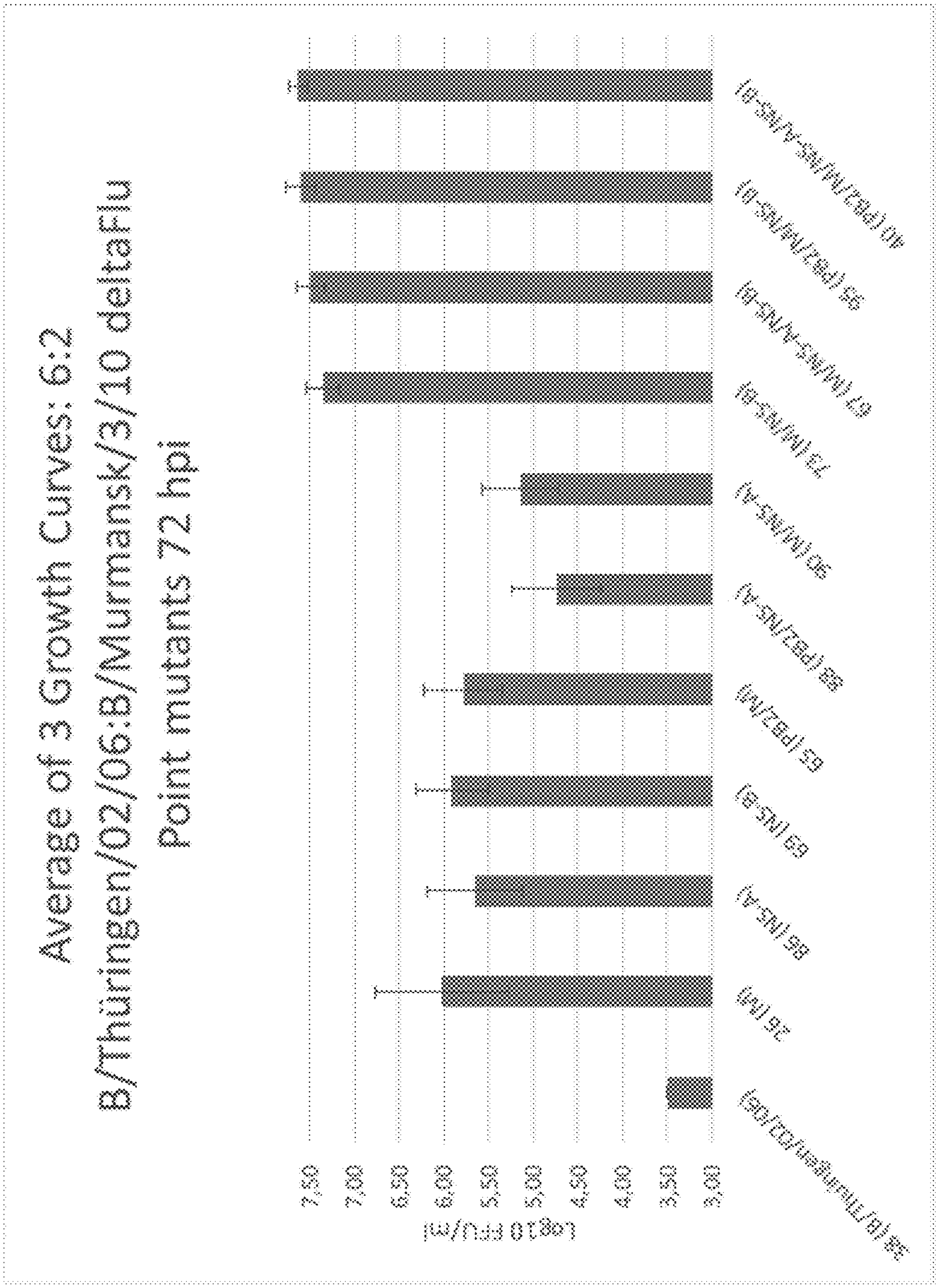

Specification includes a Sequence Listing.

Figure 4

B/Thüringen/02/06 PB2 wt

Nucleotide Sequence:

agcagaagcggagcgttttcaagATGACATTGGCTAAAATTGAATTGTTAAAACAACTGTTAAG
GGACAATGAAGCCAAAACAGTACTGAAACAAACAACAGTAGATCAATATAACATAAT
AAGAAAATTCAATACATCAAGAATTGAAAAGAACCCTTCATTAAGGATGAAGTGGGC
GATGTGTTCTAATTTTCCCTTGGCTTTGACCAAGGGTGACATGGCAAACAGAATCC
CCTTGGAATACAAGGGAATACAACTTAAAACAAATGCTGAAGACATAGGAACCAAA
GGCCAAATGTGCTCAATAGCAGCAGTTACCTGGTGGAATACATATGGACCAATAGG
GGATACTGAAGGTTTCGAAAAAGTCTACGAAAGCTTTTTTCTCAGAAAGATGAGACT
TGACAATGCCACTTGGGGCCGAATAACTTTTGGCCCAGTTGAAAGAGTAAGAAAAA
GGGTACTGCTAAACCCTCTCACCAAGGAAATGCCTCCAGATGAAGCAAGTAATGTG
ATAATGGAAATATTGTTCCCTAAAGAAGCAGGAATACCAAGAGAATCTACTTGGATA
CATAGGGAACTGATAAAAGAAAAAAGAGAAAAATTGAAAGGAACGATGATAACTCC
CATTGTACTGGCATACATGCTCGAGAGGGAATTAGTTGCCAGGAGAAGGTTCCTGC
CCGTGGCAGGAGCAACATCAGCTGAGTTCATAGAAATGCTACACTGCTTACAAGGT
GAAAATTGGAGGCAAATATATCACCCGGGAGGGAATAAACTAACTGAATCTAGGTC
CCAATCGATGATTGTGGCTTGTAGAAAGATAATCAGAAGATCAATAGTCGCATCAAA
CCCATTGGAGCTAGCTGTAGAAATTGCAAATAAGACTGTGATAGATACTGAACCTTT
AAAATCATGTCTGACAGCCATAGACGGAGGTGATGTCGCCTGTGACATAATAAGAG
CTGCATTAGGACTAAAGATCAGACAAAGACAAAGATTTGGACGACTTGAACTAAAG
AGAATATCAGGAAGAGGATTCAAAAATGATGAAGAAATATTAATCGGGAACGGAAC
AATACAGAAGATTGGAATATGGGACGGAGAAGAGGAGTTCCATGTGAGATGTGGT
GAATGCAGGGGAATATTAAAAAAGAGCAAAATGAGAATGGAAAAACTACTAATAAAT
TCAGCTAAAAAGGAGGACATGAAAGATTTAATAATCTTGTGCATGGTATTTTCCCAA
GACACTAGGATGTTCCAAGGAGTGAGGGGTGAAATAAATTTTCTTAATAGAGCAGG
CCAACTTTTATCTCCAATGTATCAACTCCAAAGATATTTTTTGAGTAGAAGTAACGAT
CTCTTTGATCAATGGGGGTATGAGGAATCACCCAAAGCAAGTGAGCTACATGGGAT
AAATGAACTAATGAATGCATCTGACTACACTTTGAAAGGGGTTGTAGTAACAAAAAA
TGTGATTGATGATTTTAGTTCTACTGAAACAGAAAAAGTATCTATAACAAAAAATCTT
AGTTTAATAAAAAGGACTGGGGAAGTCATAATGGGAGCCAATGACGTAAGTGAATT
AGAATCACAAGCACAGCTAATGATAACATATGATACACCAAAGATGTGGGAGATGG
GGACAACCAAAGAACTGGTGCAAAACACCTATCAATGGGTGCTGAAAAATTTGGTA
ACACTGAAGGCTCAGTTTCTTCTAGGGAAAGAAGACATGTTCCAATGGGATGCATT
TGAAGCATTTGAAAGCATAATCCCCCAGAAGATGGCTGGCCAATACAGTGGATTTG
CAAGAGCAGTGCTCAAACAAATGAGAGACCAAGAGGTCATGAAAACTGACCAGTTC
ATAAAGTTGTTGCCCTTTTGTTTCTCACCACCAAAGTTAAGGAGCAATGGGGAGCCT
TATCAGTTCTTGAGGCTTGTATTGAAGGGAGGAGGAGAAAATTTCATCGAAGTAAG
GAAAGGGTCTCCTCTATTCTCTTACAATCCACAAACAGAAGTCCTAACTATATGCGG
CAGAATGATGTCATTAAAAGGGAAAATTGAAGATGAAGAAAGGAATAGATCAATGG
GGAATGCAGTGTTGGCGGGTTTTCTTGTTAGTGGCAAGTATGACCCAGATCTTGGA
GATTTCAAAACCATTGAAGAACTTGAAAAGCTAAAACCAGGGGAGAAAGCAAACAT
CTTACTTTATCAAGGAAAGCCCGTTAAAGTAGTTAAAAGGAAAAGATATAGTGCTTT
ATCCAATGACATTTCACAAGGAATTAAGAGACAAAGAATGACAGTTGAGTCCATGG
GGTGGGCCTTGAGCTAAtataaatttatccattaattcaatgaatacaattgagtgaaaaatgctcgtgtttctact
(SEQ ID No. 1)

Figure 4 continued

B/Thüringen/02/06 PB2 wt

Amino Acid Sequence:

MTLAKIELLKQLLRDNEAKTVLKQTTVDQYNIIRKFNTSRIEKNPSLRMKWAMCSNFPLA
LTKGDMANRIPLEYKGIQLKTNAEDIGTKGQMCSIAAVTWWNTYGPIGDTEGFEKVYES
FFLRKMRLDNATWGRITFGPVERVRKRVLLNPLTKEMPPDEASNVIMEILFPKEAGIPRE
STWIHRELIKEKREKLKGTMITPIVLAYMLERELVARRRFLPVAGATSAEFIEMLHCLQG
ENWRQIYHPGGNKLTESRSQSMIVACRKIIRRSIVASNPLELAVEIANKTVIDTEPLKSCL
TAIDGGDVACDIIRAALGLKIRQRQRFGRLELKRISGRGFKNDEEILIGNGTIQKIGIWDG
EEEFHVRCGECRGILKKSKMRMEKLLINSAKKEDMKDLIILCMVFSQDTRMFQGVRGEI
NFLNRAGQLLSPMYQLQRYFLSRSNDLFDQWGYEESPKASELHGINELMNASDYTLK
GVVVTKNVIDDFSSTETEKVSITKNLSLIKRTGEVIMGANDVSELESQAQLMITYDTPKM
WEMGTTKELVQNTYQWVLKNLVTLKAQFLLGKEDMFQWDAFEAFESIIPQKMAGQYS
GFARAVLKQMRDQEVMKTDQFIKLLPFCFSPPKLRSNGEPYQFLRLVLKGGGENFIEV
RKGSPLFSYNPQTEVLTICGRMMSLKGKIEDEERNRSMGNAVLAGFLVSGKYDPDLGD
FKTIEELEKLKPGEKANILLYQGKPVKVVKRKRYSALSNDISQGIKRQRMTVESMGWAL
S (SEQ ID No. 2)

B/Thüringen/02/06 PB2 with g1302a mutation

Nucleotide Sequence:

agcagaagcggagcgttttcaagATGACATTGGCTAAAATTGAATTGTTAAAACAACTGTTAAG
GGACAATGAAGCCAAAACAGTACTGAAACAAACAACAGTAGATCAATATAACATAAT
AAGAAAATTCAATACATCAAGAATTGAAAAGAACCCTTCATTAAGGATGAAGTGGGC
GATGTGTTCTAATTTTCCCTTGGCTTTGACCAAGGGTGACATGGCAAACAGAATCC
CCTTGGAATACAAGGGAATACAACTTAAAACAAATGCTGAAGACATAGGAACCAAA
GGCCAAATGTGCTCAATAGCAGCAGTTACCTGGTGGAATACATATGGACCAATAGG
GGATACTGAAGGTTTCGAAAAAGTCTACGAAAGCTTTTTTCTCAGAAAGATGAGACT
TGACAATGCCACTTGGGGCCGAATAACTTTTGGCCCAGTTGAAAGAGTAAGAAAAA
GGGTACTGCTAAACCCTCTCACCAAGGAAATGCCTCCAGATGAAGCAAGTAATGTG
ATAATGGAAATATTGTTCCCTAAAGAAGCAGGAATACCAAGAGAATCTACTTGGATA
CATAGGGAACTGATAAAAGAAAAAAGAGAAAAATTGAAAGGAACGATGATAACTCC
CATTGTACTGGCATACATGCTCGAGAGGGAATTAGTTGCCAGGAGAAGGTTCCTGC
CCGTGGCAGGAGCAACATCAGCTGAGTTCATAGAAATGCTACACTGCTTACAAGGT
GAAAATTGGAGGCAAATATATCACCCGGGAGGGAATAAACTAACTGAATCTAGGTC
CCAATCGATGATTGTGGCTTGTAGAAAGATAATCAGAAGATCAATAGTCGCATCAAA
CCCATTGGAGCTAGCTGTAGAAATTGCAAATAAGACTGTGATAGATACTGAACCTTT
AAAATCATGTCTGACAGCCATAGACGGAGGTGATGTCGCCTGTGACATAATAAGAG
CTGCATTAGGACTAAAGATCAGACAAAGACAAAGATTTGGACGACTTGAACTAAAG
AGAATATCAGGAAGAGGATTCAAAAATGATGAAGAAATATTAATCGGGAACGGAAC
AATACAGAAGATTGGAATATGGGACGGAGAAGAGGAGTTCCATGTGAGATGTGGT
GAATGCAGGGGAATATTAAAAAAGAGCAAAATGAGAATGGAAAAACTACTAATAAAT
TCAGCTAAAAAGGAGGACATGAAAGATTTAATAATCTTGTGCATGGTATTTTCCCAA
GACACTAGGATGTTCCAAGGAGTGAGGGGTGAAATAAATTTTCTTAATAGAGCAaG
CCAACTTTTATCTCCAATGTATCAACTCCAAAGATATTTTTTGAGTAGAAGTAACGAT
CTCTTTGATCAATGGGGGTATGAGGAATCACCCAAAGCAAGTGAGCTACATGGGAT
AAATGAACTAATGAATGCATCTGACTACACTTTGAAAGGGGTTGTAGTAACAAAAAA
TGTGATTGATGATTTTAGTTCTACTGAAACAGAAAAAGTATCTATAACAAAAAATCTT
AGTTTAATAAAAAGGACTGGGGAAGTCATAATGGGAGCCAATGACGTAAGTGAATT Figure 4 continued
AGAATCACAAGCACAGCTAATGATAACATATGATACACCAAAGATGTGGGAGATGG
GGACAACCAAAGAACTGGTGCAAAACACCTATCAATGGGTGCTGAAAAATTTGGTA
ACACTGAAGGCTCAGTTTCTTCTAGGGAAAGAAGACATGTTCCAATGGGATGCATT
TGAAGCATTTGAAAGCATAATCCCCCAGAAGATGGCTGGCCAATACAGTGGATTTG
CAAGAGCAGTGCTCAAACAAATGAGAGACCAAGAGGTCATGAAAACTGACCAGTTC
ATAAAGTTGTTGCCCTTTTGTTTCTCACCACCAAAGTTAAGGAGCAATGGGGAGCCT
TATCAGTTCTTGAGGCTTGTATTGAAGGGAGGAGGAGAAAATTTCATCGAAGTAAG
GAAAGGGTCTCCTCTATTCTCTTACAATCCACAAACAGAAGTCCTAACTATATGCGG
CAGAATGATGTCATTAAAAGGGAAAATTGAAGATGAAGAAAGGAATAGATCAATGG
GGAATGCAGTGTTGGCGGGTTTTCTTGTTAGTGGCAAGTATGACCCAGATCTTGGA
GATTTCAAAACCATTGAAGAACTTGAAAAGCTAAAACCAGGGGAGAAAGCAAACAT
CTTACTTTATCAAGGAAAGCCCGTTAAAGTAGTTAAAAGGAAAAGATATAGTGCTTT
ATCCAATGACATTTCACAAGGAATTAAGAGACAAAGAATGACAGTTGAGTCCATGG
GGTGGGCCTTGAGCTAAtataaatttatccattaattcaatgaatacaattgagtgaaaaatgctcgtgtttctact
(SEQ ID No. 3)

Amino Acid Sequence G427S:
MTLAKIELLKQLLRDNEAKTVLKQTTVDQYNIIRKFNTSRIEKNPSLRMKWAMCSNFPLA
LTKGDMANRIPLEYKGIQLKTNAEDIGTKGQMCSIAAVTWWNTYGPIGDTEGFEKVYES
FFLRKMRLDNATWGRITFGPVERVRKRVLLNPLTKEMPPDEASNVIMEILFPKEAGIPRE
STWIHRELIKEKREKLKGTMITPIVLAYMLERELVARRRFLPVAGATSAEFIEMLHCLQG
ENWRQIYHPGGNKLTESRSQSMIVACRKIIRRSIVASNPLELAVEIANKTVIDTEPLKSCL
TAIDGGDVACDIIRAALGLKIRQRQRFGRLELKRISGRGFKNDEEILIGNGTIQKIGIWDG
EEEFHVRCGECRGILKKSKMRMEKLLINSAKKEDMKDLIILCMVFSQDTRMFQGVRGEI
NFLNRAsQLLSPMYQLQRYFLSRSNDLFDQWGYEESPKASELHGINELMNASDYTLKG
VVVTKNVIDDFSSTETEKVSITKNLSLIKRTGEVIMGANDVSELESQAQLMITYDTPKMW
EMGTTKELVQNTYQWVLKNLVTLKAQFLLGKEDMFQWDAFEAFESIIPQKMAGQYSGF
ARAVLKQMRDQEVMKTDQFIKLLPFCFSPPKLRSNGEPYQFLRLVLKGGGENFIEVRK
GSPLFSYNPQTEVLTICGRMMSLKGKIEDEERNRSMGNAVLAGFLVSGKYDPDLGDFK
TIEELEKLKPGEKANILLYQGKPVKVVKRKRYSALSNDISQGIKRQRMTVESMGWALS
(SEQ ID No. 4)

B/Thüringen/02/06 M1 wt
Nucleotide sequence
agcagaagcacgcactttcttaaaATGTCGCTGTTTGGAGACACAATTGCCTACCTGCTTTCAT
TGACAGAAGATGGAGAAGGCAAAGCAGAACTAGCAGAAAAATTACACTGTTGGTTC
GGTGGGAAAGAATTTGACCTAGACTCTGCCTTGGAATGGATAAAAAACAAAAGATG
CTTAACTGATATACAGAAAGCACTAATTGGTGCCTCTATCTGCTTTTTAAAACCCAAA
GACCAGGAAAGAAAAAGAAGATTCATCACAGAGCCCCTATCAGGAATGGGAACAAC
AGCAACAAAAAAGAAGGGCCTGATTCTAGCTGAGAGAAAAATGAGAAAATGTGTGA
GCTTCCATGAAGCATTTGAAATAGCAGAAGGCCATGAAAGCTCAGCGTTACTATATT
GTCTCATGGTCATGTACCTGAATCCTGGAAATTATTCAATGCAAGTAAAACTAGGAA
CGCTCTGTGCTTTGTGCGAAAAACAAGCATCACATTCACACAGGGCTCATAGCAGA
GCAGCGAGATCTTCAGTGCCCGGAGTGAGACGGGAAATGCAGATGGTCTCAGCTA
TGAACACAGCAAAAACAATGAATGGAATGGGAAAAGGAGAAGACGTCCAAAAACTG
GCAGAAGAACTGCAAAGCAACATTGGAGTATTGAGATCTCTTGGGGCAAGTCAAAA
GAATGGGGAAGGAATTGCAAAGGATGTAATGGAAGTGCTAAAGCAGAGCTCTATG Figure 4 continued
GGAAATTCAGCTCTTGTGAAGAAATACCTATAATGCTCGAACCATTTCAGATTCTTT
CAATTTGTTCTTTTATTTTATCAGCTCTCCATTTCATGGCTTGGACAATAGGACATTT
AAATCAAATAAAAAGAGGAGTAAACATGAAAATACGAATAAAGGGGCCAAATAAAGA
GACAATAAACAGAGAGGTATCAATTTTGAGACACAGTTACCAAAAAGAAATCCAGG
CTAAAGAAGCAATGAAGGAAGTACTCTCTGACAACATGGAGGTATTGAGTGACCAC
ATAGTAATTGAGGGGCTTTCTGCTGAAGAGATAATAAAAATGGGTGAAACAGTTTTG
GAGGTAGAAGAATTTCATTAAATTCAATTTTTACTGTACTTCTTACTATGCATTTAAG
CAAATTGTAATCAATGTCAGCAAATAAACTGGAAAAAGTGCGTTGTTTctact (SEQ ID No 5)

B/Thüringen/02/06 M wt
Amino acid sequence
MSLFGDTIAYLLSLTEDGEGKAELAEKLHCWFGGKEFDLDSALEWIKNKRCLTDIQKALI
GASICFLKPKDQERKRRFITEPLSGMGTTATKKKGLILAERKMRKCVSFHEAFEIAEGHE
SSALLYCLMVMYLNPGNYSMQVKLGTLCALCEKQASHSHRAHSRAARSSVPGVRREM
QMVSAMNTAKTMNGMGKGEDVQKLAEELQSNIGVLRSLGASQKNGEGIAKDVMEVLK
QSSMGNSALVKKYL (SEQ ID No. 6)

B/Thüringen/02/06 M with a289t mutations
Nucleotide sequence
agcagaagcacgcactttcttaaaATGTCGCTGTTTGGAGACACAATTGCCTACCTGCTTTCAT
TGACAGAAGATGGAGAAGGCAAAGCAGAACTAGCAGAAAAATTACACTGTTGGTTC
GGTGGGAAAGAATTTGACCTAGACTCTGCCTTGGAATGGATAAAAAACAAAAGATG
CTTAACTGATATACAGAAAGCACTAATTGGTGCCTCTATCTGCTTTTTAAAACCCAAA
GACCAGGAAAGAAAAAGAAGATTCATCACAGAGCCCCTATCAGGAATGGGAACAtC
AGCAACAAAAAAGAAGGGCCTGATTCTAGCTGAGAGAAAAATGAGAAAATGTGTGA
GCTTCCATGAAGCATTTGAAATAGCAGAAGGCCATGAAAGCTCAGCGTTACTATATT
GTCTCATGGTCATGTACCTGAATCCTGGAAATTATTCAATGCAAGTAAAACTAGGAA
CGCTCTGTGCTTTGTGCGAAAAACAAGCATCACATTCACACAGGGCTCATAGCAGA
GCAGCGAGATCTTCAGTGCCCGGAGTGAGACGGGAAATGCAGATGGTCTCAGCTA
TGAACACAGCAAAAACAATGAATGGAATGGGAAAAGGAGAAGACGTCCAAAAACTG
GCAGAAGAACTGCAAAGCAACATTGGAGTATTGAGATCTCTTGGGGCAAGTCAAAA
GAATGGGGAAGGAATTGCAAAGGATGTAATGGAAGTGCTAAAGCAGAGCTCTATG
GGAAATTCAGCTCTTGTGAAGAAATACCTATAATGCTCGAACCATTTCAGATTCTTT
CAATTTGTTCTTTTATTTTATCAGCTCTCCATTTCATGGCTTGGACAATAGGACATTT
AAATCAAATAAAAAGAGGAGTAAACATGAAAATACGAATAAAGGGGCCAAATAAAGA
GACAATAAACAGAGAGGTATCAATTTTGAGACACAGTTACCAAAAAGAAATCCAGG
CTAAAGAAGCAATGAAGGAAGTACTCTCTGACAACATGGAGGTATTGAGTGACCAC
ATAGTAATTGAGGGGCTTTCTGCTGAAGAGATAATAAAAATGGGTGAAACAGTTTTG
GAGGTAGAAGAATTTCATTAAATTCAATTTTTACTGTACTTCTTACTATGCATTTAAG
CAAATTGTAATCAATGTCAGCAAATAAACTGGAAAAAGTGCGTTGTTTctact (SEQ ID No. 7)

Figure 4 continued

B/Thüringen/02/06 M T89S

Amino acid sequence

MSLFGDTIAYLLSLTEDGEGKAELAEKLHCWFGGKEFDLDSALEWIKNKRCLTDIQKALI
GASICFLKPKDQERKRRFITEPLSGMGTsATKKKGLILAERKMRKCVSFHEAFEIAEGHE
SSALLYCLMVMYLNPGNYSMQVKLGTLCALCEKQASHSHRAHSRAARSSVPGVRREM
QMVSAMNTAKTMNGMGKGEDVQKLAEELQSNIGVLRSLGASQKNGEGIAKDVMEVLK
QSSMGNSALVKKYL (SEQ ID No. 8)

B/Thüringen/02/06 NS wt

Nucleotide sequence agcagaagcagaggatttgtttagtcactggcaaacaggaaaaATGGCGGACAATATGACCACAACAC
AAATTGAGTGGAGGATGAAGAAGATGGCCATCGGATCCTCAATTCACTCTTCGAGC
GTCTTAATGAAGGACATTCAAAGCCAATTCGAGCAGCTGAAACTGCGGTGGGAGTC
TTATCCCAATTTGGTCAAGAGCACCGATTATCACCAGAAGAGGGAGACAATTAGAC
TGGTCACGGAAGAACTTTATCTTTTAAGTAAAAGAATTGATGATAACATATTGTTCCA
CAAAACAGTAATAGCTAACAGCTCCATAATAGCTGACATGGTTGTATCATTATCATT
ATTAGAAACATTGTATGAAATGAAGGATGTGGTTGAAGTGTACAGCAGGCAGTGCT
TGTGAatttaaaataaaaatcctcttgttactact (SEQ ID No. 9)

B/Thüringen/02/06 NS wt

Amino acid sequence

MADNMTTTQIEWRMKKMAIGSSIHSSSVLMKDIQSQFEQLKLRWESYPNLVKSTDYHQ
KRETIRLVTEELYLLSKKIDDNILFHKTVIANSSIIADMVVSLSLLETLYEMKDVVEVYSRQ
CL (SEQ ID No. 10)

B/Thüringen/02/06 NS a267g, a269g mutations

Nucleotide Sequence:

agcagaagcagaggatttgtttagtcactggcaaacaggaaaaATGGCGGACAATATGACCACAACAC
AAATTGAGTGGAGGATGAAGAAGATGGCCATCGGATCCTCAATTCACTCTTCGAGC
GTCTTAATGAAGGACATTCAAAGCCAATTCGAGCAGCTGAAACTGCGGTGGGAGTC
TTATCCCAATTTGGTCAAGAGCACCGATTATCACCAGAAGAGGGAGACAATTAGAC
TGGTCACGGAAGAACTTTATCTTTTAAGTAgAgGAATTGATGATAACATATTGTTCCA
CAAAACAGTAATAGCTAACAGCTCCATAATAGCTGACATGGTTGTATCATTATCATT
ATTAGAAACATTGTATGAAATGAAGGATGTGGTTGAAGTGTACAGCAGGCAGTGCT
TGTGAatttaaaataaaaatcctcttgttactact (SEQ ID No. 11)

B/Thüringen/02/06 NS K75R R76G

Amino Acid Sequence NS2:

MADNMTTTQIEWRMKKMAIGSSIHSSSVLMKDIQSQFEQLKLRWESYPNLVKSTDYHQ
KRETIRLVTEELYLLSrgIDDNILFHKTVIANSSIIADMVVSLSLLETLYEMKDVVEVYSR
(SEQ ID No. 12)

Figure 4 continued

B/Thüringen/02/06 PB1 wt

Nucleotide Sequence:

agcagaagcggagcctttaagATGAATATAAATCCTTATTTTCTCTTCATAGATGTACCCATAC
AGGCAGCAATTTCAACAACATTCCCATACACCGGTGTTCCCCCTTATTCCCATGGAA
CGGGAACAGGCTACACAATAGACACCGTGATCAGAACACATGAGTACTCGAACAAA
GGAAAACAGTATGTTTCTGACATCACAGGATGTACAATGATA<u>G</u>ATCCAACAAATGG
GCCATTACCTGAAGACAATGAGCCAAGTGCCTATGCACAATTAGATTGCGTTCTGG
AGGCTTTGGATAGAATGGATGAGGAACATCCAGGTCTGTTTCAAGCAGCCTCACAG
AATGCCATGGAGGCACTAATGGTCACAACTGTAGACAAATTAACCCAGGGGAGACA
GACTTTCGATTGGACAGTATGCAGAAACCAGCCTGCTGCAACGGCACTAAACACAA
CAATAACCTCCTTCAGATTGAATGATTTGAATGGAGCTGACAAGGGTGGATTGGTA
CCCTTTTGCCAAGATATCATTGATTCATTAGACAAGCCTGAAATGACTTTCTTCTCA
GTAAAGAATATAAAGAAAAAATTGCCTGCTAAAAACAGAAAGGGTTTCCTCATAAAG
AGAATACCAATGAAAGTAAAAGACAGGATATCCAGAGTGGAATACATCAAAAGAGC
ATTGTCATTAAACACAATGACAAAAGATGCTGAAAGGGGCAAACTAAAAAGAAGAG
CGATTGCAACCGCTGGAATACAAATCAGAGGGTTTGTATTAGTAGTTGAAAACTTG
GCTAAAAACATCTGTGAAAATCTAGAACAAAGTGGTTTGCCCGTGGGTGGAAATGA
AAAGAAGGCCAAACTGTCAAATGCAGTGGCCAAAATGCTCAGTAACTGCCCACCAG
GAGGGATCAGCATGACAGTAACAGGAGACAATACTAAATGGAATGAATGCTTAAAT
CCACGAATCTTTTTGGCTATGACTGAAAGAATAACCAGAGACAGCCCAATTTGGTTC
CGGGATTTTTGTAGTATAGCACCGGTCTTGTTCTCCAACAAAATAGCCAGATTGGG
GAAAGGATTTATGATAACAAGTAAAACAAAAAGACTAAAGGCTCAAATACCTTGTCC
TGATCTGTTCAGCATACCATTAGAAAGATATAATGAAGAAACAAGGGCGAAATTAAA
AAGGCTGAAGCCATTCTTCAATGAAGAAGGAACGGCATCTTTGTCGCCTGGGATGA
TGATGGGAATGTTTAATATGCTATCTACCGTGTTGGGAGTAGCAGCACTAGGCATC
AAAAACATTGGAAACAAGGAATACTTATGGGATGGACTGCAATCTTCCGATGATTTT
GCTTTGTTTGTTAATGCAAAAGATGAAGAAACATGTATGGAAGGGATAAACGATTTT
TACCGAACATGTAAATTATTGGGAATAAACATGAGCAAAAAGAAAAGTTACTGTAAC
GAAACTGGAATGTTTGAATTTACAAGCATGTTCTATAGAGATGGATTTGTATCTAACT
TTGCAATGGAAATTCCTTCATTTGGAGTTGCTGGAGTAAATGAATCAGCAGATATGG
CAATAGGAATGACAATAATAAAGAACAATATGATTAACAATGGGATGGGTCCAGCAA
CAGCACAAACAGCCATACAATTGTTCATAGCTGATTATAGGTACACATACAAATGCC
ACAGAGGAGATTCCAAAGTGGAAGGAAAAAGAATGAAAATTATAAAGGAGCTATGG
GAAAACACTAAAGGAAGAGATGGTCTGTTAGTAGCAGATGGTGGGCCCAACATTTA
CAATTTGAGAAACTTACATATCCCAGAAATAGTATTGAAGTACAACCTAATGGACCC
TGAATACAAAGGGCGGTTACTTCACCCTCAAAATCCCTTTGTAGGACATTTGTCTAT
TGAAGGCATCAAAGAAGCAGATATAACCCCAGCACATGGTCCTGTGAGGAAAATGG
ATTATGATGCAGTGTCTGGAACTCATAGTTGGAGAACCAAAAGGAACAGATCTATAC
TAAATACTGATCAGAGGAACATGATTCTTGAAGAACAATGCTACGCTAAATGTTGCA
ATCTTTTTGAGGCCTGTTTTAACAGTGCATCATACAGGAAACCAGTAGGGCAGCATA
GCATGCTTGAGGCTATGGCCCATAGATTAAGAATGGATGCACGACTAGATTATGAA
TCAGGAAGAATGTCAAAGGATGATTTTGAGAAAGCAATGGCTCACCTTGGTGAGAT
TGGGTACACATAAGCTCCGAAGATGTCCATGGGGTTATTGGTCATCATTGGATACA
TGtgataaacaaatgattaaaatgaaaaaaggctcgtgtttctact (SEQ ID No. 13)

Figure 4 continued
B/Thüringen/02/06 PB1 wt
Amino acid Sequence:
MNINPYFLFIDVPIQAAISTTFPYTGVPPYSHGTGTGYTIDTVIRTHEYSNKGKQYVSDIT
GCTMIDPTNGPLPEDNEPSAYAQLDCVLEALDRMDEEHPGLFQAASQNAMEALMVTT
VDKLTQGRQTFDWTVCRNQPAATALNTTITSFRLNDLNGADKGGLVPFCQDIIDSLDKP
EMTFFSVKNIKKKLPAKNRKGFLIKRIPMKVKDRISRVEYIKRALSLNTMTKDAERGKLK
RRAIATAGIQIRGFVLVVENLAKNICENLEQSGLPVGGNEKKAKLSNAVAKMLSNCPPG
GISMTVTGDNTKWNECLNPRIFLAMTERITRDSPIWFRDFCSIAPVLFSNKIARLGKGFM
ITSKTKRLKAQIPCPDLFSIPLERYNEETRAKLKRLKPFFNEEGTASLSPGMMMGMFNM
LSTVLGVAALGIKNIGNKEYLWDGLQSSDDFALFVNAKDEETCMEGINDFYRTCKLLGIN
MSKKKSYCNETGMFEFTSMFYRDGFVSNFAMEIPSFGVAGVNESADMAIGMTIIKNNMI
NNGMGPATAQTAIQLFIADYRYTYKCHRGDSKVEGKRMKIIKELWENTKGRDGLLVAD
GGPNIYNLRNLHIPEIVLKYNLMDPEYKGRLLHPQNPFVGHLSIEGIKEADITPAHGPVRK
MDYDAVSGTHSWRTKRNRSILNTDQRNMILEEQCYAKCCNLFEACFNSASYRKPVGQ
HSMLEAMAHRLRMDARLDYESGRMSKDDFEKAMAHLGEIGYT (SEQ ID No. 14)

B/Thüringen/02/06 PB1 with g220a mutation
Nucleotide Sequence:
agcagaagcggagcctttaagATGAATATAAATCCTTATTTTCTCTTCATAGATGTACCCATAC
AGGCAGCAATTTCAACAACATTCCCATACACCGGTGTTCCCCCTTATTCCCATGGAA
CGGGAACAGGCTACACAATAGACACCGTGATCAGAACACATGAGTACTCGAACAAA
GGAAAACAGTATGTTTCTGACATCACAGGATGTACAATGATAaATCCAACAAATGGG
CCATTACCTGAAGACAATGAGCCAAGTGCCTATGCACAATTAGATTGCGTTCTGGA
GGCTTTGGATAGAATGGATGAGGAACATCCAGGTCTGTTTCAAGCAGCCTCACAGA
ATGCCATGGAGGCACTAATGGTCACAACTGTAGACAAATTAACCCAGGGGAGACAG
ACTTTCGATTGGACAGTATGCAGAAACCAGCCTGCTGCAACGGCACTAAACACAAC
AATAACCTCCTTCAGATTGAATGATTTGAATGGAGCTGACAAGGGTGGATTGGTAC
CCTTTTGCCAAGATATCATTGATTCATTAGACAAGCCTGAAATGACTTTCTTCTCAGT
AAAGAATATAAAGAAAAAATTGCCTGCTAAAAACAGAAAGGGTTTCCTCATAAAGAG
AATACCAATGAAAGTAAAAGACAGGATATCCAGAGTGGAATACATCAAAAGAGCATT
GTCATTAAACACAATGACAAAAGATGCTGAAAGGGGCAAACTAAAAAGAAGAGCGA
TTGCAACCGCTGGAATACAAATCAGAGGGTTTGTATTAGTAGTTGAAAACTTGGCTA
AAAACATCTGTGAAAATCTAGAACAAAGTGGTTTGCCCGTGGGTGGAAATGAAAAG
AAGGCCAAACTGTCAAATGCAGTGGCCAAAATGCTCAGTAACTGCCCACCAGGAG
GGATCAGCATGACAGTAACAGGAGACAATACTAAATGGAATGAATGCTTAAATCCA
CGAATCTTTTTGGCTATGACTGAAAGAATAACCAGAGACAGCCCAATTTGGTTCCG
GGATTTTTGTAGTATAGCACCGGTCTTGTTCTCCAACAAAATAGCCAGATTGGGGAA
AGGATTTATGATAACAAGTAAAACAAAAAGACTAAAGGCTCAAATACCTTGTCCTGA
TCTGTTCAGCATACCATTAGAAAGATATAATGAAGAAACAAGGGCGAAATTAAAAAG
GCTGAAGCCATTCTTCAATGAAGAAGGAACGGCATCTTTGTCGCCTGGGATGATGA
TGGGAATGTTTAATATGCTATCTACCGTGTTGGGAGTAGCAGCACTAGGCATCAAA
AACATTGGAAACAAGGAATACTTATGGGATGGACTGCAATCTTCCGATGATTTTGCT
TTGTTTGTTAATGCAAAAGATGAAGAAACATGTATGGAAGGGATAAACGATTTTTAC
CGAACATGTAAATTATTGGGAATAAACATGAGCAAAAAGAAAAGTTACTGTAACGAA
ACTGGAATGTTTGAATTTACAAGCATGTTCTATAGAGATGGATTTGTATCTAACTTTG
CAATGGAAATTCCTTCATTTGGAGTTGCTGGAGTAAATGAATCAGCAGATATGGCAA
TAGGAATGACAATAATAAAGAACAATATGATTAACAATGGGATGGGTCCAGCAACA Figure 4 continued
GCACAAACAGCCATACAATTGTTCATAGCTGATTATAGGTACACATACAAATGCCAC
AGAGGAGATTCCAAAGTGGAAGGAAAAAGAATGAAAATTATAAAGGAGCTATGGGA
AAACACTAAAGGAAGAGATGGTCTGTTAGTAGCAGATGGTGGGCCCAACATTTACA
ATTTGAGAAACTTACATATCCCAGAAATAGTATTGAAGTACAACCTAATGGACCCTG
AATACAAAGGGCGGTTACTTCACCCTCAAAATCCCTTTGTAGGACATTTGTCTATTG
AAGGCATCAAAGAAGCAGATATAACCCCAGCACATGGTCCTGTGAGGAAAATGGAT
TATGATGCAGTGTCTGGAACTCATAGTTGGAGAACCAAAAGGAACAGATCTATACTA
AATACTGATCAGAGGAACATGATTCTTGAAGAACAATGCTACGCTAAATGTTGCAAT
CTTTTTGAGGCCTGTTTTAACAGTGCATCATACAGGAAACCAGTAGGGCAGCATAG
CATGCTTGAGGCTATGGCCCATAGATTAAGAATGGATGCACGACTAGATTATGAAT
CAGGAAGAATGTCAAAGGATGATTTTGAGAAAGCAATGGCTCACCTTGGTGAGATT
GGGTACACATAAGCTCCGAAGATGTCCATGGGGTTATTGGTCATCATTGGATACAT
Gtgataaacaaatgattaaaatgaaaaaaggctcgtgtttctact (SEQ ID No. 15)

Amino Acid Sequence D67N:
MNINPYFLFIDVPIQAAISTTFPYTGVPPYSHGTGTGYTIDTVIRTHEYSNKGKQYVSDIT
GCTMI<u>n</u>PTNGPLPEDNEPSAYAQLDCVLEALDRMDEEHPGLFQAASQNAMEALMVTT
VDKLTQGRQTFDWTVCRNQPAATALNTTITSFRLNDLNGADKGGLVPFCQDIIDSLDKP
EMTFFSVKNIKKKLPAKNRKGFLIKRIPMKVKDRISRVEYIKRALSLNTMTKDAERGKLK
RRAIATAGIQIRGFVLVVENLAKNICENLEQSGLPVGGNEKKAKLSNAVAKMLSNCPPG
GISMTVTGDNTKWNECLNPRIFLAMTERITRDSPIWFRDFCSIAPVLFSNKIARLGKGFM
ITSKTKRLKAQIPCPDLFSIPLERYNEETRAKLKRLKPFFNEEGTASLSPGMMMGMFNM
LSTVLGVAALGIKNIGNKEYLWDGLQSSDDFALFVNAKDEETCMEGINDFYRTCKLLGIN
MSKKKSYCNETGMFEFTSMFYRDGFVSNFAMEIPSFGVAGVNESADMAIGMTIIKNNMI
NNGMGPATAQTAIQLFIADYRYTYKCHRGDSKVEGKRMKIIKELWENTKGRDGLLVAD
GGPNIYNLRNLHIPEIVLKYNLMDPEYKGRLLHPQNPFVGHLSIEGIKEADITPAHGPVRK
MDYDAVSGTHSWRTKRNRSILNTDQRNMILEEQCYAKCCNLFEACFNSASYRKPVGQ
HSMLEAMAHRLRMDARLDYESGRMSKDDFEKAMAHLGEIGYT (SEQ ID No. 16)

B/Thüringen/02/06 M1 a302g mutation
Nucleotide sequence
agcagaagcacgcactttcttaaaATGTCGCTGTTTGGAGACACAATTGCCTACCTGCTTTCAT
TGACAGAAGATGGAGAAGGCAAAGCAGAACTAGCAGAAAAATTACACTGTTGGTTC
GGTGGGAAAGAATTTGACCTAGACTCTGCCTTGGAATGGATAAAAAACAAAAGATG
CTTAACTGATATACAGAAAGCACTAATTGGTGCCTCTATCTGCTTTTTAAAACCCAAA
GACCAGGAAAGAAAAAGAAGATTCATCACAGAGCCCCTATCAGGAATGGGAACAAC
AGCAACAAAAA<u>g</u>GAAGGGCCTGATTCTAGCTGAGAGAAAAATGAGAAAATGTGTGA
GCTTCCATGAAGCATTTGAAATAGCAGAAGGCCATGAAAGCTCAGCGTTACTATATT
GTCTCATGGTCATGTACCTGAATCCTGGAAATTATTCAATGCAAGTAAAACTAGGAA
CGCTCTGTGCTTTGTGCGAAAAACAAGCATCACATTCACACAGGGCTCATAGCAGA
GCAGCGAGATCTTCAGTGCCCGGAGTGAGACGGGAAATGCAGATGGTCTCAGCTA
TGAACACAGCAAAAACAATGAATGGAATGGGAAAAGGAGAAGACGTCCAAAAACTG
GCAGAAGAACTGCAAAGCAACATTGGAGTATTGAGATCTCTTGGGGCAAGTCAAAA
GAATGGGGAAGGAATTGCAAAGGATGTAATGGAAGTGCTAAAGCAGAGCTCTATG
GGAAATTCAGCTCTTGTGAAGAAATACCTATAATGCTCGAACCATTTCAGATTCTTT
CAATTTGTTCTTTTATTTTATCAGCTCTCCATTTCATGGCTTGGACAATAGGACATTT
AAATCAAATAAAAAGAGGAGTAAACATGAAAATACGAATAAAGGGGCCAAATAAAGA Figure 4 continued
GACAATAAACAGAGAGGTATCAATTTTGAGACACAGTTACCAAAAAGAAATCCAGG
CTAAAGAAGCAATGAAGGAAGTACTCTCTGACAACATGGAGGTATTGAGTGACCAC
ATAGTAATTGAGGGGCTTTCTGCTGAAGAGATAATAAAAATGGGTGAAACAGTTTTG
GAGGTAGAAGAATTTCATTAAATTCAATTTTTACTGTACTTCTTACTATGCATTTAAG
CAAATTGTAATCAATGTCAGCAAATAAACTGGAAAAAGTGCGTTGTTTctact (SEQ ID No. 19)

B/Thüringen/02/06 M1 K93R
Amino acid sequence
MSLFGDTIAYLLSLTEDGEGKAELAEKLHCWFGGKEFDLDSALEWIKNKRCLTDIQKALI
GASICFLKPKDQERKRRFITEPLSGMGTTATKrKGLILAERKMRKCVSFHEAFEIAEGHE
SSALLYCLMVMYLNPGNYSMQVKLGTLCALCEKQASHSHRAHSRAARSSVPGVRREM
QMVSAMNTAKTMNGMGKGEDVQKLAEELQSNIGVLRSLGASQKNGEGIAKDVMEVLK
QSSMGNSALVKKYL (SEQ ID No. 20)

B/Thüringen/02/06 BGHB ΔNS with t392c mutations
Nucleotide Sequence:
agcagaagcagaggatttgtttagtcactggcaaacaggaaaaATGGCGGACAATATGACCACAACAC
AAATTGAGTGGAGGATGAAGAAGATGGCCATCGGATCCTCAATTCACTCTTCGAGC
GTCTTAATGAAGGACATTCAAAGCCAATTCGAGCAGCTGAAACTGCGGTGGGAGTC
TTATCCCAATTTGGTCAAGAGCACCGATTATCACCAGAAGAGGGAGACAATTAGAC
TGGTCACGGAAGAACTTTATCTTTTAAGTAAAAGAATTGATGATAACATATTGTTCCA
CAAAACAGTAATAGCTAACAGCTCCATAATAGCTGACATGGTTGTATCATTATCATT
ATTAGAAACATTGTATGAAATGAAGGATGTGGTTGAAGTGcACAGCAGGCAGTGCT
TGTGAatttaaaataaaaatcctcttgttactact (SEQ ID No. 23)

B/Thüringen/02/06 BGHB ΔNS
Amino Acid Sequence NS2 Y117H
MADNMTTTQIEWRMKKMAIGSSIHSSSVLMKDIQSQFEQLKLRWESYPNLVKSTDYHQ
KRETIRLVTEELYLLSKRIDDNILFHKTVIANSSIIADMVVSLSLLETLYEMKDVVEVhSR
(SEQ ID No. 24)

IVR-116 PB2 wt
Nucleotide sequence
agcgaaagcaggtcaattatattcaatATGGAAAGAATAAAAGAACTACGAAATCTAATGTCGCA
GTCTCGCACCCGCGAGATACTCACAAAAACCACCGTGGACCATATGGCCATAATCA
AGAAGTACACATCAGGAAGACAGGAGAAGAACCCAGCACTTAGGATGAAATGGAT
GATGGCAATGAAATATCCAATTACAGCAGACAAGAGGATAACGGAAATGATTCCTG
AGAGAAATGAGCAAGGACAAACTTTATGGAGTAAAATGAATGATTCCGGATCAGAC
CGAGTGATGGTATCACCTCTGGCTGTGACATGGTGGAATAGGAATGGACCAATAAC
AAATACAGTTCATTATCCAAAAATCTACAAAACTTATTTTGAAAGAGTCGAAAGGCTA
AAGCATGGAACCTTTGGCCCTGTCCATTTTAGAAACCAAGTCAAAATACGTCGGAG
AGTTGACATAAATCCTGGTCATGCAGATCTCAGTGCCAAGGAGGCACAGGATGTAA
TCATGGAAGTTGTTTTCCCTAACGAAGTGGGAGCCAGGATACTAACATCGGAATCG
CAACTAACGATAACCAAAGAGAAGAAAGAAGAACTCCAGGATTGCAAAATTTCTCCT
TTGATGGTTGCATACATGTTGGAGAGAGAACTGGTCCGCAAAACGAGATTCCTCCC
AGTGGCTGGTGGAACAAGCAGTGTGTACATTGAAGTGTTGCATTTGACTCAAGGAA Figure 4 continued
CATGCTGGGAACAGATGTATACTCCAGGAGGGGAAGTGAGGAATGATGATGTTGAT
CAAAGCTTGATTATTGCTGCTAGGAACATAGTGAGAAGAGCTGCAGTATCAGCAGA
TCCACTAGCATCTTTATTGGAGATGTGCCACAGCACACAGATTGGTGGAATTAGGA
TGGTAGACATCCTTAGGCAGAACCCAACAGAAGAGCAAGCCGTGGATATATGCAAG
GCTGCAATGGGACTGAGAATTAGCTCATCCTTCAGTTTTGGTGGATTCACATTTAAG
AGAACAAGCGGATCATCAGTCAAGAGAGAGGAAGAGGTGCTTACGGGCAATCTTC
AAACATTGAAGATAAGAGTGCATGAGGGATATGAAGAGTTCACAATGGTTGGGAGA
AGAGCAACAGCCATACTCAGAAAAGCAACCAGGAGATTGATTCAGCTGATAGTGAG
TGGGAGAGACGAACAGTCGATTGCCGAAGCAATAATTGTGGCCATGGTATTTTCAC
AAGAGGATTGTATGATAAAAGCAGTCAGAGGTGATCTGAATTTCGTCAATAGGGCA
AATCAACGATTGAATCCTATGCATCAACTTTTAAGACATTTTCAGAAGGATGCGAAA
GTGCTTTTTCAAAATTGGGGAGTTGAACCTATCGACAATGTGATGGGAATGATTGG
GATATTGCCCGACATGACTCCAAGCATCGAGATGTCAATGAGAGGAGTGAGAATCA
GCAAAATGGGTGTAGATGAGTACTCCAGCACGGAGAGGGTAGTGGTGAGCATTGA
CCGTTTTTTGAGAATCCGGGACCAACGAGGAAATGTACTACTGTCTCCCGAGGAGG
TCAGTGAAACACAGGGAACAGAGAAACTGACAATAACTTACTCATCGTCAATGATGT
GGGAGATTAATGGTCCTGAATCAGTGTTGGTCAATACCTATCAATGGATCATCAGAA
ACTGGGAAACTGTTAAAATTCAGTGGTCCCAGAACCCTACAATGCTATACAATAAAA
TGGAATTTGAACCATTTCAGTCTTTAGTACCTAAGGCCATTAGAGGCCAATACAGTG
GGTTTGTAAGAACTCTGTTCCAACAAATGAGGGATGTGCTTGGGACATTTGATACC
GCACAGATAATAAAACTTCTTCCCTTCGCAGCCGCTCCACCAAAGCAAAGTAGAAT
GCAGTTCTCCTCATTTACTGTGAATGTGAGGGGATCAGGAATGAGAATACTTGTAA
GGGGCAATTCTCCTGTATTCAACTATAACAAGGCCACGAAGAGACTCACAGTTCTC
GGAAAGGATGCTGGCACTTTAACTGAAGACCCAGATGAAGGCACAGCTGGAGTGG
AGTCCGCTGTTCTGAGGGGATTCCTCATTCTGGGCAAAGAAGACAAGAGATATGGG
CCAGCACTAAGCATCAATGAACTGAGCAACCTTGCGAAAGGAGAGAAGGCTAATGT
GCTAATTGGGCAAGGAGACGTGGTGTTGGTAATGAAACGGAAACGGACTCTAGC
ATACTTACTGACAGCCAGACAGCGACCAAAAGAATTCGGATGGCCATCAATTAGtgtc
gaatagtttaaaaacgaccttgtttctact (SEQ ID No. 25)

IVR-116 PB2 wt
Amino Acid Sequence
MERIKELRNLMSQSRTREILTKTTVDHMAIIKKYTSGRQEKNPALRMKWMMAMKYPITA
DKRITEMIPERNEQGQTLWSKMNDSGSDRVMVSPLAVTWWNRNGPITNTVHYPKIYKT
YFERVERLKHGTFGPVHFRNQVKIRRRVDINPGHADLSAKEAQDVIMEVVFPNEVGARI
LTSESQLTITKEKKEELQDCKISPLMVAYMLERELVRKTRFLPVAGGTSSVYIEVLHLTQ
GTCWEQMYTPGGEVRNDDVDQSLIIAARNIVRRAAVSADPLASLLEMCHSTQIGGIRM
VDILRQNPTEEQAVDICKAAMGLRISSSFSFGGFTFKRTSGSSVKREEEVLTGNLQTLKI
RVHEGYEEFTMVGRRATAILRKATRRLIQLIVSGRDEQSIAEAIIVAMVFSQEDCMIKAVR
GDLNFVNRANQRLNPMHQLLRHFQKDAKVLFQNWGVEPIDNVMGMIGILPDMTPSIEM
SMRGVRISKMGVDEYSSTERVVVSIDRFLRIRDQRGNVLLSPEEVSETQGTEKLTITYS
SSMMWEINGPESVLVNTYQWIIRNWETVKIQWSQNPTMLYNKMEFEPFQSLVPKAIRG
QYSGFVRTLFQQMRDVLGTFDTAQIIKLLPFAAAPPKQSRMQFSSFTVNVRGSGMRILV
RGNSPVFNYNKATKRLTVLGKDAGTLTEDPDEGTAGVESAVLRGFLILGKEDKRYGPA
LSINELSNLAKGEKANVLIGQGDVVLVMKRKRDSSILTDSQTATKRIRMAIN (SEQ ID No
26)

Figure 4 continued

IVR-116 delNS PB2 a266g

Nucleotide Sequence:

agcgaaagcaggtcaattatattcaatATGGAAAGAATAAAAGAACTACGAAATCTAATGTCGCA
GTCTCGCACCCGCGAGATACTCACAAAAACCACCGTGGACCATATGGCCATAATCA
AGAAGTACACATCAGGAAGACAGGAGAAGAACCCAGCACTTAGGATGAAATGGAT
GATGGCAATGAAATATCCAATTACAGCAGACAAGAGGATAACGGAAATGATTCCTG
AGAGAAATGAGCAAGGACAAACTTTATGGAGTAgAATGAATGATTCCGGATCAGAC
CGAGTGATGGTATCACCTCTGGCTGTGACATGGTGGAATAGGAATGGACCAATAAC
AAATACAGTTCATTATCCAAAAATCTACAAAACTTATTTTGAAAGAGTCGAAAGGCTA
AAGCATGGAACCTTTGGCCCTGTCCATTTTAGAAACCAAGTCAAAATACGTCGGAG
AGTTGACATAAATCCTGGTCATGCAGATCTCAGTGCCAAGGAGGCACAGGATGTAA
TCATGGAAGTTGTTTTCCCTAACGAAGTGGGAGCCAGGATACTAACATCGGAATCG
CAACTAACGATAACCAAAGAGAAGAAAGAAGAACTCCAGGATTGCAAAATTTCTCCT
TTGATGGTTGCATACATGTTGGAGAGAGAACTGGTCCGCAAAACGAGATTCCTCCC
AGTGGCTGGTGGAACAAGCAGTGTGTACATTGAAGTGTTGCATTTGACTCAAGGAA
CATGCTGGGAACAGATGTATACTCCAGGAGGGGAAGTGAGGAATGATGATGTTGAT
CAAAGCTTGATTATTGCTGCTAGGAACATAGTGAGAAGAGCTGCAGTATCAGCAGA
TCCACTAGCATCTTTATTGGAGATGTGCCACAGCACACAGATTGGTGGAATTAGGA
TGGTAGACATCCTTAGGCAGAACCCAACAGAAGAGCAAGCCGTGGATATATGCAAG
GCTGCAATGGGACTGAGAATTAGCTCATCCTTCAGTTTTGGTGGATTCACATTTAAG
AGAACAAGCGGATCATCAGTCAAGAGAGAGGAAGAGGTGCTTACGGGCAATCTTC
AAACATTGAAGATAAGAGTGCATGAGGGATATGAAGAGTTCACAATGGTTGGGAGA
AGAGCAACAGCCATACTCAGAAAAGCAACCAGGAGATTGATTCAGCTGATAGTGAG
TGGGAGAGACGAACAGTCGATTGCCGAAGCAATAATTGTGGCCATGGTATTTTCAC
AAGAGGATTGTATGATAAAAGCAGTCAGAGGTGATCTGAATTTCGTCAATAGGGCA
AATCAACGATTGAATCCTATGCATCAACTTTTAAGACATTTTCAGAAGGATGCGAAA
GTGCTTTTTCAAAATTGGGGAGTTGAACCTATCGACAATGTGATGGGAATGATTGG
GATATTGCCCGACATGACTCCAAGCATCGAGATGTCAATGAGAGGAGTGAGAATCA
GCAAAATGGGTGTAGATGAGTACTCCAGCACGGAGAGGGTAGTGGTGAGCATTGA
CCGTTTTTTGAGAATCCGGGACCAACGAGGAAATGTACTACTGTCTCCCGAGGAGG
TCAGTGAAACACAGGGAACAGAGAAACTGACAATAACTTACTCATCGTCAATGATGT
GGGAGATTAATGGTCCTGAATCAGTGTTGGTCAATACCTATCAATGGATCATCAGAA
ACTGGGAAACTGTTAAAATTCAGTGGTCCCAGAACCCTACAATGCTATACAATAAAA
TGGAATTTGAACCATTTCAGTCTTTAGTACCTAAGGCCATTAGAGGCCAATACAGTG
GGTTTGTAAGAACTCTGTTCCAACAAATGAGGGATGTGCTTGGGACATTTGATACC
GCACAGATAATAAAACTTCTTCCCTTCGCAGCCGCTCCACCAAAGCAAAGTAGAAT
GCAGTTCTCCTCATTTACTGTGAATGTGAGGGGATCAGGAATGAGAATACTTGTAA
GGGGCAATTCTCCTGTATTCAACTATAACAAGGCCACGAAGAGACTCACAGTTCTC
GGAAAGGATGCTGGCACTTTAACTGAAGACCCAGATGAAGGCACAGCTGGAGTGG
AGTCCGCTGTTCTGAGGGGATTCCTCATTCTGGGCAAAGAAGACAAGAGATATGGG
CCAGCACTAAGCATCAATGAACTGAGCAACCTTGCGAAAGGAGAGAAGGCTAATGT
GCTAATTGGGCAAGGAGACGTGGTGTTGGTAATGAAACGGAAACGGGACTCTAGC
ATACTTACTGACAGCCAGACAGCGACCAAAAGAATTCGGATGGCCATCAATTAGtgtc
gaatagtttaaaaacgaccttgtttctact (SEQ ID No. 27)

Figure 4 continued
IVR-116 delNS PB2
Amino Acid Sequence K80R:
MERIKELRNLMSQSRTREILTKTTVDHMAIIKKYTSGRQEKNPALRMKWMMAMKYPITA
DKRITEMIPERNEQGQTLWSrMNDSGSDRVMVSPLAVTWWNRNGPITNTVHYPKIYKT
YFERVERLKHGTFGPVHFRNQVKIRRRVDINPGHADLSAKEAQDVIMEVVFPNEVGARI
LTSESQLTITKEKKEELQDCKISPLMVAYMLERELVRKTRFLPVAGGTSSVYIEVLHLTQ
GTCWEQMYTPGGEVRNDDVDQSLIIAARNIVRRAAVSADPLASLLEMCHSTQIGGIRM
VDILRQNPTEEQAVDICKAAMGLRISSSFSFGGFTFKRTSGSSVKREEEVLTGNLQTLKI
RVHEGYEEFTMVGRRATAILRKATRRLIQLIVSGRDEQSIAEAIIVAMVFSQEDCMIKAVR
GDLNFVNRANQRLNPMHQLLRHFQKDAKVLFQNWGVEPIDNVMGMIGILPDMTPSIEM
SMRGVRISKMGVDEYSSTERVVVSIDRFLRIRDQRGNVLLSPEEVSETQGTEKLTITYS
SSMMWEINGPESVLVNTYQWIIRNWETVKIQWSQNPTMLYNKMEFEPFQSLVPKAIRG
QYSGFVRTLFQQMRDVLGTFDTAQIIKLLPFAAAPPKQSRMQFSSFTVNVRGSGMRILV
RGNSPVFNYNKATKRLTVLGKDAGTLTEDPDEGTAGVESAVLRGFLILGKEDKRYGPA
LSINELSNLAKGEKANVLIGQGDVVLVMKRKRDSSILTDSQTATKRIRMAIN (SEQ ID No 28)

IVR-116 delNS PB1 wt

Nucleotide Sequence:

agcgaaagcaggcaaaccatttgaatggATGTCAATCCGACTTTACTTTTCTTGAAAATTCCAGC
GCAAAATGCCATAAGCACCACATTCCCTTATACTGGAGATCCTCCATACAGCCATG
GAACAGGAACAGGATACACCATGGACACAGTTAACAGAACACATCAATATTCAGAA
AAAGGGAAATGGACAACAAACACAGAAACTGGGGCGCCCCAACTTAACCCGATTG
ATGGACCACTACCTGAGGATAATGAGCCAAGTGGATATGCACAAACAGACTGTGTC
CTGGAAGCTATGGCTTTCCTTGAGGAATCCCACCCAGGGATCTTTGAAAACTCGTG
CCTTGAAACAATGGAAGTCGTTCAACAAACAAGAGTGGACAGACTGACCCAAGGTC
GTCAGACCTATGATTGGACATTAAACAGAAATCAACCAGCCGCAACTGCATTAGCC
AACACTATAGAAGTTTTCAGATCGAATGGTCTAACAGCTAATGAGTCGGGAAGGCT
AATAGATTTCCTCAAGGATGTGATGGAATCAATGGATAAAGAGGAAATAGAGATAAC
AACACACTTCCAAAGAAAAAGAAGAGTAAGAGACAACATGACCAAGAAAATGGTCA
CACAAAGAACAATAGGAAAGAAAAAGCAGAGAGTGAACAAGAGAAGCTATCTAATA
AGAGCATTAACTTTGAACACAATGACCAAAGATGCAGAAAGAGGTAAATTAAAGAGA
AGAGCTATTGCAACACCCGGGATGCAAATCAGAGGGTTCGTGTACTTTGTTGAAAC
TCTAGCTAGGAGCATTTGTGAGAAGCTTGAACAGTCTGGACTTCCAGTAGGAGGTA
ATGAAAAGAAGGCCAAACTGGCAAATGTTGTGAGAAAGATGATGACTAATTCACAA
GACACAGAGCTTTCTTTCACAATTACTGGAGACAATACTAAGTGGAATGAAAATCAA
AATCCTCGAATGTTCCTGGCGATGATTACATATATCACAAAAAATCAACCTGAATGG
TTCAGAAACATCCTGAGCATCGCACCCATAATGTTCTCAAACAAAATGGCGAGACTA
GGGAAAGGATACATGTTCGAAAGTAAGAGAATGAAGCTCCGAACACAAATACCAGC
AGAAATGCTAGCAAGCATTGACCTAAAGTATTTCAATGAATCAACAAGAAAGAAAAT
TGAGAAAATAAGGCCTCTTCTAATAGATGGCACAGCGTCATTGAGCCCTGGAATGA
TGATGGGCATGTTCAACATGCTAAGTACGGTTTTAGGAGTCTCAATACTGAATCTTG
GGCAAAAGAAATACACCAAAACAACATACTGGTGGGATGGGCTTCAATCCTCTGAT
GATTTTGCTCTCATAGTGAATGCACCAAATCATGAGGGAATACAAGCAGGAGTGGA
TAGATTCTACAGAACCTGCAAGCTAGTCGGAATCAATATGAGCAAGAAGAAGTCCT
ATATAAATAGGACAGGAACATTTGAATTCACAAGCTTTTTTTATCGCTATGGATTTGT
GGCCAATTTTAGCATGGAGCTGCCCAGTTTTGGAGTGTCTGGGATTAATGAATCAG

Figure 4 continued

CTGATATGAGCATTGGAGTAACAGTGATAAAGAACAACATGATAAACAATGACCTTG
GACCAGCAACAGCCCAGATGGCTCTTCAACTGTTCATCAAGGACTACAGATATACA
TATCGGTGCCACAGAGGAGACACACAAATTCAGACGAGGAGATCATTTGAGCTAAA
GAAGCTGTGGGAGCAAACCCGATCAAAGGCAGGACTATTGGTTTCAGATGGAGGA
CCGAACTTATACAATATCCGGAATCTTCACATCCCTGAAGTCTGCTTAAAGTGGGAG
CTAATGGATGAAGACTATCAGGGAAGACTTTGTAATCCCCTGAATCCATTTGTCAGC
CATAAAGAGATTGAGTCTGTAAACAATGCTGTGGTAATGCCAGCTCATGGTCCAGC
CAAGAGCATGGAATATGACGCTGTTGCAACTACACACTCCTGGATTCCCAAGAGGA
ACCGCTCTATTCTCAACACAA<u>G</u>CCAAAGGGGAATTCTTGAGGATGAACAGATGTAT
CAGAAGTGCTGCAACCTGTTCGAGAAATTTTTCCCCAGTAGTTCATACAGGAGACC
GGTTGGAATTTCCAGCATGGTGGAGGCCATGGTGTCTAGGGCCCGGATTGATGCC
AGAATTGACTTCGAGTCTGGACGGATTAAGAAAGAAGAGTTCTCCGAGATCATGAA
GATCTGTTCCACCATTGAAGAGCTCAGACGGCAAAAACAATGAatttagcttgtccttcatgaa
aaaatgccttgtttctact (SEQ ID No. 29)

IVR-116 delNS PB1 wt
Amino acid sequence

MDVNPTLLFLKIPAQNAISTTFPYTGDPPYSHGTGTGYTMDTVNRTHQYSEKGKWTTN
TETGAPQLNPIDGPLPEDNEPSGYAQTDCVLEAMAFLEGSHPGIFENSCLETMEVVQQ
TRVDRLTQGRQTYDWTLNRNQPAATALANTIEVFRSNGLTANESGRLIDFLKDVMESM
DKEEIEITTHFQRKRRVRDNMTKKMVTQRTIGKKKQRVNKRSYLIRALTLNTMTKDAER
GKLKRRAIATPGMQIRGFVYFVETLARSICEKLEQSGLPVGGNEKKAKLANVVRKMMT
NSQDTELSFTITGDNTKWNENQNPRMFLAMITYITKNQPEWFRNILSIAPIMFSNKMARL
GKGYMFESKRMKLRTQIPAEMLASIDLKYFNESTRKKIEKIRPLLIDGTASLSPGMMMG
MFNMLSTVLGVSILNLGQKKYTKTTYWWDGLQSSDDFALIVNAPNHEGIQAGVDRFYR
TCKLVGINMSKKKSYINRTGTFEFTSFFYRYGFVANFSMELPSFGVSGINESADMSIGVT
VIKNNMINNDLGPATAQMALQLFIKDYRYTYRCHRGDTQIQTRRSFELKKLWEQTRSKA
GLLVSDGGPNLYNIRNLHIPEVCLKWELMDEDYQGRLCNPLNPFVSHKEIESVNNAVV
MPAHGPAKSMEYDAVATTHSWIPKRNRSILNTSQRGILEDEQMYQKCCNLFEKFFPSS
SYRRPVGISSMVEAMVSRARIDARIDFESGRIKKEEFSEIMKICSTIEELRRQKQ (SEQ ID
No. 30)

IVR-116 delNS PB1 a314g and g2057a
Nucleotide Sequence agcgaaagcaggcaaaccatttgaatggATGTCAATCCGACTTTACTTTTCTTGAAAATTCCAGC
GCAAAATGCCATAAGCACCACATTCCCTTATACTGGAGATCCTCCATACAGCCATG
GAACAGGAACAGGATACACCATGGACACAGTTAACAGAACACATCAATATTCAGAA
AAAGGGAAATGGACAACAAACACAGAAACTGGGGCGCCCCAACTTAACCCGATTG
ATGGACCACTACCTGAGGATAATGAGCCAAGTGGATATGCACAAACAGACTGTGTC
CTGGAAGCTATGGCTTTCCTTGAGG<u>g</u>ATCCCACCCAGGGATCTTTGAAAACTCGTG
CCTTGAAACAATGGAAGTCGTTCAACAAACAAGAGTGGACAGACTGACCCAAGGTC
GTCAGACCTATGATTGGACATTAAACAGAAATCAACCAGCCGCAACTGCATTAGCC
AACACTATAGAAGTTTTCAGATCGAATGGTCTAACAGCTAATGAGTCGGGAAGGCT
AATAGATTTCCTCAAGGATGTGATGGAATCAATGGATAAAGAGGAAATAGAGATAAC
AACACACTTCCAAAGAAAAAGAAGAGTAAGAGACAACATGACCAAGAAAATGGTCA Figure 4 continued
CACAAAGAACAATAGGAAAGAAAAAGCAGAGAGTGAACAAGAGAAGCTATCTAATA
AGAGCATTAACTTTGAACACAATGACCAAAGATGCAGAAAGAGGTAAATTAAAGAGA
AGAGCTATTGCAACACCCGGGATGCAAATCAGAGGGTTCGTGTACTTTGTTGAAAC
TCTAGCTAGGAGCATTTGTGAGAAGCTTGAACAGTCTGGACTTCCAGTAGGAGGTA
ATGAAAAGAAGGCCAAACTGGCAAATGTTGTGAGAAAGATGATGACTAATTCACAA
GACACAGAGCTTTCTTTCACAATTACTGGAGACAATACTAAGTGGAATGAAAATCAA
AATCCTCGAATGTTCCTGGCGATGATTACATATATCACAAAAAATCAACCTGAATGG
TTCAGAAACATCCTGAGCATCGCACCCATAATGTTCTCAAACAAAATGGCGAGACTA
GGGAAAGGATACATGTTCGAAAGTAAGAGAATGAAGCTCCGAACACAAATACCAGC
AGAAATGCTAGCAAGCATTGACCTAAAGTATTTCAATGAATCAACAAGAAAGAAAAT
TGAGAAAATAAGGCCTCTTCTAATAGATGGCACAGCGTCATTGAGCCCTGGAATGA
TGATGGGCATGTTCAACATGCTAAGTACGGTTTTAGGAGTCTCAATACTGAATCTTG
GGCAAAAGAAATACACCAAAACAACATACTGGTGGGATGGGCTTCAATCCTCTGAT
GATTTTGCTCTCATAGTGAATGCACCAAATCATGAGGGAATACAAGCAGGAGTGGA
TAGATTCTACAGAACCTGCAAGCTAGTCGGAATCAATATGAGCAAGAAGAAGTCCT
ATATAAATAGGACAGGAACATTTGAATTCACAAGCTTTTTTTATCGCTATGGATTTGT
GGCCAATTTTAGCATGGAGCTGCCCAGTTTTGGAGTGTCTGGGATTAATGAATCAG
CTGATATGAGCATTGGAGTAACAGTGATAAAGAACAACATGATAAACAATGACCTTG
GACCAGCAACAGCCCAGATGGCTCTTCAACTGTTCATCAAGGACTACAGATATACA
TATCGGTGCCACAGAGGAGACACACAAATTCAGACGAGGAGATCATTTGAGCTAAA
GAAGCTGTGGGAGCAAACCCGATCAAAGGCAGGACTATTGGTTTCAGATGGAGGA
CCGAACTTATACAATATCCGGAATCTTCACATCCCTGAAGTCTGCTTAAAGTGGGAG
CTAATGGATGAAGACTATCAGGGAAGACTTTGTAATCCCCTGAATCCATTTGTCAGC
CATAAAGAGATTGAGTCTGTAAACAATGCTGTGGTAATGCCAGCTCATGGTCCAGC
CAAGAGCATGGAATATGACGCTGTTGCAACTACACACTCCTGGATTCCCAAGAGGA
ACCGCTCTATTCTCAACACAAaCCAAAGGGGAATTCTTGAGGATGAACAGATGTATC
AGAAGTGCTGCAACCTGTTCGAGAAATTTTTCCCCAGTAGTTCATACAGGAGACCG
GTTGGAATTTCCAGCATGGTGGAGGCCATGGTGTCTAGGGCCCGGATTGATGCCA
GAATTGACTTCGAGTCTGGACGGATTAAGAAAGAAGAGTTCTCCGAGATCATGAAG
ATCTGTTCCACCATTGAAGAGCTCAGACGGCAAAAACAATGAatttagcttgtccttcatgaaaa
aatgccttgtttctact (SEQ ID No. 31)

IVR-116 delNS PB1 E97G and S678N
Amino acid sequence
MDVNPTLLFLKIPAQNAISTTFPYTGDPPYSHGTGTGYTMDTVNRTHQYSEKGKWTTNTETGA
PQLNPIDGPLPEDNEPSGYAQTDCVLEAMAFLGGSHPGIFENSCLETMEVVQQTRVDRLTQGR
QTYDWTLNRNQPAATALANTIEVFRSNGLTANESGRLIDFLKDVMESMDKEEIEITTHFQRKRRV
RDNMTKKMVTQRTIGKKKQRVNKRSYLIRALTLNTMTKDAERGKLKRRAIATPGMQIRGFVYFV
ETLARSICEKLEQSGLPVGGNEKKAKLANVVRKMMTNSQDTELSFTITGDNTKWNENQNPRMF
LAMITYITKNQPEWFRNILSIAPIMFSNKMARLGKGYMFESKRMKLRTQIPAEMLASIDLKYFNES
TRKKIEKIRPLLIDGTASLSPGMMMGMFNMLSTVLGVSILNLGQKKYTKTTYWWDGLQSSDDFA
LIVNAPNHEGIQAGVDRFYRTCKLVGINMSKKKSYINRTGTFEFTSFFYRYGFVANFSMELPSFG
VSGINESADMSIGVTVIKNNMINNDLGPATAQMALQLFIKDYRYTYRCHRGDTQIQTRRSFELKK
LWEQTRSKAGLLVSDGGPNLYNIRNLHIPEVCLKWELMDEDYQGRLCNPLNPFVSHKEIESVNN
AVVMPAHGPAKSMEYDAVATTHSWIPKRNRSILNTnQRGILEDEQMYQKCCNLFEKFFPSSSY
RRPVGISSMVEAMVSRARIDARIDFESGRIKKEEFSEIMKICSTIEELRRQKQ (SEQ ID No. 32)

B/Thüringen/02/06 NS a269g mutations
Nucleotide Sequence:

Figure 4 continued
agcagaagcagaggatttgtttagtcactggcaaacaggaaaaATGGCGGACAATATGACCACAACAC
AAATTGAGTGGAGGATGAAGAAGATGGCCATCGGATCCTCAATTCACTCTTCGAGC
GTCTTAATGAAGGACATTCAAAGCCAATTCGAGCAGCTGAAACTGCGGTGGGAGTC
TTATCCCAATTTGGTCAAGAGCACCGATTATCACCAGAAGAGGGAGACAATTAGAC
TGGTCACGGAAGAACTTTATCTTTTAAGTAAAgGAATTGATGATAACATATTGTTCCA
CAAAACAGTAATAGCTAACAGCTCCATAATAGCTGACATGGTTGTATCATTATCATT
ATTAGAAACATTGTATGAAATGAAGGATGTGGTTGAAGTGTACAGCAGGCAGTGCT
TGTGAatttaaaataaaaatcctcttgttactact (SEQ ID No. 33)

B/Thüringen/02/06 NS R76G
Amino Acid Sequence NS2:
MADNMTTTQIEWRMKKMAIGSSIHSSSVLMKDIQSQFEQLKLRWESYPNLVKSTDYHQ
KRETIRLVTEELYLLSKgIDDNILFHKTVIANSSIIADMVVSLSLLETLYEMKDVVEVYSR
(SEQ ID No. 34)

IVR-116 delNS PB1 a314g
Nucleotide Sequence
agcgaaagcaggcaaaccatttgaatggATGTCAATCCGACTTTACTTTTCTTGAAAATTCCAGC
GCAAAATGCCATAAGCACCACATTCCCTTATACTGGAGATCCTCCATACAGCCATG
GAACAGGAACAGGATACACCATGGACACAGTTAACAGAACACATCAATATTCAGAA
AAAGGGAAATGGACAACAAACACAGAAACTGGGGCGCCCCAACTTAACCCGATTG
ATGGACCACTACCTGAGGATAATGAGCCAAGTGGATATGCACAAACAGACTGTGTC
CTGGAAGCTATGGCTTTCCTTGAGGgATCCCACCCAGGGATCTTTGAAAACTCGTG
CCTTGAAACAATGGAAGTCGTTCAACAAACAAGAGTGGACAGACTGACCCAAGGTC
GTCAGACCTATGATTGGACATTAAACAGAAATCAACCAGCCGCAACTGCATTAGCC
AACACTATAGAAGTTTTCAGATCGAATGGTCTAACAGCTAATGAGTCGGGAAGGCT
AATAGATTTCCTCAAGGATGTGATGGAATCAATGGATAAAGAGGAAATAGAGATAAC
AACACACTTCCAAAGAAAAAGAAGAGTAAGAGACAACATGACCAAGAAAATGGTCA
CACAAAGAACAATAGGAAAGAAAAAGCAGAGAGTGAACAAGAGAAGCTATCTAATA
AGAGCATTAACTTTGAACACAATGACCAAAGATGCAGAAAGAGGTAAATTAAAGAGA
AGAGCTATTGCAACACCCGGGATGCAAATCAGAGGGTTCGTGTACTTTGTTGAAAC
TCTAGCTAGGAGCATTTGTGAGAAGCTTGAACAGTCTGGACTTCCAGTAGGAGGTA
ATGAAAAGAAGGCCAAACTGGCAAATGTTGTGAGAAAGATGATGACTAATTCACAA
GACACAGAGCTTTCTTTCACAATTACTGGAGACAATACTAAGTGGAATGAAAATCAA
AATCCTCGAATGTTCCTGGCGATGATTACATATATCACAAAAAATCAACCTGAATGG
TTCAGAAACATCCTGAGCATCGCACCCATAATGTTCTCAAACAAAATGGCGAGACTA
GGGAAAGGATACATGTTCGAAAGTAAGAGAATGAAGCTCCGAACACAAATACCAGC
AGAAATGCTAGCAAGCATTGACCTAAAGTATTTCAATGAATCAACAAGAAAGAAAAT
TGAGAAAATAAGGCCTCTTCTAATAGATGGCACAGCGTCATTGAGCCCTGGAATGA
TGATGGGCATGTTCAACATGCTAAGTACGGTTTTAGGAGTCTCAATACTGAATCTTG
GGCAAAAGAAATACACCAAAACAACATACTGGTGGGATGGGCTTCAATCCTCTGAT
GATTTTGCTCTCATAGTGAATGCACCAAATCATGAGGGAATACAAGCAGGAGTGGA
TAGATTCTACAGAACCTGCAAGCTAGTCGGAATCAATATGAGCAAGAAGAAGTCCT
ATATAAATAGGACAGGAACATTTGAATTCACAAGCTTTTTTTATCGCTATGGATTTGT
GGCCAATTTTAGCATGGAGCTGCCCAGTTTTGGAGTGTCTGGGATTAATGAATCAG
CTGATATGAGCATTGGAGTAACAGTGATAAAGAACAACATGATAAACAATGACCTTG Figure 4 continued
GACCAGCAACAGCCCAGATGGCTCTTCAACTGTTCATCAAGGACTACAGATATACA
TATCGGTGCCACAGAGGAGACACACAAATTCAGACGAGGAGATCATTTGAGCTAAA
GAAGCTGTGGGAGCAAACCCGATCAAAGGCAGGACTATTGGTTTCAGATGGAGGA
CCGAACTTATACAATATCCGGAATCTTCACATCCCTGAAGTCTGCTTAAAGTGGGAG
CTAATGGATGAAGACTATCAGGGAAGACTTTGTAATCCCCTGAATCCATTTGTCAGC
CATAAAGAGATTGAGTCTGTAAACAATGCTGTGGTAATGCCAGCTCATGGTCCAGC
CAAGAGCATGGAATATGACGCTGTTGCAACTACACACTCCTGGATTCCCAAGAGGA
ACCGCTCTATTCTCAACACAAGCCAAAGGGGAATTCTTGAGGATGAACAGATGTAT
CAGAAGTGCTGCAACCTGTTCGAGAAATTTTTCCCCAGTAGTTCATACAGGAGACC
GGTTGGAATTTCCAGCATGGTGGAGGCCATGGTGTCTAGGGCCCGGATTGATGCC
AGAATTGACTTCGAGTCTGGACGGATTAAGAAAGAAGAGTTCTCCGAGATCATGAA
GATCTGTTCCACCATTGAAGAGCTCAGACGGCAAAAACAATGAatttagcttgtccttcatgaa
aaaatgccttgtttctact (SEQ ID No. 35)

IVR-116 delNS PB1 g2057a
Nucleotide Sequence
agcgaaagcaggcaaaccatttgaatggATGTCAATCCGACTTTACTTTTCTTGAAAATTCCAGC
GCAAAATGCCATAAGCACCACATTCCCTTATACTGGAGATCCTCCATACAGCCATG
GAACAGGAACAGGATACACCATGGACACAGTTAACAGAACACATCAATATTCAGAA
AAAGGGAAATGGACAACAAACACAGAAACTGGGGCGCCCCAACTTAACCCGATTG
ATGGACCACTACCTGAGGATAATGAGCCAAGTGGATATGCACAAACAGACTGTGTC
CTGGAAGCTATGGCTTTCCTTGAGGAATCCCACCCAGGGATCTTTGAAAACTCGTG
CCTTGAAACAATGGAAGTCGTTCAACAAACAAGAGTGGACAGACTGACCCAAGGTC
GTCAGACCTATGATTGGACATTAAACAGAAATCAACCAGCCGCAACTGCATTAGCC
AACACTATAGAAGTTTTCAGATCGAATGGTCTAACAGCTAATGAGTCGGGAAGGCT
AATAGATTTCCTCAAGGATGTGATGGAATCAATGGATAAAGAGGAAATAGAGATAAC
AACACACTTCCAAAGAAAAAGAAGAGTAAGAGACAACATGACCAAGAAAATGGTCA
CACAAAGAACAATAGGAAAGAAAAAGCAGAGAGTGAACAAGAGAAGCTATCTAATA
AGAGCATTAACTTTGAACACAATGACCAAAGATGCAGAAAGAGGTAAATTAAAGAGA
AGAGCTATTGCAACACCCGGGATGCAAATCAGAGGGTTCGTGTACTTTGTTGAAAC
TCTAGCTAGGAGCATTTGTGAGAAGCTTGAACAGTCTGGACTTCCAGTAGGAGGTA
ATGAAAAGAAGGCCAAACTGGCAAATGTTGTGAGAAAGATGATGACTAATTCACAA
GACACAGAGCTTTCTTTCACAATTACTGGAGACAATACTAAGTGGAATGAAAATCAA
AATCCTCGAATGTTCCTGGCGATGATTACATATATCACAAAAAATCAACCTGAATGG
TTCAGAAACATCCTGAGCATCGCACCCATAATGTTCTCAAACAAAATGGCGAGACTA
GGGAAAGGATACATGTTCGAAAGTAAGAGAATGAAGCTCCGAACACAAATACCAGC
AGAAATGCTAGCAAGCATTGACCTAAAGTATTTCAATGAATCAACAAGAAAGAAAAT
TGAGAAAATAAGGCCTCTTCTAATAGATGGCACAGCGTCATTGAGCCCTGGAATGA
TGATGGGCATGTTCAACATGCTAAGTACGGTTTTAGGAGTCTCAATACTGAATCTTG
GGCAAAAGAAATACACCAAAACAACATACTGGTGGGATGGGCTTCAATCCTCTGAT
GATTTTGCTCTCATAGTGAATGCACCAAATCATGAGGGAATACAAGCAGGAGTGGA
TAGATTCTACAGAACCTGCAAGCTAGTCGGAATCAATATGAGCAAGAAGAAGTCCT
ATATAAATAGGACAGGAACATTTGAATTCACAAGCTTTTTTTATCGCTATGGATTTGT
GGCCAATTTTAGCATGGAGCTGCCCAGTTTTGGAGTGTCTGGGATTAATGAATCAG
CTGATATGAGCATTGGAGTAACAGTGATAAAGAACAACATGATAAACAATGACCTTG
GACCAGCAACAGCCCAGATGGCTCTTCAACTGTTCATCAAGGACTACAGATATACA
TATCGGTGCCACAGAGGAGACACACAAATTCAGACGAGGAGATCATTTGAGCTAAA

Figure 4 continued

GAAGCTGTGGGAGCAAACCCGATCAAAGGCAGGACTATTGGTTTCAGATGGAGGA
CCGAACTTATACAATATCCGGAATCTTCACATCCCTGAAGTCTGCTTAAAGTGGGAG
CTAATGGATGAAGACTATCAGGGAAGACTTTGTAATCCCCTGAATCCATTTGTCAGC
CATAAAGAGATTGAGTCTGTAAACAATGCTGTGGTAATGCCAGCTCATGGTCCAGC
CAAGAGCATGGAATATGACGCTGTTGCAACTACACACTCCTGGATTCCCAAGAGGA
ACCGCTCTATTCTCAACACAAaCCAAAGGGGAATTCTTGAGGATGAACAGATGTATC
AGAAGTGCTGCAACCTGTTCGAGAAATTTTTCCCCAGTAGTTCATACAGGAGACCG
GTTGGAATTTCCAGCATGGTGGAGGCCATGGTGTCTAGGGCCCGGATTGATGCCA
GAATTGACTTCGAGTCTGGACGGATTAAGAAAGAAGAGTTCTCCGAGATCATGAAG
ATCTGTTCCACCATTGAAGAGCTCAGACGGCAAAAACAATGAatttagcttgtccttcatgaaaa
aatgccttgtttctact (SEQ ID No. 36)

IVR-116 delNS PB1 E97G
Amino acid sequence
MDVNPTLLFLKIPAQNAISTTFPYTGDPPYSHGTGTGYTMDTVNRTHQYSEKGKWTTNTETGA
PQLNPIDGPLPEDNEPSGYAQTDCVLEAMAFLGGSHPGIFENSCLETMEVVQQTRVDRLTQGR
QTYDWTLNRNQPAATALANTIEVFRSNGLTANESGRLIDFLKDVMESMDKEEIEITTHFQRKRRV
RDNMTKKMVTQRTIGKKKQRVNKRSYLIRALTLNTMTKDAERGKLKRRAIATPGMQIRGFVYFV
ETLARSICEKLEQSGLPVGGNEKKAKLANVVRKMMTNSQDTELSFTITGDNTKWNENQNPRMF
LAMITYITKNQPEWFRNILSIAPIMFSNKMARLGKGYMFESKRMKLRTQIPAEMLASIDLKYFNES
TRKKIEKIRPLLIDGTASLSPGMMMGMFNMLSTVLGVSILNLGQKKYTKTTYWWDGLQSSDDFA
LIVNAPNHEGIQAGVDRFYRTCKLVGINMSKKKSYINRTGTFEFTSFFYRYGFVANFSMELPSFG
VSGINESADMSIGVTVIKNNMINNDLGPATAQMALQLFIKDYRYTYRCHRGDTQIQTRRSFELKK
LWEQTRSKAGLLVSDGGPNLYNIRNLHIPEVCLKWELMDEDYQGRLCNPLNPFVSHKEIESVNN
AVVMPAHGPAKSMEYDAVATTHSWIPKRNRSILNTSQRGILEDEQMYQKCCNLFEKFFPSSSY
RRPVGISSMVEAMVSRARIDARIDFESGRIKKEEFSEIMKICSTIEELRRQKQ (SEQ ID No. 37)

IVR-116 delNS PB1 S678N
Amino acid sequence
MDVNPTLLFLKIPAQNAISTTFPYTGDPPYSHGTGTGYTMDTVNRTHQYSEKGKWTTNTETGA
PQLNPIDGPLPEDNEPSGYAQTDCVLEAMAFLEGSHPGIFENSCLETMEVVQQTRVDRLTQGR
QTYDWTLNRNQPAATALANTIEVFRSNGLTANESGRLIDFLKDVMESMDKEEIEITTHFQRKRRV
RDNMTKKMVTQRTIGKKKQRVNKRSYLIRALTLNTMTKDAERGKLKRRAIATPGMQIRGFVYFV
ETLARSICEKLEQSGLPVGGNEKKAKLANVVRKMMTNSQDTELSFTITGDNTKWNENQNPRMF
LAMITYITKNQPEWFRNILSIAPIMFSNKMARLGKGYMFESKRMKLRTQIPAEMLASIDLKYFNES
TRKKIEKIRPLLIDGTASLSPGMMMGMFNMLSTVLGVSILNLGQKKYTKTTYWWDGLQSSDDFA
LIVNAPNHEGIQAGVDRFYRTCKLVGINMSKKKSYINRTGTFEFTSFFYRYGFVANFSMELPSFG
VSGINESADMSIGVTVIKNNMINNDLGPATAQMALQLFIKDYRYTYRCHRGDTQIQTRRSFELKK
LWEQTRSKAGLLVSDGGPNLYNIRNLHIPEVCLKWELMDEDYQGRLCNPLNPFVSHKEIESVNN
AVVMPAHGPAKSMEYDAVATTHSWIPKRNRSILNTnQRGILEDEQMYQKCCNLFEKFFPSSSY
RRPVGISSMVEAMVSRARIDARIDFESGRIKKEEFSEIMKICSTIEELRRQKQ (SEQ ID No. 38)

SEQUENCE LISTING

<160> NUMBER OF SEQ ID NOS: 38

<210> SEQ ID NO 1
<211> LENGTH: 2396
<212> TYPE: DNA
<213> ORGANISM: Influenza B virus

<400> SEQUENCE: 1

```
agcagaagcg gagcgttttc aagatgacat tggctaaaat tgaattgtta aaacaactgt     60

taagggacaa tgaagccaaa acagtactga aacaaacaac agtagatcaa tataacataa    120

taagaaaatt caatacatca agaattgaaa agaacccttc attaaggatg aagtgggcga    180

tgtgttctaa ttttcccttg gctttgacca agggtgacat ggcaaacaga atccccttgg    240

aatacaaggg aatacaactt aaaacaaatg ctgaagacat aggaaccaaa ggccaaatgt    300

gctcaatagc agcagttacc tggtggaata catatggacc aataggggat actgaaggtt    360

tcgaaaaagt ctacgaaagc ttttttctca gaaagatgag acttgacaat gccacttggg    420

gccgaataac ttttggccca gttgaaagag taagaaaaag ggtactgcta aaccctctca    480

ccaaggaaat gcctccagat gaagcaagta atgtgataat ggaaatattg ttccctaaag    540

aagcaggaat accaagagaa tctacttgga tacataggga actgataaaa gaaaaaagag    600

aaaaattgaa aggaacgatg ataactccca ttgtactggc atacatgctc gagagggaat    660

tagttgccag gagaaggttc ctgcccgtgg caggagcaac atcagctgag ttcatagaaa    720

tgctacactg cttacaaggt gaaaattgga ggcaaatata tcacccggga gggaataaac    780

taactgaatc taggtcccaa tcgatgattg tggcttgtag aaagataatc agaagatcaa    840

tagtcgcatc aaacccattg gagctagctg tagaaattgc aaataagact gtgatagata    900

ctgaaccttt aaaatcatgt ctgacagcca tagacggagg tgatgtcgcc tgtgacataa    960

taagagctgc attaggacta aagatcagac aaagacaaag atttggacga cttgaactaa   1020

agagaatatc aggaagagga ttcaaaaatg atgaagaaat attaatcggg aacggaacaa   1080

tacagaagat tggaatatgg gacggagaag aggagttcca tgtgagatgt ggtgaatgca   1140

ggggaatatt aaaaaagagc aaaatgagaa tggaaaaact actaataaat tcagctaaaa   1200

aggaggacat gaaagattta ataatcttgt gcatggtatt ttcccaagac actaggatgt   1260

tccaaggagt gaggggtgaa ataaattttc ttaatagagc aggccaactt ttatctccaa   1320

tgtatcaact ccaaagatat tttttgagta gaagtaacga tctctttgat caatgggggt   1380

atgaggaatc acccaaagca agtgagctac atgggataaa tgaactaatg aatgcatctg   1440

actacacttt gaaaggggtt gtagtaacaa aaaatgtgat tgatgatttt agttctactg   1500

aaacagaaaa agtatctata acaaaaaatc ttagtttaat aaaaaggact ggggaagtca   1560
```

-continued

```
taatgggagc caatgacgta agtgaattag aatcacaagc acagctaatg ataacatatg   1620

atacaccaaa gatgtgggag atggggacaa ccaaagaact ggtgcaaaac acctatcaat   1680

gggtgctgaa aaatttggta acactgaagg ctcagtttct tctagggaaa gaagacatgt   1740

tccaatggga tgcatttgaa gcatttgaaa gcataatccc ccagaagatg gctggccaat   1800

acagtggatt tgcaagagca gtgctcaaac aaatgagaga ccaagaggtc atgaaaactg   1860

accagttcat aaagttgttg cccttttgtt tctcaccacc aaagttaagg agcaatgggg   1920

agccttatca gttcttgagg cttgtattga agggaggagg agaaaatttc atcgaagtaa   1980

ggaaagggtc tcctctattc tcttacaatc cacaaacaga agtcctaact atatgcggca   2040

gaatgatgtc attaaaaggg aaaattgaag atgaagaaag gaatagatca atggggaatg   2100

cagtgttggc gggttttctt gttagtggca agtatgaccc agatcttgga gatttcaaaa   2160

ccattgaaga acttgaaaag ctaaaaccag gggagaaagc aaacatctta ctttatcaag   2220

gaaagcccgt taaagtagtt aaaaggaaaa gatatagtgc tttatccaat gacatttcac   2280

aaggaattaa gagacaaaga atgacagttg agtccatggg gtgggccttg agctaatata   2340

aatttatcca ttaattcaat gaatacaatt gagtgaaaaa tgctcgtgtt tctact       2396
```

```
<210> SEQ ID NO 2
<211> LENGTH: 770
<212> TYPE: PRT
<213> ORGANISM: Influenza B virus

<400> SEQUENCE: 2

Met Thr Leu Ala Lys Ile Glu Leu Leu Lys Gln Leu Leu Arg Asp Asn
1               5                   10                  15

Glu Ala Lys Thr Val Leu Lys Gln Thr Thr Val Asp Gln Tyr Asn Ile
            20                  25                  30

Ile Arg Lys Phe Asn Thr Ser Arg Ile Glu Lys Asn Pro Ser Leu Arg
        35                  40                  45

Met Lys Trp Ala Met Cys Ser Asn Phe Pro Leu Ala Leu Thr Lys Gly
    50                  55                  60

Asp Met Ala Asn Arg Ile Pro Leu Glu Tyr Lys Gly Ile Gln Leu Lys
65                  70                  75                  80

Thr Asn Ala Glu Asp Ile Gly Thr Lys Gly Gln Met Cys Ser Ile Ala
                85                  90                  95

Ala Val Thr Trp Trp Asn Thr Tyr Gly Pro Ile Gly Asp Thr Glu Gly
            100                 105                 110

Phe Glu Lys Val Tyr Glu Ser Phe Phe Leu Arg Lys Met Arg Leu Asp
        115                 120                 125

Asn Ala Thr Trp Gly Arg Ile Thr Phe Gly Pro Val Glu Arg Val Arg
    130                 135                 140

Lys Arg Val Leu Leu Asn Pro Leu Thr Lys Glu Met Pro Pro Asp Glu
145                 150                 155                 160

Ala Ser Asn Val Ile Met Glu Ile Leu Phe Pro Lys Glu Ala Gly Ile
                165                 170                 175

Pro Arg Glu Ser Thr Trp Ile His Arg Glu Leu Ile Lys Glu Lys Arg
            180                 185                 190

Glu Lys Leu Lys Gly Thr Met Ile Thr Pro Ile Val Leu Ala Tyr Met
        195                 200                 205

Leu Glu Arg Glu Leu Val Ala Arg Arg Arg Phe Leu Pro Val Ala Gly
    210                 215                 220

Ala Thr Ser Ala Glu Phe Ile Glu Met Leu His Cys Leu Gln Gly Glu
```

-continued

```
225                 230                 235                 240

Asn Trp Arg Gln Ile Tyr His Pro Gly Gly Asn Lys Leu Thr Glu Ser
                245                 250                 255

Arg Ser Gln Ser Met Ile Val Ala Cys Arg Lys Ile Ile Arg Arg Ser
            260                 265                 270

Ile Val Ala Ser Asn Pro Leu Glu Leu Ala Val Glu Ile Ala Asn Lys
        275                 280                 285

Thr Val Ile Asp Thr Glu Pro Leu Lys Ser Cys Leu Thr Ala Ile Asp
    290                 295                 300

Gly Gly Asp Val Ala Cys Asp Ile Ile Arg Ala Ala Leu Gly Leu Lys
305                 310                 315                 320

Ile Arg Gln Arg Gln Arg Phe Gly Arg Leu Glu Leu Lys Arg Ile Ser
                325                 330                 335

Gly Arg Gly Phe Lys Asn Asp Glu Glu Ile Leu Ile Gly Asn Gly Thr
            340                 345                 350

Ile Gln Lys Ile Gly Ile Trp Asp Gly Glu Glu Glu Phe His Val Arg
        355                 360                 365

Cys Gly Glu Cys Arg Gly Ile Leu Lys Lys Ser Lys Met Arg Met Glu
    370                 375                 380

Lys Leu Leu Ile Asn Ser Ala Lys Lys Glu Asp Met Lys Asp Leu Ile
385                 390                 395                 400

Ile Leu Cys Met Val Phe Ser Gln Asp Thr Arg Met Phe Gln Gly Val
                405                 410                 415

Arg Gly Glu Ile Asn Phe Leu Asn Arg Ala Gly Gln Leu Leu Ser Pro
            420                 425                 430

Met Tyr Gln Leu Gln Arg Tyr Phe Leu Ser Arg Ser Asn Asp Leu Phe
        435                 440                 445

Asp Gln Trp Gly Tyr Glu Glu Ser Pro Lys Ala Ser Glu Leu His Gly
    450                 455                 460

Ile Asn Glu Leu Met Asn Ala Ser Asp Tyr Thr Leu Lys Gly Val Val
465                 470                 475                 480

Val Thr Lys Asn Val Ile Asp Asp Phe Ser Ser Thr Glu Thr Glu Lys
                485                 490                 495

Val Ser Ile Thr Lys Asn Leu Ser Leu Ile Lys Arg Thr Gly Glu Val
            500                 505                 510

Ile Met Gly Ala Asn Asp Val Ser Glu Leu Glu Ser Gln Ala Gln Leu
        515                 520                 525

Met Ile Thr Tyr Asp Thr Pro Lys Met Trp Glu Met Gly Thr Thr Lys
    530                 535                 540

Glu Leu Val Gln Asn Thr Tyr Gln Trp Val Leu Lys Asn Leu Val Thr
545                 550                 555                 560

Leu Lys Ala Gln Phe Leu Leu Gly Lys Glu Asp Met Phe Gln Trp Asp
                565                 570                 575

Ala Phe Glu Ala Phe Glu Ser Ile Ile Pro Gln Lys Met Ala Gly Gln
            580                 585                 590

Tyr Ser Gly Phe Ala Arg Ala Val Leu Lys Gln Met Arg Asp Gln Glu
        595                 600                 605

Val Met Lys Thr Asp Gln Phe Ile Lys Leu Leu Pro Phe Cys Phe Ser
    610                 615                 620

Pro Pro Lys Leu Arg Ser Asn Gly Glu Pro Tyr Gln Phe Leu Arg Leu
625                 630                 635                 640

Val Leu Lys Gly Gly Gly Glu Asn Phe Ile Glu Val Arg Lys Gly Ser
                645                 650                 655
```

```
Pro Leu Phe Ser Tyr Asn Pro Gln Thr Glu Val Leu Thr Ile Cys Gly
            660                 665                 670

Arg Met Met Ser Leu Lys Gly Lys Ile Glu Asp Glu Glu Arg Asn Arg
        675                 680                 685

Ser Met Gly Asn Ala Val Leu Ala Gly Phe Leu Val Ser Gly Lys Tyr
    690                 695                 700

Asp Pro Asp Leu Gly Asp Phe Lys Thr Ile Glu Glu Leu Glu Lys Leu
705                 710                 715                 720

Lys Pro Gly Glu Lys Ala Asn Ile Leu Leu Tyr Gln Gly Lys Pro Val
                725                 730                 735

Lys Val Val Lys Arg Lys Arg Tyr Ser Ala Leu Ser Asn Asp Ile Ser
            740                 745                 750

Gln Gly Ile Lys Arg Gln Arg Met Thr Val Glu Ser Met Gly Trp Ala
        755                 760                 765

Leu Ser
    770


<210> SEQ ID NO 3
<211> LENGTH: 2396
<212> TYPE: DNA
<213> ORGANISM: Artificial Sequence
<220> FEATURE:
<223> OTHER INFORMATION: PB2 G427S

<400> SEQUENCE: 3

agcagaagcg gagcgttttc aagatgacat tggctaaaat tgaattgtta aaacaactgt      60

taagggacaa tgaagccaaa acagtactga aacaaacaac agtagatcaa tataacataa     120

taagaaaatt caatacatca agaattgaaa agaacccttc attaaggatg aagtgggcga     180

tgtgttctaa ttttcccttg gctttgacca agggtgacat ggcaaacaga atccccttgg     240

aatacaaggg aatacaactt aaaacaaatg ctgaagacat aggaaccaaa ggccaaatgt     300

gctcaatagc agcagttacc tggtggaata catatggacc aataggggat actgaaggtt     360

tcgaaaaagt ctacgaaagc ttttttctca gaaagatgag acttgacaat gccacttggg     420

gccgaataac ttttggccca gttgaaagag taagaaaaag ggtactgcta aaccctctca     480

ccaaggaaat gcctccagat gaagcaagta atgtgataat ggaaatattg ttccctaaag     540

aagcaggaat accaagagaa tctacttgga tacataggga actgataaaa gaaaaaagag     600

aaaaattgaa aggaacgatg ataactccca ttgtactggc atacatgctc gagagggaat     660

tagttgccag gagaaggttc ctgcccgtgg caggagcaac atcagctgag ttcatagaaa     720

tgctacactg cttacaaggt gaaaattgga ggcaaatata tcacccggga gggaataaac     780

taactgaatc taggtcccaa tcgatgattg tggcttgtag aaagataatc agaagatcaa     840

tagtcgcatc aaacccattg gagctagctg tagaaattgc aaataagact gtgatagata     900

ctgaaccttt aaaatcatgt ctgacagcca tagacggagg tgatgtcgcc tgtgacataa     960

taagagctgc attaggacta aagatcagac aaagacaaag atttggacga cttgaactaa    1020

agagaatatc aggaagagga ttcaaaaatg atgaagaaat attaatcggg aacggaacaa    1080

tacagaagat tggaatatgg gacggagaag aggagttcca tgtgagatgt ggtgaatgca    1140

ggggaatatt aaaaaagagc aaaatgagaa tggaaaaact actaataaat tcagctaaaa    1200

aggaggacat gaaagattta ataatcttgt gcatggtatt ttcccaagac actaggatgt    1260

tccaaggagt gaggggtgaa ataaattttc ttaatagagc aagccaactt ttatctccaa    1320
```

-continued

```
tgtatcaact ccaaagatat tttttgagta gaagtaacga tctctttgat caatgggggt   1380

atgaggaatc acccaaagca agtgagctac atgggataaa tgaactaatg aatgcatctg   1440

actacacttt gaaaggggtt gtagtaacaa aaaatgtgat tgatgatttt agttctactg   1500

aaacagaaaa agtatctata acaaaaaatc ttagtttaat aaaaaggact ggggaagtca   1560

taatgggagc caatgacgta agtgaattag aatcacaagc acagctaatg ataacatatg   1620

atacaccaaa gatgtgggag atggggacaa ccaaagaact ggtgcaaaac acctatcaat   1680

gggtgctgaa aaatttggta acactgaagg ctcagtttct tctagggaaa gaagacatgt   1740

tccaatggga tgcatttgaa gcatttgaaa gcataatccc ccagaagatg gctggccaat   1800

acagtggatt tgcaagagca gtgctcaaac aaatgagaga ccaagaggtc atgaaaactg   1860

accagttcat aaagttgttg ccctttttgtt tctcaccacc aaagttaagg agcaatgggg   1920

agccttatca gttcttgagg cttgtattga agggaggagg agaaaatttc atcgaagtaa   1980

ggaaagggtc tcctctattc tcttacaatc cacaaacaga agtcctaact atatgcggca   2040

gaatgatgtc attaaaaggg aaaattgaag atgaagaaag gaatagatca atggggaatg   2100

cagtgttggc gggttttctt gttagtggca agtatgaccc agatcttgga gatttcaaaa   2160

ccattgaaga acttgaaaag ctaaaaccag gggagaaagc aaacatctta ctttatcaag   2220

gaaagcccgt taaagtagtt aaaaggaaaa gatatagtgc tttatccaat gacatttcac   2280

aaggaattaa gagacaaaga atgacagttg agtccatggg gtgggccttg agctaatata   2340

aatttatcca ttaattcaat gaatacaatt gagtgaaaaa tgctcgtgtt tctact       2396
```

<210> SEQ ID NO 4
<211> LENGTH: 770
<212> TYPE: PRT
<213> ORGANISM: Artificial Sequence
<220> FEATURE:
<223> OTHER INFORMATION: PB2 G427S

<400> SEQUENCE: 4

```
Met Thr Leu Ala Lys Ile Glu Leu Leu Lys Gln Leu Leu Arg Asp Asn
1               5                   10                  15

Glu Ala Lys Thr Val Leu Lys Gln Thr Thr Val Asp Gln Tyr Asn Ile
            20                  25                  30

Ile Arg Lys Phe Asn Thr Ser Arg Ile Glu Lys Asn Pro Ser Leu Arg
        35                  40                  45

Met Lys Trp Ala Met Cys Ser Asn Phe Pro Leu Ala Leu Thr Lys Gly
    50                  55                  60

Asp Met Ala Asn Arg Ile Pro Leu Glu Tyr Lys Gly Ile Gln Leu Lys
65                  70                  75                  80

Thr Asn Ala Glu Asp Ile Gly Thr Lys Gly Gln Met Cys Ser Ile Ala
                85                  90                  95

Ala Val Thr Trp Trp Asn Thr Tyr Gly Pro Ile Gly Asp Thr Glu Gly
            100                 105                 110

Phe Glu Lys Val Tyr Glu Ser Phe Phe Leu Arg Lys Met Arg Leu Asp
        115                 120                 125

Asn Ala Thr Trp Gly Arg Ile Thr Phe Gly Pro Val Glu Arg Val Arg
    130                 135                 140

Lys Arg Val Leu Leu Asn Pro Leu Thr Lys Glu Met Pro Pro Asp Glu
145                 150                 155                 160

Ala Ser Asn Val Ile Met Glu Ile Leu Phe Pro Lys Glu Ala Gly Ile
                165                 170                 175
```

-continued

```
Pro Arg Glu Ser Thr Trp Ile His Arg Glu Leu Ile Lys Glu Lys Arg
            180                 185                 190

Glu Lys Leu Lys Gly Thr Met Ile Thr Pro Ile Val Leu Ala Tyr Met
        195                 200                 205

Leu Glu Arg Glu Leu Val Ala Arg Arg Arg Phe Leu Pro Val Ala Gly
    210                 215                 220

Ala Thr Ser Ala Glu Phe Ile Glu Met Leu His Cys Leu Gln Gly Glu
225                 230                 235                 240

Asn Trp Arg Gln Ile Tyr His Pro Gly Gly Asn Lys Leu Thr Glu Ser
                245                 250                 255

Arg Ser Gln Ser Met Ile Val Ala Cys Arg Lys Ile Ile Arg Arg Ser
            260                 265                 270

Ile Val Ala Ser Asn Pro Leu Glu Leu Ala Val Glu Ile Ala Asn Lys
        275                 280                 285

Thr Val Ile Asp Thr Glu Pro Leu Lys Ser Cys Leu Thr Ala Ile Asp
    290                 295                 300

Gly Gly Asp Val Ala Cys Asp Ile Ile Arg Ala Ala Leu Gly Leu Lys
305                 310                 315                 320

Ile Arg Gln Arg Gln Arg Phe Gly Arg Leu Glu Leu Lys Arg Ile Ser
                325                 330                 335

Gly Arg Gly Phe Lys Asn Asp Glu Glu Ile Leu Ile Gly Asn Gly Thr
            340                 345                 350

Ile Gln Lys Ile Gly Ile Trp Asp Gly Glu Glu Glu Phe His Val Arg
        355                 360                 365

Cys Gly Glu Cys Arg Gly Ile Leu Lys Lys Ser Lys Met Arg Met Glu
    370                 375                 380

Lys Leu Leu Ile Asn Ser Ala Lys Lys Glu Asp Met Lys Asp Leu Ile
385                 390                 395                 400

Ile Leu Cys Met Val Phe Ser Gln Asp Thr Arg Met Phe Gln Gly Val
                405                 410                 415

Arg Gly Glu Ile Asn Phe Leu Asn Arg Ala Ser Gln Leu Leu Ser Pro
            420                 425                 430

Met Tyr Gln Leu Gln Arg Tyr Phe Leu Ser Arg Ser Asn Asp Leu Phe
        435                 440                 445

Asp Gln Trp Gly Tyr Glu Glu Ser Pro Lys Ala Ser Glu Leu His Gly
    450                 455                 460

Ile Asn Glu Leu Met Asn Ala Ser Asp Tyr Thr Leu Lys Gly Val Val
465                 470                 475                 480

Val Thr Lys Asn Val Ile Asp Asp Phe Ser Ser Thr Glu Thr Glu Lys
                485                 490                 495

Val Ser Ile Thr Lys Asn Leu Ser Leu Ile Lys Arg Thr Gly Glu Val
            500                 505                 510

Ile Met Gly Ala Asn Asp Val Ser Glu Leu Glu Ser Gln Ala Gln Leu
        515                 520                 525

Met Ile Thr Tyr Asp Thr Pro Lys Met Trp Glu Met Gly Thr Thr Lys
    530                 535                 540

Glu Leu Val Gln Asn Thr Tyr Gln Trp Val Leu Lys Asn Leu Val Thr
545                 550                 555                 560

Leu Lys Ala Gln Phe Leu Leu Gly Lys Glu Asp Met Phe Gln Trp Asp
                565                 570                 575

Ala Phe Glu Ala Phe Glu Ser Ile Ile Pro Gln Lys Met Ala Gly Gln
            580                 585                 590

Tyr Ser Gly Phe Ala Arg Ala Val Leu Lys Gln Met Arg Asp Gln Glu
```

-continued

```
        595                 600                 605

Val Met Lys Thr Asp Gln Phe Ile Lys Leu Leu Pro Phe Cys Phe Ser
    610                 615                 620

Pro Pro Lys Leu Arg Ser Asn Gly Glu Pro Tyr Gln Phe Leu Arg Leu
625                 630                 635                 640

Val Leu Lys Gly Gly Gly Glu Asn Phe Ile Glu Val Arg Lys Gly Ser
                645                 650                 655

Pro Leu Phe Ser Tyr Asn Pro Gln Thr Glu Val Leu Thr Ile Cys Gly
            660                 665                 670

Arg Met Met Ser Leu Lys Gly Lys Ile Glu Asp Glu Glu Arg Asn Arg
        675                 680                 685

Ser Met Gly Asn Ala Val Leu Ala Gly Phe Leu Val Ser Gly Lys Tyr
    690                 695                 700

Asp Pro Asp Leu Gly Asp Phe Lys Thr Ile Glu Glu Leu Glu Lys Leu
705                 710                 715                 720

Lys Pro Gly Glu Lys Ala Asn Ile Leu Leu Tyr Gln Gly Lys Pro Val
                725                 730                 735

Lys Val Val Lys Arg Lys Arg Tyr Ser Ala Leu Ser Asn Asp Ile Ser
            740                 745                 750

Gln Gly Ile Lys Arg Gln Arg Met Thr Val Glu Ser Met Gly Trp Ala
        755                 760                 765

Leu Ser
    770


<210> SEQ ID NO 5
<211> LENGTH: 1190
<212> TYPE: DNA
<213> ORGANISM: Influenza B virus

<400> SEQUENCE: 5

agcagaagca cgcactttct taaaatgtcg ctgtttggag acacaattgc ctacctgctt     60

tcattgacag aagatggaga aggcaaagca gaactagcag aaaaattaca ctgttggttc    120

ggtgggaaag aatttgacct agactctgcc ttggaatgga taaaaaacaa aagatgctta    180

actgatatac agaaagcact aattggtgcc tctatctgct ttttaaaacc caaagaccag    240

gaaagaaaaa gaagattcat cacagagccc ctatcaggaa tgggaacaac agcaacaaaa    300

aagaagggcc tgattctagc tgagagaaaa atgagaaaat gtgtgagctt ccatgaagca    360

tttgaaatag cagaaggcca tgaaagctca gcgttactat attgtctcat ggtcatgtac    420

ctgaatcctg gaaattattc aatgcaagta aaactaggaa cgctctgtgc tttgtgcgaa    480

aaacaagcat cacattcaca cagggctcat agcagagcag cgagatcttc agtgcccgga    540

gtgagacggg aaatgcagat ggtctcagct atgaacacag caaaaacaat gaatggaatg    600

ggaaaaggag aagacgtcca aaaactggca gaagaactgc aaagcaacat tggagtattg    660

agatctcttg ggcaagtcca aaagaatggg gaaggaattg caaaggatgt aatggaagtg    720

ctaaagcaga gctctatggg aaattcagct cttgtgaaga aatacctata atgctcgaac    780

catttcagat tctttcaatt tgttctttta ttttatcagc tctccatttc atggcttgga    840

caataggaca tttaaatcaa ataaaaagag gagtaaacat gaaaatacga ataaaggggc    900

caaataaaga gacaataaac agagaggtat caattttgag acacagttac caaaaagaaa    960

tccaggctaa agaagcaatg aaggaagtac tctctgacaa catggaggta ttgagtgacc   1020

acatagtaat tgaggggctt tctgctgaag agataataaa aatgggtgaa acagttttgg   1080
```

-continued

```
aggtagaaga atttcattaa attcaatttt tactgtactt cttactatgc atttaagcaa   1140

attgtaatca atgtcagcaa ataaactgga aaaagtgcgt tgtttctact              1190


<210> SEQ ID NO 6
<211> LENGTH: 248
<212> TYPE: PRT
<213> ORGANISM: Influenza B virus

<400> SEQUENCE: 6

Met Ser Leu Phe Gly Asp Thr Ile Ala Tyr Leu Leu Ser Leu Thr Glu
1               5                   10                  15

Asp Gly Glu Gly Lys Ala Glu Leu Ala Glu Lys Leu His Cys Trp Phe
            20                  25                  30

Gly Gly Lys Glu Phe Asp Leu Asp Ser Ala Leu Glu Trp Ile Lys Asn
        35                  40                  45

Lys Arg Cys Leu Thr Asp Ile Gln Lys Ala Leu Ile Gly Ala Ser Ile
    50                  55                  60

Cys Phe Leu Lys Pro Lys Asp Gln Glu Arg Lys Arg Arg Phe Ile Thr
65                  70                  75                  80

Glu Pro Leu Ser Gly Met Gly Thr Thr Ala Thr Lys Lys Lys Gly Leu
                85                  90                  95

Ile Leu Ala Glu Arg Lys Met Arg Lys Cys Val Ser Phe His Glu Ala
            100                 105                 110

Phe Glu Ile Ala Glu Gly His Glu Ser Ser Ala Leu Leu Tyr Cys Leu
        115                 120                 125

Met Val Met Tyr Leu Asn Pro Gly Asn Tyr Ser Met Gln Val Lys Leu
    130                 135                 140

Gly Thr Leu Cys Ala Leu Cys Glu Lys Gln Ala Ser His Ser His Arg
145                 150                 155                 160

Ala His Ser Arg Ala Ala Arg Ser Ser Val Pro Gly Val Arg Arg Glu
                165                 170                 175

Met Gln Met Val Ser Ala Met Asn Thr Ala Lys Thr Met Asn Gly Met
            180                 185                 190

Gly Lys Gly Glu Asp Val Gln Lys Leu Ala Glu Glu Leu Gln Ser Asn
        195                 200                 205

Ile Gly Val Leu Arg Ser Leu Gly Ala Ser Gln Lys Asn Gly Glu Gly
    210                 215                 220

Ile Ala Lys Asp Val Met Glu Val Leu Lys Gln Ser Ser Met Gly Asn
225                 230                 235                 240

Ser Ala Leu Val Lys Lys Tyr Leu
                245


<210> SEQ ID NO 7
<211> LENGTH: 1190
<212> TYPE: DNA
<213> ORGANISM: Artificial Sequence
<220> FEATURE:
<223> OTHER INFORMATION: PB2 T89S

<400> SEQUENCE: 7

agcagaagca cgcactttct taaaatgtcg ctgtttggag acacaattgc ctacctgctt     60

tcattgacag aagatggaga aggcaaagca gaactagcag aaaaattaca ctgttggttc    120

ggtgggaaag aatttgacct agactctgcc ttggaatgga taaaaaacaa aagatgctta    180

actgatatac agaaagcact aattggtgcc tctatctgct tttaaaacc caaagaccag     240

gaaagaaaaa gaagattcat cacagagccc ctatcaggaa tgggaacatc agcaacaaaa    300
```

aagaagggcc tgattctagc tgagagaaaa atgagaaaat gtgtgagctt ccatgaagca 360
tttgaaatag cagaaggcca tgaaagctca gcgttactat attgtctcat ggtcatgtac 420
ctgaatcctg gaaattattc aatgcaagta aaactaggaa cgctctgtgc tttgtgcgaa 480
aaacaagcat cacattcaca cagggctcat agcagagcag cgagatcttc agtgcccgga 540
gtgagacggg aaatgcagat ggtctcagct atgaacacag caaaaacaat gaatggaatg 600
ggaaaaggag aagacgtcca aaaactggca gaagaactgc aaagcaacat tggagtattg 660
agatctcttg gggcaagtca aaagaatggg gaaggaattg caaaggatgt aatggaagtg 720
ctaaagcaga gctctatggg aaattcagct cttgtgaaga aatacctata atgctcgaac 780
catttcagat tctttcaatt tgttctttta ttttatcagc tctccatttc atggcttgga 840
caataggaca tttaaatcaa ataaaaagag gagtaaacat gaaaatacga ataaaggggc 900
caaataaaga gacaataaac agagaggtat caattttgag acacagttac caaaaagaaa 960
tccaggctaa agaagcaatg aaggaagtac tctctgacaa catggaggta ttgagtgacc 1020
acatagtaat tgaggggctt tctgctgaag agataataaa aatgggtgaa acagttttgg 1080
aggtagaaga atttcattaa attcaatttt tactgtactt cttactatgc atttaagcaa 1140
attgtaatca atgtcagcaa ataaactgga aaaagtgcgt tgtttctact 1190

<210> SEQ ID NO 8
<211> LENGTH: 248
<212> TYPE: PRT
<213> ORGANISM: Artificial Sequence
<220> FEATURE:
<223> OTHER INFORMATION: PB2 T89S

<400> SEQUENCE: 8

Met Ser Leu Phe Gly Asp Thr Ile Ala Tyr Leu Leu Ser Leu Thr Glu
1 5 10 15

Asp Gly Glu Gly Lys Ala Glu Leu Ala Glu Lys Leu His Cys Trp Phe
20 25 30

Gly Gly Lys Glu Phe Asp Leu Asp Ser Ala Leu Glu Trp Ile Lys Asn
35 40 45

Lys Arg Cys Leu Thr Asp Ile Gln Lys Ala Leu Ile Gly Ala Ser Ile
50 55 60

Cys Phe Leu Lys Pro Lys Asp Gln Glu Arg Lys Arg Arg Phe Ile Thr
65 70 75 80

Glu Pro Leu Ser Gly Met Gly Thr Ser Ala Thr Lys Lys Lys Gly Leu
85 90 95

Ile Leu Ala Glu Arg Lys Met Arg Lys Cys Val Ser Phe His Glu Ala
100 105 110

Phe Glu Ile Ala Glu Gly His Glu Ser Ser Ala Leu Leu Tyr Cys Leu
115 120 125

Met Val Met Tyr Leu Asn Pro Gly Asn Tyr Ser Met Gln Val Lys Leu
130 135 140

Gly Thr Leu Cys Ala Leu Cys Glu Lys Gln Ala Ser His Ser His Arg
145 150 155 160

Ala His Ser Arg Ala Ala Arg Ser Ser Val Pro Gly Val Arg Arg Glu
165 170 175

Met Gln Met Val Ser Ala Met Asn Thr Ala Lys Thr Met Asn Gly Met
180 185 190

Gly Lys Gly Glu Asp Val Gln Lys Leu Ala Glu Glu Leu Gln Ser Asn
195 200 205

-continued

```
Ile Gly Val Leu Arg Ser Leu Gly Ala Ser Gln Lys Asn Gly Glu Gly
    210                 215                 220

Ile Ala Lys Asp Val Met Glu Val Leu Lys Gln Ser Ser Met Gly Asn
225                 230                 235                 240

Ser Ala Leu Val Lys Lys Tyr Leu
                245
```

<210> SEQ ID NO 9
<211> LENGTH: 442
<212> TYPE: DNA
<213> ORGANISM: Influenza B virus

<400> SEQUENCE: 9

```
agcagaagca gaggatttgt ttagtcactg gcaaacagga aaaatggcgg acaatatgac      60

cacaacacaa attgagtgga ggatgaagaa gatggccatc ggatcctcaa ttcactcttc     120

gagcgtctta atgaaggaca ttcaaagcca attcgagcag ctgaaactgc ggtgggagtc     180

ttatcccaat ttggtcaaga gcaccgatta tcaccagaag agggagacaa ttagactggt     240

cacggaagaa ctttatcttt taagtaaaag aattgatgat aacatattgt tccacaaaac     300

agtaatagct aacagctcca taatagctga catggttgta tcattatcat tattagaaac     360

attgtatgaa atgaaggatg tggttgaagt gtacagcagg cagtgcttgt gaatttaaaa     420

taaaaatcct cttgttacta ct                                              442
```

<210> SEQ ID NO 10
<211> LENGTH: 122
<212> TYPE: PRT
<213> ORGANISM: Influenza B virus

<400> SEQUENCE: 10

```
Met Ala Asp Asn Met Thr Thr Thr Gln Ile Glu Trp Arg Met Lys Lys
1               5                   10                  15

Met Ala Ile Gly Ser Ser Ile His Ser Ser Ser Val Leu Met Lys Asp
            20                  25                  30

Ile Gln Ser Gln Phe Glu Gln Leu Lys Leu Arg Trp Glu Ser Tyr Pro
        35                  40                  45

Asn Leu Val Lys Ser Thr Asp Tyr His Gln Lys Arg Glu Thr Ile Arg
    50                  55                  60

Leu Val Thr Glu Glu Leu Tyr Leu Leu Ser Lys Lys Ile Asp Asp Asn
65                  70                  75                  80

Ile Leu Phe His Lys Thr Val Ile Ala Asn Ser Ser Ile Ile Ala Asp
                85                  90                  95

Met Val Val Ser Leu Ser Leu Leu Glu Thr Leu Tyr Glu Met Lys Asp
            100                 105                 110

Val Val Glu Val Tyr Ser Arg Gln Cys Leu
        115                 120
```

<210> SEQ ID NO 11
<211> LENGTH: 442
<212> TYPE: DNA
<213> ORGANISM: Artificial Sequence
<220> FEATURE:
<223> OTHER INFORMATION: NS2 K75R R76G

<400> SEQUENCE: 11

```
agcagaagca gaggatttgt ttagtcactg gcaaacagga aaaatggcgg acaatatgac      60

cacaacacaa attgagtgga ggatgaagaa gatggccatc ggatcctcaa ttcactcttc     120
```

-continued gagcgtctta atgaaggaca ttcaaagcca attcgagcag ctgaaactgc ggtgggagtc 180
ttatcccaat ttggtcaaga gcaccgatta tcaccagaag agggagacaa ttagactggt 240
cacggaagaa ctttatcttt taagtagagg aattgatgat aacatattgt tccacaaaac 300
agtaatagct aacagctcca taatagctga catggttgta tcattatcat tattagaaac 360
attgtatgaa atgaaggatg tggttgaagt gtacagcagg cagtgcttgt gaatttaaaa 420
taaaaatcct cttgttacta ct 442

<210> SEQ ID NO 12
<211> LENGTH: 119
<212> TYPE: PRT
<213> ORGANISM: Artificial Sequence
<220> FEATURE:
<223> OTHER INFORMATION: NS2 K75R R76G

<400> SEQUENCE: 12

Met Ala Asp Asn Met Thr Thr Thr Gln Ile Glu Trp Arg Met Lys Lys
1 5 10 15

Met Ala Ile Gly Ser Ser Ile His Ser Ser Ser Val Leu Met Lys Asp
20 25 30

Ile Gln Ser Gln Phe Glu Gln Leu Lys Leu Arg Trp Glu Ser Tyr Pro
35 40 45

Asn Leu Val Lys Ser Thr Asp Tyr His Gln Lys Arg Glu Thr Ile Arg
50 55 60

Leu Val Thr Glu Glu Leu Tyr Leu Leu Ser Arg Gly Ile Asp Asp Asn
65 70 75 80

Ile Leu Phe His Lys Thr Val Ile Ala Asn Ser Ser Ile Ile Ala Asp
85 90 95

Met Val Val Ser Leu Ser Leu Leu Glu Thr Leu Tyr Glu Met Lys Asp
100 105 110

Val Val Glu Val Tyr Ser Arg
115

<210> SEQ ID NO 13
<211> LENGTH: 2369
<212> TYPE: DNA
<213> ORGANISM: Influenza B virus

<400> SEQUENCE: 13
agcagaagcg gagcctttaa gatgaatata aatccttatt ttctcttcat agatgtaccc 60
atacaggcag caatttcaac aacattccca tacaccggtg ttcccccttta ttcccatgga 120 acgggaacag gctacacaat agacaccgtg atcagaacac atgagtactc gaacaaagga 180
aaacagtatg tttctgacat cacaggatgt acaatgatag atccaacaaa tgggccatta 240
cctgaagaca atgagccaag tgcctatgca caattagatt gcgttctgga ggctttggat 300
agaatggatg aggaacatcc aggtctgttt caagcagcct cacagaatgc catggaggca 360
ctaatggtca caactgtaga caaattaacc caggggagac agactttcga ttggacagta 420
tgcagaaacc agcctgctgc aacggcacta aacacaacaa taacctcctt cagattgaat 480
gatttgaatg gagctgacaa gggtggattg gtaccctttt gccaagatat cattgattca 540
ttagacaagc ctgaaatgac tttcttctca gtaaagaata taaagaaaaa attgcctgct 600
aaaaacagaa agggtttcct cataaagaga ataccaatga aagtaaaaga caggatatcc 660
agagtggaat acatcaaaag agcattgtca ttaaacacaa tgacaaaaga tgctgaaagg 720

```
ggcaaactaa aaagaagagc gattgcaacc gctggaatac aaatcagagg gtttgtatta    780

gtagttgaaa acttggctaa aaacatctgt gaaaatctag aacaaagtgg tttgcccgtg    840

ggtggaaatg aaaagaaggc caaactgtca aatgcagtgg ccaaaatgct cagtaactgc    900

ccaccaggag ggatcagcat gacagtaaca ggagacaata ctaaatggaa tgaatgctta    960

aatccacgaa tctttttggc tatgactgaa agaataacca gagacagccc aatttggttc   1020

cgggattttt gtagtatagc accggtcttg ttctccaaca aaatagccag attggggaaa   1080

ggatttatga taacaagtaa aacaaaaaga ctaaaggctc aaataccttg tcctgatctg   1140

ttcagcatac cattagaaag atataatgaa gaaacaaggg cgaaattaaa aaggctgaag   1200

ccattcttca atgaagaagg aacggcatct ttgtcgcctg ggatgatgat gggaatgttt   1260

aatatgctat ctaccgtgtt gggagtagca gcactaggca tcaaaaacat tggaaacaag   1320

gaatacttat gggatggact gcaatcttcc gatgattttg ctttgtttgt taatgcaaaa   1380

gatgaagaaa catgtatgga agggataaac gatttttacc gaacatgtaa attattggga   1440

ataaacatga gcaaaaagaa aagttactgt aacgaaactg gaatgtttga atttacaagc   1500

atgttctata gagatggatt tgtatctaac tttgcaatgg aaattccttc atttggagtt   1560

gctggagtaa atgaatcagc agatatggca ataggaatga caataataaa gaacaatatg   1620

attaacaatg ggatgggtcc agcaacagca caaacagcca tacaattgtt catagctgat   1680

tataggtaca catacaaatg ccacagagga gattccaaag tggaaggaaa aagaatgaaa   1740

attataaagg agctatggga aaacactaaa ggaagagatg gtctgttagt agcagatggt   1800

gggcccaaca tttacaattt gagaaactta catatcccag aaatagtatt gaagtacaac   1860

ctaatggacc ctgaatacaa agggcggtta cttcaccctc aaaatccctt tgtaggacat   1920

ttgtctattg aaggcatcaa agaagcagat ataaccccag cacatggtcc tgtgaggaaa   1980

atggattatg atgcagtgtc tggaactcat agttggagaa ccaaaaggaa cagatctata   2040

ctaaatactg atcagaggaa catgattctt gaagaacaat gctacgctaa atgttgcaat   2100

ctttttgagg cctgttttaa cagtgcatca tacaggaaac cagtagggca gcatagcatg   2160

cttgaggcta tggcccatag attaagaatg gatgcacgac tagattatga atcaggaaga   2220

atgtcaaagg atgattttga gaaagcaatg gctcaccttg gtgagattgg gtacacataa   2280

gctccgaaga tgtccatggg gttattggtc atcattggat acatgtgata aacaaatgat   2340

taaaatgaaa aaaggctcgt gtttctact                                    2369
```

```
<210> SEQ ID NO 14
<211> LENGTH: 752
<212> TYPE: PRT
<213> ORGANISM: Influenza B virus

<400> SEQUENCE: 14

Met Asn Ile Asn Pro Tyr Phe Leu Phe Ile Asp Val Pro Ile Gln Ala
1               5                   10                  15

Ala Ile Ser Thr Thr Phe Pro Tyr Thr Gly Val Pro Pro Tyr Ser His
            20                  25                  30

Gly Thr Gly Thr Gly Tyr Thr Ile Asp Thr Val Ile Arg Thr His Glu
        35                  40                  45

Tyr Ser Asn Lys Gly Lys Gln Tyr Val Ser Asp Ile Thr Gly Cys Thr
    50                  55                  60

Met Ile Asp Pro Thr Asn Gly Pro Leu Pro Glu Asp Asn Glu Pro Ser
65                  70                  75                  80
```

-continued

```
Ala Tyr Ala Gln Leu Asp Cys Val Leu Glu Ala Leu Asp Arg Met Asp
                85                  90                  95

Glu Glu His Pro Gly Leu Phe Gln Ala Ala Ser Gln Asn Ala Met Glu
            100                 105                 110

Ala Leu Met Val Thr Thr Val Asp Lys Leu Thr Gln Gly Arg Gln Thr
        115                 120                 125

Phe Asp Trp Thr Val Cys Arg Asn Gln Pro Ala Ala Thr Ala Leu Asn
    130                 135                 140

Thr Thr Ile Thr Ser Phe Arg Leu Asn Asp Leu Asn Gly Ala Asp Lys
145                 150                 155                 160

Gly Gly Leu Val Pro Phe Cys Gln Asp Ile Ile Asp Ser Leu Asp Lys
                165                 170                 175

Pro Glu Met Thr Phe Phe Ser Val Lys Asn Ile Lys Lys Lys Leu Pro
            180                 185                 190

Ala Lys Asn Arg Lys Gly Phe Leu Ile Lys Arg Ile Pro Met Lys Val
        195                 200                 205

Lys Asp Arg Ile Ser Arg Val Glu Tyr Ile Lys Arg Ala Leu Ser Leu
    210                 215                 220

Asn Thr Met Thr Lys Asp Ala Glu Arg Gly Lys Leu Lys Arg Arg Ala
225                 230                 235                 240

Ile Ala Thr Ala Gly Ile Gln Ile Arg Gly Phe Val Leu Val Val Glu
                245                 250                 255

Asn Leu Ala Lys Asn Ile Cys Glu Asn Leu Glu Gln Ser Gly Leu Pro
            260                 265                 270

Val Gly Gly Asn Glu Lys Lys Ala Lys Leu Ser Asn Ala Val Ala Lys
        275                 280                 285

Met Leu Ser Asn Cys Pro Pro Gly Gly Ile Ser Met Thr Val Thr Gly
    290                 295                 300

Asp Asn Thr Lys Trp Asn Glu Cys Leu Asn Pro Arg Ile Phe Leu Ala
305                 310                 315                 320

Met Thr Glu Arg Ile Thr Arg Asp Ser Pro Ile Trp Phe Arg Asp Phe
                325                 330                 335

Cys Ser Ile Ala Pro Val Leu Phe Ser Asn Lys Ile Ala Arg Leu Gly
            340                 345                 350

Lys Gly Phe Met Ile Thr Ser Lys Thr Lys Arg Leu Lys Ala Gln Ile
        355                 360                 365

Pro Cys Pro Asp Leu Phe Ser Ile Pro Leu Glu Arg Tyr Asn Glu Glu
    370                 375                 380

Thr Arg Ala Lys Leu Lys Arg Leu Lys Pro Phe Phe Asn Glu Glu Gly
385                 390                 395                 400

Thr Ala Ser Leu Ser Pro Gly Met Met Met Gly Met Phe Asn Met Leu
                405                 410                 415

Ser Thr Val Leu Gly Val Ala Ala Leu Gly Ile Lys Asn Ile Gly Asn
            420                 425                 430

Lys Glu Tyr Leu Trp Asp Gly Leu Gln Ser Ser Asp Asp Phe Ala Leu
        435                 440                 445

Phe Val Asn Ala Lys Asp Glu Glu Thr Cys Met Glu Gly Ile Asn Asp
    450                 455                 460

Phe Tyr Arg Thr Cys Lys Leu Leu Gly Ile Asn Met Ser Lys Lys Lys
465                 470                 475                 480

Ser Tyr Cys Asn Glu Thr Gly Met Phe Glu Phe Thr Ser Met Phe Tyr
                485                 490                 495

Arg Asp Gly Phe Val Ser Asn Phe Ala Met Glu Ile Pro Ser Phe Gly
```

-continued

```
            500                 505                 510

Val Ala Gly Val Asn Glu Ser Ala Asp Met Ala Ile Gly Met Thr Ile
        515                 520                 525

Ile Lys Asn Asn Met Ile Asn Asn Gly Met Gly Pro Ala Thr Ala Gln
    530                 535                 540

Thr Ala Ile Gln Leu Phe Ile Ala Asp Tyr Arg Tyr Thr Tyr Lys Cys
545                 550                 555                 560

His Arg Gly Asp Ser Lys Val Glu Gly Lys Arg Met Lys Ile Ile Lys
                565                 570                 575

Glu Leu Trp Glu Asn Thr Lys Gly Arg Asp Gly Leu Leu Val Ala Asp
            580                 585                 590

Gly Gly Pro Asn Ile Tyr Asn Leu Arg Asn Leu His Ile Pro Glu Ile
        595                 600                 605

Val Leu Lys Tyr Asn Leu Met Asp Pro Glu Tyr Lys Gly Arg Leu Leu
    610                 615                 620

His Pro Gln Asn Pro Phe Val Gly His Leu Ser Ile Glu Gly Ile Lys
625                 630                 635                 640

Glu Ala Asp Ile Thr Pro Ala His Gly Pro Val Arg Lys Met Asp Tyr
                645                 650                 655

Asp Ala Val Ser Gly Thr His Ser Trp Arg Thr Lys Arg Asn Arg Ser
            660                 665                 670

Ile Leu Asn Thr Asp Gln Arg Asn Met Ile Leu Glu Glu Gln Cys Tyr
        675                 680                 685

Ala Lys Cys Cys Asn Leu Phe Glu Ala Cys Phe Asn Ser Ala Ser Tyr
    690                 695                 700

Arg Lys Pro Val Gly Gln His Ser Met Leu Glu Ala Met Ala His Arg
705                 710                 715                 720

Leu Arg Met Asp Ala Arg Leu Asp Tyr Glu Ser Gly Arg Met Ser Lys
                725                 730                 735

Asp Asp Phe Glu Lys Ala Met Ala His Leu Gly Glu Ile Gly Tyr Thr
            740                 745                 750


<210> SEQ ID NO 15
<211> LENGTH: 2369
<212> TYPE: DNA
<213> ORGANISM: Artificial Sequence
<220> FEATURE:
<223> OTHER INFORMATION: PB1 D67N

<400> SEQUENCE: 15

agcagaagcg gagcctttaa gatgaatata aatccttatt ttctcttcat agatgtaccc      60

atacaggcag caatttcaac aacattccca tacaccggtg ttccccctta ttcccatgga     120

acgggaacag gctacacaat agacaccgtg atcagaacac atgagtactc gaacaaagga     180

aaacagtatg tttctgacat cacaggatgt acaatgataa atccaacaaa tgggccatta     240

cctgaagaca atgagccaag tgcctatgca caattagatt gcgttctgga ggctttggat     300

agaatggatg aggaacatcc aggtctgttt caagcagcct cacagaatgc catggaggca     360

ctaatggtca caactgtaga caaattaacc caggggagac agactttcga ttggacagta     420

tgcagaaacc agcctgctgc aacggcacta aacacaacaa taacctcctt cagattgaat     480

gatttgaatg gagctgacaa gggtggattg gtacccttttt gccaagatat cattgattca     540

ttagacaagc ctgaaatgac tttcttctca gtaaagaata taaagaaaaa attgcctgct     600

aaaaacagaa agggtttcct cataaagaga ataccaatga aagtaaaaga caggatatcc     660
```

-continued

```
agagtggaat acatcaaaag agcattgtca ttaaacacaa tgacaaaaga tgctgaaagg    720
ggcaaactaa aaagaagagc gattgcaacc gctggaatac aaatcagagg gtttgtatta    780
gtagttgaaa acttggctaa aaacatctgt gaaaatctag aacaaagtgg tttgcccgtg    840
ggtggaaatg aaaagaaggc caaactgtca aatgcagtgg ccaaaatgct cagtaactgc    900
ccaccaggag ggatcagcat gacagtaaca ggagacaata ctaaatggaa tgaatgctta    960
aatccacgaa tctttttggc tatgactgaa agaataacca gagacagccc aatttggttc   1020
cgggattttt gtagtatagc accggtcttg ttctccaaca aaatagccag attggggaaa   1080
ggatttatga taacaagtaa aacaaaaaga ctaaaggctc aaataccttg tcctgatctg   1140
ttcagcatac cattagaaag atataatgaa gaaacaaggg cgaaattaaa aaggctgaag   1200
ccattcttca atgaagaagg aacggcatct ttgtcgcctg ggatgatgat gggaatgttt   1260
aatatgctat ctaccgtgtt gggagtagca gcactaggca tcaaaaacat tggaaacaag   1320
gaatacttat gggatggact gcaatcttcc gatgattttg ctttgtttgt taatgcaaaa   1380
gatgaagaaa catgtatgga agggataaac gatttttacc gaacatgtaa attattggga   1440
ataaacatga gcaaaaagaa aagttactgt aacgaaactg gaatgtttga atttacaagc   1500
atgttctata gagatggatt tgtatctaac tttgcaatgg aaattccttc atttggagtt   1560
gctggagtaa atgaatcagc agatatggca ataggaatga caataataaa gaacaatatg   1620
attaacaatg ggatgggtcc agcaacagca caaacagcca tacaattgtt catagctgat   1680
tataggtaca catacaaatg ccacagagga gattccaaag tggaaggaaa aagaatgaaa   1740
attataaagg agctatggga aaacactaaa ggaagagatg gtctgttagt agcagatggt   1800
gggcccaaca tttacaattt gagaaactta catatcccag aaatagtatt gaagtacaac   1860
ctaatggacc ctgaatacaa agggcggtta cttcaccctc aaaatccctt tgtaggacat   1920
ttgtctattg aaggcatcaa agaagcagat ataaccccag cacatggtcc tgtgaggaaa   1980
atggattatg atgcagtgtc tggaactcat agttggagaa ccaaaaggaa cagatctata   2040
ctaaatactg atcagaggaa catgattctt gaagaacaat gctacgctaa atgttgcaat   2100
ctttttgagg cctgttttaa cagtgcatca tacaggaaac cagtagggca gcatagcatg   2160
cttgaggcta tggcccatag attaagaatg gatgcacgac tagattatga atcaggaaga   2220
atgtcaaagg atgattttga gaaagcaatg gctcaccttg gtgagattgg gtacacataa   2280
gctccgaaga tgtccatggg gttattggtc atcattggat acatgtgata aacaaatgat   2340
taaaatgaaa aaaggctcgt gtttctact                                    2369
```

<210> SEQ ID NO 16
<211> LENGTH: 752
<212> TYPE: PRT
<213> ORGANISM: Artificial Sequence
<220> FEATURE:
<223> OTHER INFORMATION: PB1 D67N

<400> SEQUENCE: 16

```
Met Asn Ile Asn Pro Tyr Phe Leu Phe Ile Asp Val Pro Ile Gln Ala
1               5                   10                  15

Ala Ile Ser Thr Thr Phe Pro Tyr Thr Gly Val Pro Pro Tyr Ser His
            20                  25                  30

Gly Thr Gly Thr Gly Tyr Thr Ile Asp Thr Val Ile Arg Thr His Glu
        35                  40                  45

Tyr Ser Asn Lys Gly Lys Gln Tyr Val Ser Asp Ile Thr Gly Cys Thr
    50                  55                  60
```

-continued

```
Met Ile Asn Pro Thr Asn Gly Pro Leu Pro Glu Asp Asn Glu Pro Ser
65                  70                  75                  80

Ala Tyr Ala Gln Leu Asp Cys Val Leu Glu Ala Leu Asp Arg Met Asp
                85                  90                  95

Glu Glu His Pro Gly Leu Phe Gln Ala Ala Ser Gln Asn Ala Met Glu
            100                 105                 110

Ala Leu Met Val Thr Thr Val Asp Lys Leu Thr Gln Gly Arg Gln Thr
        115                 120                 125

Phe Asp Trp Thr Val Cys Arg Asn Gln Pro Ala Ala Thr Ala Leu Asn
    130                 135                 140

Thr Thr Ile Thr Ser Phe Arg Leu Asn Asp Leu Asn Gly Ala Asp Lys
145                 150                 155                 160

Gly Gly Leu Val Pro Phe Cys Gln Asp Ile Ile Asp Ser Leu Asp Lys
                165                 170                 175

Pro Glu Met Thr Phe Phe Ser Val Lys Asn Ile Lys Lys Lys Leu Pro
            180                 185                 190

Ala Lys Asn Arg Lys Gly Phe Leu Ile Lys Arg Ile Pro Met Lys Val
        195                 200                 205

Lys Asp Arg Ile Ser Arg Val Glu Tyr Ile Lys Arg Ala Leu Ser Leu
    210                 215                 220

Asn Thr Met Thr Lys Asp Ala Glu Arg Gly Lys Leu Lys Arg Arg Ala
225                 230                 235                 240

Ile Ala Thr Ala Gly Ile Gln Ile Arg Gly Phe Val Leu Val Val Glu
                245                 250                 255

Asn Leu Ala Lys Asn Ile Cys Glu Asn Leu Glu Gln Ser Gly Leu Pro
            260                 265                 270

Val Gly Gly Asn Glu Lys Lys Ala Lys Leu Ser Asn Ala Val Ala Lys
        275                 280                 285

Met Leu Ser Asn Cys Pro Pro Gly Gly Ile Ser Met Thr Val Thr Gly
    290                 295                 300

Asp Asn Thr Lys Trp Asn Glu Cys Leu Asn Pro Arg Ile Phe Leu Ala
305                 310                 315                 320

Met Thr Glu Arg Ile Thr Arg Asp Ser Pro Ile Trp Phe Arg Asp Phe
                325                 330                 335

Cys Ser Ile Ala Pro Val Leu Phe Ser Asn Lys Ile Ala Arg Leu Gly
            340                 345                 350

Lys Gly Phe Met Ile Thr Ser Lys Thr Lys Arg Leu Lys Ala Gln Ile
        355                 360                 365

Pro Cys Pro Asp Leu Phe Ser Ile Pro Leu Glu Arg Tyr Asn Glu Glu
    370                 375                 380

Thr Arg Ala Lys Leu Lys Arg Leu Lys Pro Phe Phe Asn Glu Glu Gly
385                 390                 395                 400

Thr Ala Ser Leu Ser Pro Gly Met Met Met Gly Met Phe Asn Met Leu
                405                 410                 415

Ser Thr Val Leu Gly Val Ala Ala Leu Gly Ile Lys Asn Ile Gly Asn
            420                 425                 430

Lys Glu Tyr Leu Trp Asp Gly Leu Gln Ser Ser Asp Asp Phe Ala Leu
        435                 440                 445

Phe Val Asn Ala Lys Asp Glu Glu Thr Cys Met Glu Gly Ile Asn Asp
    450                 455                 460

Phe Tyr Arg Thr Cys Lys Leu Leu Gly Ile Asn Met Ser Lys Lys Lys
465                 470                 475                 480
```

-continued

Ser Tyr Cys Asn Glu Thr Gly Met Phe Glu Phe Thr Ser Met Phe Tyr
485 490 495

Arg Asp Gly Phe Val Ser Asn Phe Ala Met Glu Ile Pro Ser Phe Gly
500 505 510

Val Ala Gly Val Asn Glu Ser Ala Asp Met Ala Ile Gly Met Thr Ile
515 520 525

Ile Lys Asn Asn Met Ile Asn Asn Gly Met Gly Pro Ala Thr Ala Gln
530 535 540

Thr Ala Ile Gln Leu Phe Ile Ala Asp Tyr Arg Tyr Thr Tyr Lys Cys
545 550 555 560

His Arg Gly Asp Ser Lys Val Glu Gly Lys Arg Met Lys Ile Ile Lys
565 570 575

Glu Leu Trp Glu Asn Thr Lys Gly Arg Asp Gly Leu Leu Val Ala Asp
580 585 590

Gly Gly Pro Asn Ile Tyr Asn Leu Arg Asn Leu His Ile Pro Glu Ile
595 600 605

Val Leu Lys Tyr Asn Leu Met Asp Pro Glu Tyr Lys Gly Arg Leu Leu
610 615 620

His Pro Gln Asn Pro Phe Val Gly His Leu Ser Ile Glu Gly Ile Lys
625 630 635 640

Glu Ala Asp Ile Thr Pro Ala His Gly Pro Val Arg Lys Met Asp Tyr
645 650 655

Asp Ala Val Ser Gly Thr His Ser Trp Arg Thr Lys Arg Asn Arg Ser
660 665 670

Ile Leu Asn Thr Asp Gln Arg Asn Met Ile Leu Glu Glu Gln Cys Tyr
675 680 685

Ala Lys Cys Cys Asn Leu Phe Glu Ala Cys Phe Asn Ser Ala Ser Tyr
690 695 700

Arg Lys Pro Val Gly Gln His Ser Met Leu Glu Ala Met Ala His Arg
705 710 715 720

Leu Arg Met Asp Ala Arg Leu Asp Tyr Glu Ser Gly Arg Met Ser Lys
725 730 735

Asp Asp Phe Glu Lys Ala Met Ala His Leu Gly Glu Ile Gly Tyr Thr
740 745 750

<210> SEQ ID NO 17
<211> LENGTH: 32
<212> TYPE: PRT
<213> ORGANISM: Influenza B virus

<400> SEQUENCE: 17

Cys Gly Cys Ala Gly Thr Cys Gly Gly Thr Ala Cys Thr Thr Thr Thr
1 5 10 15

Thr Thr Thr Thr Thr Thr Thr Thr Thr Thr Thr Thr Thr Thr Val Asn
20 25 30

<210> SEQ ID NO 18
<211> LENGTH: 33
<212> TYPE: PRT
<213> ORGANISM: Influenza B virus

<400> SEQUENCE: 18

Ala Ala Gly Cys Ala Gly Thr Gly Gly Thr Ala Thr Cys Ala Ala Cys
1 5 10 15

Gly Cys Ala Gly Ala Gly Thr Ala Cys Gly Cys Arg Gly Arg Gly Arg
20 25 30

-continued

Gly

<210> SEQ ID NO 19
<211> LENGTH: 1190
<212> TYPE: DNA
<213> ORGANISM: Artificial Sequence
<220> FEATURE:
<223> OTHER INFORMATION: M1 K93R

<400> SEQUENCE: 19
agcagaagca cgcactttct taaaatgtcg ctgtttggag acacaattgc ctacctgctt 60
tcattgacag aagatggaga aggcaaagca gaactagcag aaaaattaca ctgttggttc 120
ggtgggaaag aatttgacct agactctgcc ttggaatgga taaaaaacaa aagatgctta 180
actgatatac agaaagcact aattggtgcc tctatctgct ttttaaaacc caaagaccag 240
gaaagaaaaa gaagattcat cacagagccc ctatcaggaa tgggaacaac agcaacaaaa 300
aggaagggcc tgattctagc tgagagaaaa atgagaaaat gtgtgagctt ccatgaagca 360
tttgaaatag cagaaggcca tgaaagctca gcgttactat attgtctcat ggtcatgtac 420
ctgaatcctg gaaattattc aatgcaagta aaactaggaa cgctctgtgc tttgtgcgaa 480
aaacaagcat cacattcaca cagggctcat agcagagcag cgagatcttc agtgcccgga 540
gtgagacggg aaatgcagat ggtctcagct atgaacacag caaaaacaat gaatggaatg 600
ggaaaaggag aagacgtcca aaaactggca gaagaactgc aaagcaacat tggagtattg 660
agatctcttg ggcaagtcca aaagaatggg gaaggaattg caaaggatgt aatggaagtg 720
ctaaagcaga gctctatggg aaattcagct cttgtgaaga aatacctata atgctcgaac 780
catttcagat tctttcaatt tgttctttta ttttatcagc tctccatttc atggcttgga 840
caataggaca tttaaatcaa ataaaaagag gagtaaacat gaaaatacga ataaaggggc 900
caaataaaga gacaataaac agagaggtat caattttgag acacagttac caaaaagaaa 960
tccaggctaa agaagcaatg aaggaagtac tctctgacaa catggaggta ttgagtgacc 1020
acatagtaat tgaggggctt tctgctgaag agataataaa aatgggtgaa acagttttgg 1080
aggtagaaga atttcattaa attcaatttt tactgtactt cttactatgc atttaagcaa 1140
attgtaatca atgtcagcaa ataaactgga aaaagtgcgt tgtttctact 1190

<210> SEQ ID NO 20
<211> LENGTH: 248
<212> TYPE: PRT
<213> ORGANISM: Artificial Sequence
<220> FEATURE:
<223> OTHER INFORMATION: M1 K93R

<400> SEQUENCE: 20

Met Ser Leu Phe Gly Asp Thr Ile Ala Tyr Leu Leu Ser Leu Thr Glu
1 5 10 15

Asp Gly Glu Gly Lys Ala Glu Leu Ala Glu Lys Leu His Cys Trp Phe
20 25 30

Gly Gly Lys Glu Phe Asp Leu Asp Ser Ala Leu Glu Trp Ile Lys Asn
35 40 45

Lys Arg Cys Leu Thr Asp Ile Gln Lys Ala Leu Ile Gly Ala Ser Ile
50 55 60

Cys Phe Leu Lys Pro Lys Asp Gln Glu Arg Lys Arg Arg Phe Ile Thr
65 70 75 80

Glu Pro Leu Ser Gly Met Gly Thr Thr Ala Thr Lys Arg Lys Gly Leu
85 90 95

-continued

```
Ile Leu Ala Glu Arg Lys Met Arg Lys Cys Val Ser Phe His Glu Ala
            100                 105                 110

Phe Glu Ile Ala Glu Gly His Glu Ser Ser Ala Leu Leu Tyr Cys Leu
        115                 120                 125

Met Val Met Tyr Leu Asn Pro Gly Asn Tyr Ser Met Gln Val Lys Leu
    130                 135                 140

Gly Thr Leu Cys Ala Leu Cys Glu Lys Gln Ala Ser His Ser His Arg
145                 150                 155                 160

Ala His Ser Arg Ala Ala Arg Ser Ser Val Pro Gly Val Arg Arg Glu
                165                 170                 175

Met Gln Met Val Ser Ala Met Asn Thr Ala Lys Thr Met Asn Gly Met
            180                 185                 190

Gly Lys Gly Glu Asp Val Gln Lys Leu Ala Glu Glu Leu Gln Ser Asn
        195                 200                 205

Ile Gly Val Leu Arg Ser Leu Gly Ala Ser Gln Lys Asn Gly Glu Gly
    210                 215                 220

Ile Ala Lys Asp Val Met Glu Val Leu Lys Gln Ser Ser Met Gly Asn
225                 230                 235                 240

Ser Ala Leu Val Lys Lys Tyr Leu
                245


<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21

cccactgctt actggcttat                                                  20


<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22

cagatggctg gcaactagaa                                                  20


<210> SEQ ID NO 23
<211> LENGTH: 442
<212> TYPE: DNA
<213> ORGANISM: Artificial Sequence
<220> FEATURE:
<223> OTHER INFORMATION: NS Y117H

<400> SEQUENCE: 23

agcagaagca gaggatttgt ttagtcactg gcaaacagga aaaatggcgg acaatatgac      60

cacaacacaa attgagtgga ggatgaagaa gatggccatc ggatcctcaa ttcactcttc     120

gagcgtctta atgaaggaca ttcaaagcca attcgagcag ctgaaactgc ggtgggagtc     180

ttatcccaat ttggtcaaga gcaccgatta tcaccagaag agggagacaa ttagactggt     240

cacggaagaa ctttatcttt taagtaaaag aattgatgat aacatattgt tccacaaaac     300

agtaatagct aacagctcca taatagctga catggttgta tcattatcat tattagaaac     360

attgtatgaa atgaaggatg tggttgaagt gcacagcagg cagtgcttgt gaatttaaaa     420
```

-continued taaaaatcct cttgttacta ct 442

<210> SEQ ID NO 24
<211> LENGTH: 119
<212> TYPE: PRT
<213> ORGANISM: Artificial Sequence
<220> FEATURE:
<223> OTHER INFORMATION: NS Y117H

<400> SEQUENCE: 24

Met Ala Asp Asn Met Thr Thr Thr Gln Ile Glu Trp Arg Met Lys Lys
1 5 10 15

Met Ala Ile Gly Ser Ser Ile His Ser Ser Ser Val Leu Met Lys Asp
20 25 30

Ile Gln Ser Gln Phe Glu Gln Leu Lys Leu Arg Trp Glu Ser Tyr Pro
35 40 45

Asn Leu Val Lys Ser Thr Asp Tyr His Gln Lys Arg Glu Thr Ile Arg
50 55 60

Leu Val Thr Glu Glu Leu Tyr Leu Leu Ser Lys Arg Ile Asp Asp Asn
65 70 75 80

Ile Leu Phe His Lys Thr Val Ile Ala Asn Ser Ser Ile Ile Ala Asp
85 90 95

Met Val Val Ser Leu Ser Leu Leu Glu Thr Leu Tyr Glu Met Lys Asp
100 105 110

Val Val Glu Val His Ser Arg
115

<210> SEQ ID NO 25
<211> LENGTH: 2341
<212> TYPE: DNA
<213> ORGANISM: Influenza A virus

<400> SEQUENCE: 25
agcgaaagca ggtcaattat attcaatatg gaaagaataa aagaactacg aaatctaatg 60
tcgcagtctc gcacccgcga gatactcaca aaaaccaccg tggaccatat ggccataatc 120
aagaagtaca catcaggaag acaggagaag aacccagcac ttaggatgaa atggatgatg 180
gcaatgaaat atccaattac agcagacaag aggataacgg aaatgattcc tgagagaaat 240
gagcaaggac aaactttatg gagtaaaatg aatgattccg gatcagaccg agtgatggta 300
tcacctctgg ctgtgacatg gtggaatagg aatggaccaa taacaaatac agttcattat 360
ccaaaaatct acaaaactta ttttgaaaga gtcgaaaggc taaagcatgg aacctttggc 420
cctgtccatt ttagaaacca agtcaaaata cgtcggagag ttgacataaa tcctggtcat 480
gcagatctca gtgccaagga ggcacaggat gtaatcatgg aagttgtttt ccctaacgaa 540
gtgggagcca ggatactaac atcggaatcg caactaacga taaccaaaga gaagaaagaa 600
gaactccagg attgcaaaat ttctcctttg atggttgcat acatgttgga gagagaactg 660
gtccgcaaaa cgagattcct cccagtggct ggtggaacaa gcagtgtgta cattgaagtg 720
ttgcatttga ctcaaggaac atgctgggaa cagatgtata ctccaggagg ggaagtgagg 780
aatgatgatg ttgatcaaag cttgattatt gctgctagga acatagtgag aagagctgca 840
gtatcagcag atccactagc atctttattg gagatgtgcc acagcacaca gattggtgga 900
attaggatgg tagacatcct taggcagaac ccaacagaag agcaagccgt ggatatatgc 960
aaggctgcaa tgggactgag aattagctca tccttcagtt ttggtggatt cacatttaag 1020
agaacaagcg gatcatcagt caagagagag gaagaggtgc ttacgggcaa tcttcaaaca 1080

-continued

```
ttgaagataa gagtgcatga gggatatgaa gagttcacaa tggttgggag aagagcaaca   1140
gccatactca gaaaagcaac caggagattg attcagctga tagtgagtgg gagagacgaa   1200
cagtcgattg ccgaagcaat aattgtggcc atggtatttt cacaagagga ttgtatgata   1260
aaagcagtca gaggtgatct gaatttcgtc aatagggcaa atcaacgatt gaatcctatg   1320
catcaacttt taagacattt tcagaaggat gcgaaagtgc tttttcaaaa ttggggagtt   1380
gaacctatcg acaatgtgat gggaatgatt gggatattgc ccgacatgac tccaagcatc   1440
gagatgtcaa tgagaggagt gagaatcagc aaaatgggtg tagatgagta ctccagcacg   1500
gagagggtag tggtgagcat tgaccgtttt ttgagaatcc gggaccaacg aggaaatgta   1560
ctactgtctc ccgaggaggt cagtgaaaca cagggaacag agaaactgac aataacttac   1620
tcatcgtcaa tgatgtggga gattaatggt cctgaatcag tgttggtcaa tacctatcaa   1680
tggatcatca gaaactggga aactgttaaa attcagtggt cccagaaccc tacaatgcta   1740
tacaataaaa tggaatttga accatttcag tctttagtac ctaaggccat tagaggccaa   1800
tacagtgggt ttgtaagaac tctgttccaa caaatgaggg atgtgcttgg gacatttgat   1860
accgcacaga taataaaact tcttcccttc gcagccgctc caccaaagca aagtagaatg   1920
cagttctcct catttactgt gaatgtgagg ggatcaggaa tgagaatact tgtaaggggc   1980
aattctcctg tattcaacta taacaaggcc acgaagagac tcacagttct cggaaaggat   2040
gctggcactt taactgaaga cccagatgaa ggcacagctg gagtggagtc cgctgttctg   2100
aggggattcc tcattctggg caaagaagac aagagatatg ggccagcact aagcatcaat   2160
gaactgagca accttgcgaa aggagagaag gctaatgtgc taattgggca aggagacgtg   2220
gtgttggtaa tgaaacggaa acgggactct agcatactta ctgacagcca gacagcgacc   2280
aaaagaattc ggatggccat caattagtgt cgaatagttt aaaaacgacc ttgtttctac   2340
t                                                                   2341
```

<210> SEQ ID NO 26
<211> LENGTH: 759
<212> TYPE: PRT
<213> ORGANISM: Influenza A virus

<400> SEQUENCE: 26

```
Met Glu Arg Ile Lys Glu Leu Arg Asn Leu Met Ser Gln Ser Arg Thr
1               5                   10                  15

Arg Glu Ile Leu Thr Lys Thr Thr Val Asp His Met Ala Ile Ile Lys
            20                  25                  30

Lys Tyr Thr Ser Gly Arg Gln Glu Lys Asn Pro Ala Leu Arg Met Lys
        35                  40                  45

Trp Met Met Ala Met Lys Tyr Pro Ile Thr Ala Asp Lys Arg Ile Thr
    50                  55                  60

Glu Met Ile Pro Glu Arg Asn Glu Gln Gly Gln Thr Leu Trp Ser Lys
65                  70                  75                  80

Met Asn Asp Ser Gly Ser Asp Arg Val Met Val Ser Pro Leu Ala Val
                85                  90                  95

Thr Trp Trp Asn Arg Asn Gly Pro Ile Thr Asn Thr Val His Tyr Pro
            100                 105                 110

Lys Ile Tyr Lys Thr Tyr Phe Glu Arg Val Glu Arg Leu Lys His Gly
        115                 120                 125

Thr Phe Gly Pro Val His Phe Arg Asn Gln Val Lys Ile Arg Arg Arg
    130                 135                 140
```

-continued

```
Val Asp Ile Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175

Leu Thr Ser Glu Ser Gln Leu Thr Ile Thr Lys Glu Lys Lys Glu Glu
            180                 185                 190

Leu Gln Asp Cys Lys Ile Ser Pro Leu Met Val Ala Tyr Met Leu Glu
        195                 200                 205

Arg Glu Leu Val Arg Lys Thr Arg Phe Leu Pro Val Ala Gly Gly Thr
    210                 215                 220

Ser Ser Val Tyr Ile Glu Val Leu His Leu Thr Gln Gly Thr Cys Trp
225                 230                 235                 240

Glu Gln Met Tyr Thr Pro Gly Gly Glu Val Arg Asn Asp Asp Val Asp
                245                 250                 255

Gln Ser Leu Ile Ile Ala Ala Arg Asn Ile Val Arg Arg Ala Ala Val
            260                 265                 270

Ser Ala Asp Pro Leu Ala Ser Leu Leu Glu Met Cys His Ser Thr Gln
        275                 280                 285

Ile Gly Gly Ile Arg Met Val Asp Ile Leu Arg Gln Asn Pro Thr Glu
    290                 295                 300

Glu Gln Ala Val Asp Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
                325                 330                 335

Ser Val Lys Arg Glu Glu Glu Val Leu Thr Gly Asn Leu Gln Thr Leu
            340                 345                 350

Lys Ile Arg Val His Glu Gly Tyr Glu Glu Phe Thr Met Val Gly Arg
        355                 360                 365

Arg Ala Thr Ala Ile Leu Arg Lys Ala Thr Arg Arg Leu Ile Gln Leu
    370                 375                 380

Ile Val Ser Gly Arg Asp Glu Gln Ser Ile Ala Glu Ala Ile Ile Val
385                 390                 395                 400

Ala Met Val Phe Ser Gln Glu Asp Cys Met Ile Lys Ala Val Arg Gly
                405                 410                 415

Asp Leu Asn Phe Val Asn Arg Ala Asn Gln Arg Leu Asn Pro Met His
            420                 425                 430

Gln Leu Leu Arg His Phe Gln Lys Asp Ala Lys Val Leu Phe Gln Asn
        435                 440                 445

Trp Gly Val Glu Pro Ile Asp Asn Val Met Gly Met Ile Gly Ile Leu
    450                 455                 460

Pro Asp Met Thr Pro Ser Ile Glu Met Ser Met Arg Gly Val Arg Ile
465                 470                 475                 480

Ser Lys Met Gly Val Asp Glu Tyr Ser Ser Thr Glu Arg Val Val Val
                485                 490                 495

Ser Ile Asp Arg Phe Leu Arg Ile Arg Asp Gln Arg Gly Asn Val Leu
            500                 505                 510

Leu Ser Pro Glu Glu Val Ser Glu Thr Gln Gly Thr Glu Lys Leu Thr
        515                 520                 525

Ile Thr Tyr Ser Ser Ser Met Met Trp Glu Ile Asn Gly Pro Glu Ser
    530                 535                 540

Val Leu Val Asn Thr Tyr Gln Trp Ile Ile Arg Asn Trp Glu Thr Val
545                 550                 555                 560
```

-continued

```
Lys Ile Gln Trp Ser Gln Asn Pro Thr Met Leu Tyr Asn Lys Met Glu
                565                 570                 575

Phe Glu Pro Phe Gln Ser Leu Val Pro Lys Ala Ile Arg Gly Gln Tyr
            580                 585                 590

Ser Gly Phe Val Arg Thr Leu Phe Gln Gln Met Arg Asp Val Leu Gly
        595                 600                 605

Thr Phe Asp Thr Ala Gln Ile Ile Lys Leu Leu Pro Phe Ala Ala Ala
    610                 615                 620

Pro Pro Lys Gln Ser Arg Met Gln Phe Ser Ser Phe Thr Val Asn Val
625                 630                 635                 640

Arg Gly Ser Gly Met Arg Ile Leu Val Arg Gly Asn Ser Pro Val Phe
                645                 650                 655

Asn Tyr Asn Lys Ala Thr Lys Arg Leu Thr Val Leu Gly Lys Asp Ala
            660                 665                 670

Gly Thr Leu Thr Glu Asp Pro Asp Glu Gly Thr Ala Gly Val Glu Ser
        675                 680                 685

Ala Val Leu Arg Gly Phe Leu Ile Leu Gly Lys Glu Asp Lys Arg Tyr
    690                 695                 700

Gly Pro Ala Leu Ser Ile Asn Glu Leu Ser Asn Leu Ala Lys Gly Glu
705                 710                 715                 720

Lys Ala Asn Val Leu Ile Gly Gln Gly Asp Val Val Leu Val Met Lys
                725                 730                 735

Arg Lys Arg Asp Ser Ser Ile Leu Thr Asp Ser Gln Thr Ala Thr Lys
            740                 745                 750

Arg Ile Arg Met Ala Ile Asn
        755
```

<210> SEQ ID NO 27
<211> LENGTH: 2341
<212> TYPE: DNA
<213> ORGANISM: Artificial Sequence
<220> FEATURE:
<223> OTHER INFORMATION: PB2 K80R

<400> SEQUENCE: 27

```
agcgaaagca ggtcaattat attcaatatg gaaagaataa aagaactacg aaatctaatg      60

tcgcagtctc gcacccgcga gatactcaca aaaaccaccg tggaccatat ggccataatc     120

aagaagtaca catcaggaag acaggagaag aacccagcac ttaggatgaa atggatgatg     180

gcaatgaaat atccaattac agcagacaag aggataacgg aaatgattcc tgagagaaat     240

gagcaaggac aaactttatg gagtagaatg aatgattccg gatcagaccg agtgatggta     300

tcacctctgg ctgtgacatg gtggaatagg aatggaccaa taacaaatac agttcattat     360

ccaaaaatct acaaaactta ttttgaaaga gtcgaaaggc taaagcatgg aacctttggc     420

cctgtccatt ttagaaacca agtcaaaata cgtcggagag ttgacataaa tcctggtcat     480

gcagatctca gtgccaagga ggcacaggat gtaatcatgg aagttgtttt ccctaacgaa     540

gtgggagcca ggatactaac atcggaatcg caactaacga taaccaaaga gaagaaagaa     600

gaactccagg attgcaaaat ttctcctttg atggttgcat acatgttgga gagagaactg     660

gtccgcaaaa cgagattcct cccagtggct ggtggaacaa gcagtgtgta cattgaagtg     720

ttgcatttga ctcaaggaac atgctgggaa cagatgtata ctccaggagg ggaagtgagg     780

aatgatgatg ttgatcaaag cttgattatt gctgctagga acatagtgag aagagctgca     840

gtatcagcag atccactagc atctttattg gagatgtgcc acagcacaca gattggtgga     900
```

-continued

```
attaggatgg tagacatcct taggcagaac ccaacagaag agcaagccgt ggatatatgc    960

aaggctgcaa tgggactgag aattagctca tccttcagtt ttggtggatt cacatttaag   1020

agaacaagcg gatcatcagt caagagagag gaagaggtgc ttacgggcaa tcttcaaaca   1080

ttgaagataa gagtgcatga gggatatgaa gagttcacaa tggttgggag aagagcaaca   1140

gccatactca gaaaagcaac caggagattg attcagctga tagtgagtgg gagagacgaa   1200

cagtcgattg ccgaagcaat aattgtggcc atggtatttt cacaagagga ttgtatgata   1260

aaagcagtca gaggtgatct gaatttcgtc aatagggcaa atcaacgatt gaatcctatg   1320

catcaacttt taagacattt tcagaaggat gcgaaagtgc tttttcaaaa ttggggagtt   1380

gaacctatcg acaatgtgat gggaatgatt gggatattgc ccgacatgac tccaagcatc   1440

gagatgtcaa tgagaggagt gagaatcagc aaaatgggtg tagatgagta ctccagcacg   1500

gagagggtag tggtgagcat tgaccgtttt ttgagaatcc gggaccaacg aggaaatgta   1560

ctactgtctc ccgaggaggt cagtgaaaca cagggaacag agaaactgac aataacttac   1620

tcatcgtcaa tgatgtggga gattaatggt cctgaatcag tgttggtcaa tacctatcaa   1680

tggatcatca gaaactggga aactgttaaa attcagtggt cccagaaccc tacaatgcta   1740

tacaataaaa tggaatttga accatttcag tctttagtac ctaaggccat tagaggccaa   1800

tacagtgggt ttgtaagaac tctgttccaa caaatgaggg atgtgcttgg gacatttgat   1860

accgcacaga taataaaact tcttcccttc gcagccgctc caccaaagca aagtagaatg   1920

cagttctcct catttactgt gaatgtgagg ggatcaggaa tgagaatact tgtaaggggc   1980

aattctcctg tattcaacta taacaaggcc acgaagagac tcacagttct cggaaaggat   2040

gctggcactt taactgaaga cccagatgaa ggcacagctg gagtggagtc cgctgttctg   2100

aggggattcc tcattctggg caaagaagac aagagatatg ggccagcact aagcatcaat   2160

gaactgagca accttgcgaa aggagagaag gctaatgtgc taattgggca aggagacgtg   2220

gtgttggtaa tgaaacggaa acgggactct agcatactta ctgacagcca gacagcgacc   2280

aaaagaattc ggatggccat caattagtgt cgaatagttt aaaaacgacc ttgtttctac   2340

t                                                                   2341
```

<210> SEQ ID NO 28
<211> LENGTH: 759
<212> TYPE: PRT
<213> ORGANISM: Artificial Sequence
<220> FEATURE:
<223> OTHER INFORMATION: PB2 K80R

<400> SEQUENCE: 28

```
Met Glu Arg Ile Lys Glu Leu Arg Asn Leu Met Ser Gln Ser Arg Thr
1               5                   10                  15

Arg Glu Ile Leu Thr Lys Thr Thr Val Asp His Met Ala Ile Ile Lys
            20                  25                  30

Lys Tyr Thr Ser Gly Arg Gln Glu Lys Asn Pro Ala Leu Arg Met Lys
        35                  40                  45

Trp Met Met Ala Met Lys Tyr Pro Ile Thr Ala Asp Lys Arg Ile Thr
    50                  55                  60

Glu Met Ile Pro Glu Arg Asn Glu Gln Gly Gln Thr Leu Trp Ser Arg
65                  70                  75                  80

Met Asn Asp Ser Gly Ser Asp Arg Val Met Val Ser Pro Leu Ala Val
                85                  90                  95

Thr Trp Trp Asn Arg Asn Gly Pro Ile Thr Asn Thr Val His Tyr Pro
```

-continued

```
            100                 105                 110

Lys Ile Tyr Lys Thr Tyr Phe Glu Arg Val Glu Arg Leu Lys His Gly
        115                 120                 125

Thr Phe Gly Pro Val His Phe Arg Asn Gln Val Lys Ile Arg Arg Arg
    130                 135                 140

Val Asp Ile Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175

Leu Thr Ser Glu Ser Gln Leu Thr Ile Thr Lys Glu Lys Lys Glu Glu
            180                 185                 190

Leu Gln Asp Cys Lys Ile Ser Pro Leu Met Val Ala Tyr Met Leu Glu
        195                 200                 205

Arg Glu Leu Val Arg Lys Thr Arg Phe Leu Pro Val Ala Gly Gly Thr
    210                 215                 220

Ser Ser Val Tyr Ile Glu Val Leu His Leu Thr Gln Gly Thr Cys Trp
225                 230                 235                 240

Glu Gln Met Tyr Thr Pro Gly Gly Glu Val Arg Asn Asp Asp Val Asp
                245                 250                 255

Gln Ser Leu Ile Ile Ala Ala Arg Asn Ile Val Arg Arg Ala Ala Val
            260                 265                 270

Ser Ala Asp Pro Leu Ala Ser Leu Leu Glu Met Cys His Ser Thr Gln
        275                 280                 285

Ile Gly Gly Ile Arg Met Val Asp Ile Leu Arg Gln Asn Pro Thr Glu
    290                 295                 300

Glu Gln Ala Val Asp Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
                325                 330                 335

Ser Val Lys Arg Glu Glu Glu Val Leu Thr Gly Asn Leu Gln Thr Leu
            340                 345                 350

Lys Ile Arg Val His Glu Gly Tyr Glu Glu Phe Thr Met Val Gly Arg
        355                 360                 365

Arg Ala Thr Ala Ile Leu Arg Lys Ala Thr Arg Arg Leu Ile Gln Leu
    370                 375                 380

Ile Val Ser Gly Arg Asp Glu Gln Ser Ile Ala Glu Ala Ile Ile Val
385                 390                 395                 400

Ala Met Val Phe Ser Gln Glu Asp Cys Met Ile Lys Ala Val Arg Gly
                405                 410                 415

Asp Leu Asn Phe Val Asn Arg Ala Asn Gln Arg Leu Asn Pro Met His
            420                 425                 430

Gln Leu Leu Arg His Phe Gln Lys Asp Ala Lys Val Leu Phe Gln Asn
        435                 440                 445

Trp Gly Val Glu Pro Ile Asp Asn Val Met Gly Met Ile Gly Ile Leu
    450                 455                 460

Pro Asp Met Thr Pro Ser Ile Glu Met Ser Met Arg Gly Val Arg Ile
465                 470                 475                 480

Ser Lys Met Gly Val Asp Glu Tyr Ser Ser Thr Glu Arg Val Val Val
                485                 490                 495

Ser Ile Asp Arg Phe Leu Arg Ile Arg Asp Gln Arg Gly Asn Val Leu
            500                 505                 510

Leu Ser Pro Glu Glu Val Ser Glu Thr Gln Gly Thr Glu Lys Leu Thr
        515                 520                 525
```

```
Ile Thr Tyr Ser Ser Ser Met Met Trp Glu Ile Asn Gly Pro Glu Ser
    530                 535                 540

Val Leu Val Asn Thr Tyr Gln Trp Ile Ile Arg Asn Trp Glu Thr Val
545                 550                 555                 560

Lys Ile Gln Trp Ser Gln Asn Pro Thr Met Leu Tyr Asn Lys Met Glu
                565                 570                 575

Phe Glu Pro Phe Gln Ser Leu Val Pro Lys Ala Ile Arg Gly Gln Tyr
            580                 585                 590

Ser Gly Phe Val Arg Thr Leu Phe Gln Gln Met Arg Asp Val Leu Gly
        595                 600                 605

Thr Phe Asp Thr Ala Gln Ile Ile Lys Leu Leu Pro Phe Ala Ala Ala
    610                 615                 620

Pro Pro Lys Gln Ser Arg Met Gln Phe Ser Ser Phe Thr Val Asn Val
625                 630                 635                 640

Arg Gly Ser Gly Met Arg Ile Leu Val Arg Gly Asn Ser Pro Val Phe
                645                 650                 655

Asn Tyr Asn Lys Ala Thr Lys Arg Leu Thr Val Leu Gly Lys Asp Ala
            660                 665                 670

Gly Thr Leu Thr Glu Asp Pro Asp Glu Gly Thr Ala Gly Val Glu Ser
        675                 680                 685

Ala Val Leu Arg Gly Phe Leu Ile Leu Gly Lys Glu Asp Lys Arg Tyr
    690                 695                 700

Gly Pro Ala Leu Ser Ile Asn Glu Leu Ser Asn Leu Ala Lys Gly Glu
705                 710                 715                 720

Lys Ala Asn Val Leu Ile Gly Gln Gly Asp Val Val Leu Val Met Lys
                725                 730                 735

Arg Lys Arg Asp Ser Ser Ile Leu Thr Asp Ser Gln Thr Ala Thr Lys
            740                 745                 750

Arg Ile Arg Met Ala Ile Asn
        755
```

<210> SEQ ID NO 29
<211> LENGTH: 2341
<212> TYPE: DNA
<213> ORGANISM: Influenza A virus

<400> SEQUENCE: 29

```
agcgaaagca ggcaaaccat ttgaatggat gtcaatccga ctttactttt cttgaaaatt      60

ccagcgcaaa atgccataag caccacattc ccttatactg gagatcctcc atacagccat     120

ggaacaggaa caggatacac catggacaca gttaacagaa cacatcaata ttcagaaaaa     180

gggaaatgga caacaaacac agaaactggg gcgccccaac ttaacccgat tgatggacca     240

ctacctgagg ataatgagcc aagtggatat gcacaaacag actgtgtcct ggaagctatg     300

gctttccttg aggaatccca cccagggatc tttgaaaact cgtgccttga aacaatggaa     360

gtcgttcaac aaacaagagt ggacagactg acccaaggtc gtcagaccta tgattggaca     420

ttaaacagaa atcaaccagc cgcaactgca ttagccaaca ctatagaagt tttcagatcg     480

aatggtctaa cagctaatga gtcgggaagg ctaatagatt tcctcaagga tgtgatggaa     540

tcaatggata aagaggaaat agagataaca acacacttcc aaagaaaaag aagagtaaga     600

gacaacatga ccaagaaaat ggtcacacaa agaacaatag gaaagaaaaa gcagagagtg     660

aacaagagaa gctatctaat aagagcatta actttgaaca caatgaccaa agatgcagaa     720

agaggtaaat taaagagaag agctattgca acacccggga tgcaaatcag agggttcgtg     780
```

-continued tactttgttg aaactctagc taggagcatt tgtgagaagc ttgaacagtc tggacttcca 840
gtaggaggta atgaaaagaa ggccaaactg gcaaatgttg tgagaaagat gatgactaat 900
tcacaagaca cagagctttc tttcacaatt actggagaca atactaagtg gaatgaaaat 960
caaaatcctc gaatgttcct ggcgatgatt acatatatca caaaaaatca acctgaatgg 1020
ttcagaaaca tcctgagcat cgcacccata atgttctcaa acaaaatggc gagactaggg 1080
aaaggataca tgttcgaaag taagagaatg aagctccgaa cacaaatacc agcagaaatg 1140
ctagcaagca ttgacctaaa gtatttcaat gaatcaacaa gaaagaaaat tgagaaaata 1200
aggcctcttc taatagatgg cacagcgtca ttgagccctg gaatgatgat gggcatgttc 1260
aacatgctaa gtacggtttt aggagtctca atactgaatc ttgggcaaaa gaaatacacc 1320
aaaacaacat actggtggga tggcttcaa tcctctgatg attttgctct catagtgaat 1380
gcaccaaatc atgagggaat acaagcagga gtggatagat tctacagaac ctgcaagcta 1440
gtcggaatca atatgagcaa gaagaagtcc tatataaata ggacaggaac atttgaattc 1500
acaagctttt tttatcgcta tggatttgtg gccaatttta gcatggagct gcccagtttt 1560
ggagtgtctg ggattaatga atcagctgat atgagcattg gagtaacagt gataaagaac 1620
aacatgataa acaatgacct tggaccagca acagcccaga tggctcttca actgttcatc 1680
aaggactaca gatatacata tcggtgccac agaggagaca cacaaattca gacgaggaga 1740
tcatttgagc taaagaagct gtgggagcaa acccgatcaa aggcaggact attggtttca 1800
gatggaggac cgaacttata caatatccgg aatcttcaca tccctgaagt ctgcttaaag 1860
tgggagctaa tggatgaaga ctatcaggga agactttgta atcccctgaa tccatttgtc 1920
agccataaag agattgagtc tgtaaacaat gctgtggtaa tgccagctca tggtccagcc 1980
aagagcatgg aatatgacgc tgttgcaact acacactcct ggattcccaa gaggaaccgc 2040
tctattctca acacaagcca aaggggaatt cttgaggatg aacagatgta tcagaagtgc 2100
tgcaacctgt tcgagaaatt tttccccagt agttcataca ggagaccggt tggaatttcc 2160
agcatggtgg aggccatggt gtctagggcc cggattgatg ccagaattga cttcgagtct 2220
ggacggatta agaaagaaga gttctccgag atcatgaaga tctgttccac cattgaagag 2280
ctcagacggc aaaaacaatg aatttagctt gtccttcatg aaaaaatgcc ttgtttctac 2340
t 2341

<210> SEQ ID NO 30
<211> LENGTH: 758
<212> TYPE: PRT
<213> ORGANISM: Influenza A virus

<400> SEQUENCE: 30

Met Asp Val Asn Pro Thr Leu Leu Phe Leu Lys Ile Pro Ala Gln Asn
1 5 10 15

Ala Ile Ser Thr Thr Phe Pro Tyr Thr Gly Asp Pro Pro Tyr Ser His
20 25 30

Gly Thr Gly Thr Gly Tyr Thr Met Asp Thr Val Asn Arg Thr His Gln
35 40 45

Tyr Ser Glu Lys Gly Lys Trp Thr Thr Asn Thr Glu Thr Gly Ala Pro
50 55 60

Gln Leu Asn Pro Ile Asp Gly Pro Leu Pro Glu Asp Asn Glu Pro Ser
65 70 75 80

Gly Tyr Ala Gln Thr Asp Cys Val Leu Glu Ala Met Ala Phe Leu Glu

-continued

```
                85                  90                  95

Gly Ser His Pro Gly Ile Phe Glu Asn Ser Cys Leu Glu Thr Met Glu
            100                 105                 110

Val Val Gln Gln Thr Arg Val Asp Arg Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Gly Leu Thr Ala Asn Glu Ser
145                 150                 155                 160

Gly Arg Leu Ile Asp Phe Leu Lys Asp Val Met Glu Ser Met Asp Lys
                165                 170                 175

Glu Glu Ile Glu Ile Thr Thr His Phe Gln Arg Lys Arg Arg Val Arg
            180                 185                 190

Asp Asn Met Thr Lys Lys Met Val Thr Gln Arg Thr Ile Gly Lys Lys
        195                 200                 205

Lys Gln Arg Val Asn Lys Arg Ser Tyr Leu Ile Arg Ala Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Ser Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285

Met Met Thr Asn Ser Gln Asp Thr Glu Leu Ser Phe Thr Ile Thr Gly
    290                 295                 300

Asp Asn Thr Lys Trp Asn Glu Asn Gln Asn Pro Arg Met Phe Leu Ala
305                 310                 315                 320

Met Ile Thr Tyr Ile Thr Lys Asn Gln Pro Glu Trp Phe Arg Asn Ile
                325                 330                 335

Leu Ser Ile Ala Pro Ile Met Phe Ser Asn Lys Met Ala Arg Leu Gly
            340                 345                 350

Lys Gly Tyr Met Phe Glu Ser Lys Arg Met Lys Leu Arg Thr Gln Ile
        355                 360                 365

Pro Ala Glu Met Leu Ala Ser Ile Asp Leu Lys Tyr Phe Asn Glu Ser
    370                 375                 380

Thr Arg Lys Lys Ile Glu Lys Ile Arg Pro Leu Leu Ile Asp Gly Thr
385                 390                 395                 400

Ala Ser Leu Ser Pro Gly Met Met Met Gly Met Phe Asn Met Leu Ser
                405                 410                 415

Thr Val Leu Gly Val Ser Ile Leu Asn Leu Gly Gln Lys Lys Tyr Thr
            420                 425                 430

Lys Thr Thr Tyr Trp Trp Asp Gly Leu Gln Ser Ser Asp Asp Phe Ala
        435                 440                 445

Leu Ile Val Asn Ala Pro Asn His Glu Gly Ile Gln Ala Gly Val Asp
    450                 455                 460

Arg Phe Tyr Arg Thr Cys Lys Leu Val Gly Ile Asn Met Ser Lys Lys
465                 470                 475                 480

Lys Ser Tyr Ile Asn Arg Thr Gly Thr Phe Glu Phe Thr Ser Phe Phe
                485                 490                 495

Tyr Arg Tyr Gly Phe Val Ala Asn Phe Ser Met Glu Leu Pro Ser Phe
            500                 505                 510
```

```
Gly Val Ser Gly Ile Asn Glu Ser Ala Asp Met Ser Ile Gly Val Thr
        515                 520                 525

Val Ile Lys Asn Asn Met Ile Asn Asn Asp Leu Gly Pro Ala Thr Ala
    530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Leu
                565                 570                 575

Lys Lys Leu Trp Glu Gln Thr Arg Ser Lys Ala Gly Leu Leu Val Ser
            580                 585                 590

Asp Gly Gly Pro Asn Leu Tyr Asn Ile Arg Asn Leu His Ile Pro Glu
        595                 600                 605

Val Cys Leu Lys Trp Glu Leu Met Asp Glu Asp Tyr Gln Gly Arg Leu
    610                 615                 620

Cys Asn Pro Leu Asn Pro Phe Val Ser His Lys Glu Ile Glu Ser Val
625                 630                 635                 640

Asn Asn Ala Val Val Met Pro Ala His Gly Pro Ala Lys Ser Met Glu
                645                 650                 655

Tyr Asp Ala Val Ala Thr Thr His Ser Trp Ile Pro Lys Arg Asn Arg
            660                 665                 670

Ser Ile Leu Asn Thr Ser Gln Arg Gly Ile Leu Glu Asp Glu Gln Met
        675                 680                 685

Tyr Gln Lys Cys Cys Asn Leu Phe Glu Lys Phe Phe Pro Ser Ser Ser
    690                 695                 700

Tyr Arg Arg Pro Val Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                725                 730                 735

Lys Glu Glu Phe Ser Glu Ile Met Lys Ile Cys Ser Thr Ile Glu Glu
            740                 745                 750

Leu Arg Arg Gln Lys Gln
        755
```

<210> SEQ ID NO 31
<211> LENGTH: 2341
<212> TYPE: DNA
<213> ORGANISM: Artificial Sequence
<220> FEATURE:
<223> OTHER INFORMATION: PB1 E97G S678N

<400> SEQUENCE: 31

```
agcgaaagca ggcaaaccat ttgaatggat gtcaatccga ctttactttt cttgaaaatt      60

ccagcgcaaa atgccataag caccacattc ccttatactg gagatcctcc atacagccat     120

ggaacaggaa caggatacac catggacaca gttaacagaa cacatcaata ttcagaaaaa     180

gggaaatgga caacaaacac agaaactggg gcgccccaac ttaacccgat tgatggacca     240

ctacctgagg ataatgagcc aagtggatat gcacaaacag actgtgtcct ggaagctatg     300

gctttccttg agggatccca cccagggatc tttgaaaact cgtgccttga aacaatggaa     360

gtcgttcaac aaacaagagt ggacagactg acccaaggtc gtcagaccta tgattggaca     420

ttaaacagaa atcaaccagc cgcaactgca ttagccaaca ctatagaagt tttcagatcg     480

aatggtctaa cagctaatga gtcgggaagg ctaatagatt tcctcaagga tgtgatggaa     540

tcaatggata aagaggaaat agagataaca acacacttcc aaagaaaaag aagagtaaga     600
```

-continued gacaacatga ccaagaaaat ggtcacacaa agaacaatag gaaagaaaaa gcagagagtg 660
aacaagagaa gctatctaat aagagcatta actttgaaca caatgaccaa agatgcagaa 720
agaggtaaat taaagagaag agctattgca acacccggga tgcaaatcag agggttcgtg 780
tactttgttg aaactctagc taggagcatt tgtgagaagc ttgaacagtc tggacttcca 840
gtaggaggta atgaaaagaa ggccaaactg gcaaatgttg tgagaaagat gatgactaat 900
tcacaagaca cagagctttc tttcacaatt actggagaca atactaagtg gaatgaaaat 960
caaaatcctc gaatgttcct ggcgatgatt acatatatca caaaaaatca acctgaatgg 1020
ttcagaaaca tcctgagcat cgcacccata atgttctcaa acaaaatggc gagactaggg 1080
aaaggataca tgttcgaaag taagagaatg aagctccgaa cacaaatacc agcagaaatg 1140
ctagcaagca ttgacctaaa gtatttcaat gaatcaacaa gaaagaaaat tgagaaaata 1200
aggcctcttc taatagatgg cacagcgtca ttgagccctg gaatgatgat gggcatgttc 1260
aacatgctaa gtacggtttt aggagtctca atactgaatc ttgggcaaaa gaaatacacc 1320
aaaacaacat actggtggga tggcttcaa tcctctgatg attttgctct catagtgaat 1380
gcaccaaatc atgagggaat acaagcagga gtggatagat tctacagaac ctgcaagcta 1440
gtcggaatca atatgagcaa gaagaagtcc tatataaata ggacaggaac atttgaattc 1500
acaagctttt tttatcgcta tggatttgtg gccaatttta gcatggagct gcccagtttt 1560
ggagtgtctg ggattaatga atcagctgat atgagcattg gagtaacagt gataaagaac 1620
aacatgataa acaatgacct tggaccagca acagcccaga tggctcttca actgttcatc 1680
aaggactaca gatatacata tcggtgccac agaggagaca cacaaattca gacgaggaga 1740
tcatttgagc taaagaagct gtgggagcaa acccgatcaa aggcaggact attggtttca 1800
gatggaggac cgaacttata caatatccgg aatcttcaca tccctgaagt ctgcttaaag 1860
tgggagctaa tggatgaaga ctatcaggga agactttgta atcccctgaa tccatttgtc 1920
agccataaag agattgagtc tgtaaacaat gctgtggtaa tgccagctca tggtccagcc 1980
aagagcatgg aatatgacgc tgttgcaact acacactcct ggattcccaa gaggaaccgc 2040
tctattctca acacaaacca aaggggaatt cttgaggatg aacagatgta tcagaagtgc 2100
tgcaacctgt tcgagaaatt tttccccagt agttcataca ggagaccggt tggaatttcc 2160
agcatggtgg aggccatggt gtctagggcc cggattgatg ccagaattga cttcgagtct 2220
ggacggatta agaaagaaga gttctccgag atcatgaaga tctgttccac cattgaagag 2280
ctcagacggc aaaaacaatg aatttagctt gtccttcatg aaaaaatgcc ttgtttctac 2340
t 2341

<210> SEQ ID NO 32
<211> LENGTH: 758
<212> TYPE: PRT
<213> ORGANISM: Artificial Sequence
<220> FEATURE:
<223> OTHER INFORMATION: PB1 E97G S678N

<400> SEQUENCE: 32

Met Asp Val Asn Pro Thr Leu Leu Phe Leu Lys Ile Pro Ala Gln Asn
1               5                   10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
        35                  40                  45

-continued

```
Tyr Ser Glu Lys Gly Lys Trp Thr Thr Asn Thr Glu Thr Gly Ala Pro
    50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Gly
                85                  90                  95

Gly Ser His Pro Gly Ile Phe Glu Asn Ser Cys Leu Glu Thr Met Glu
            100                 105                 110

Val Val Gln Gln Thr Arg Val Asp Arg Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Gly Leu Thr Ala Asn Glu Ser
145                 150                 155                 160

Gly Arg Leu Ile Asp Phe Leu Lys Asp Val Met Glu Ser Met Asp Lys
                165                 170                 175

Glu Glu Ile Glu Ile Thr Thr His Phe Gln Arg Lys Arg Arg Val Arg
            180                 185                 190

Asp Asn Met Thr Lys Lys Met Val Thr Gln Arg Thr Ile Gly Lys Lys
        195                 200                 205

Lys Gln Arg Val Asn Lys Arg Ser Tyr Leu Ile Arg Ala Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Ser Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285

Met Met Thr Asn Ser Gln Asp Thr Glu Leu Ser Phe Thr Ile Thr Gly
    290                 295                 300

Asp Asn Thr Lys Trp Asn Glu Asn Gln Asn Pro Arg Met Phe Leu Ala
305                 310                 315                 320

Met Ile Thr Tyr Ile Thr Lys Asn Gln Pro Glu Trp Phe Arg Asn Ile
                325                 330                 335

Leu Ser Ile Ala Pro Ile Met Phe Ser Asn Lys Met Ala Arg Leu Gly
            340                 345                 350

Lys Gly Tyr Met Phe Glu Ser Lys Arg Met Lys Leu Arg Thr Gln Ile
        355                 360                 365

Pro Ala Glu Met Leu Ala Ser Ile Asp Leu Lys Tyr Phe Asn Glu Ser
    370                 375                 380

Thr Arg Lys Lys Ile Glu Lys Ile Arg Pro Leu Leu Ile Asp Gly Thr
385                 390                 395                 400

Ala Ser Leu Ser Pro Gly Met Met Met Gly Met Phe Asn Met Leu Ser
                405                 410                 415

Thr Val Leu Gly Val Ser Ile Leu Asn Leu Gly Gln Lys Lys Tyr Thr
            420                 425                 430

Lys Thr Thr Tyr Trp Trp Asp Gly Leu Gln Ser Ser Asp Asp Phe Ala
        435                 440                 445

Leu Ile Val Asn Ala Pro Asn His Glu Gly Ile Gln Ala Gly Val Asp
    450                 455                 460

Arg Phe Tyr Arg Thr Cys Lys Leu Val Gly Ile Asn Met Ser Lys Lys
```

465 470 475 480

Lys Ser Tyr Ile Asn Arg Thr Gly Thr Phe Glu Phe Thr Ser Phe Phe
485 490 495

Tyr Arg Tyr Gly Phe Val Ala Asn Phe Ser Met Glu Leu Pro Ser Phe
500 505 510

Gly Val Ser Gly Ile Asn Glu Ser Ala Asp Met Ser Ile Gly Val Thr
515 520 525

Val Ile Lys Asn Asn Met Ile Asn Asn Asp Leu Gly Pro Ala Thr Ala
530 535 540

Gln Met Ala Leu Gln Leu Phe Ile Lys Asp Tyr Arg Tyr Thr Tyr Arg
545 550 555 560

Cys His Arg Gly Asp Thr Gln Ile Gln Thr Arg Arg Ser Phe Glu Leu
565 570 575

Lys Lys Leu Trp Glu Gln Thr Arg Ser Lys Ala Gly Leu Leu Val Ser
580 585 590

Asp Gly Gly Pro Asn Leu Tyr Asn Ile Arg Asn Leu His Ile Pro Glu
595 600 605

Val Cys Leu Lys Trp Glu Leu Met Asp Glu Asp Tyr Gln Gly Arg Leu
610 615 620

Cys Asn Pro Leu Asn Pro Phe Val Ser His Lys Glu Ile Glu Ser Val
625 630 635 640

Asn Asn Ala Val Val Met Pro Ala His Gly Pro Ala Lys Ser Met Glu
645 650 655

Tyr Asp Ala Val Ala Thr Thr His Ser Trp Ile Pro Lys Arg Asn Arg
660 665 670

Ser Ile Leu Asn Thr Asn Gln Arg Gly Ile Leu Glu Asp Glu Gln Met
675 680 685

Tyr Gln Lys Cys Cys Asn Leu Phe Glu Lys Phe Phe Pro Ser Ser Ser
690 695 700

Tyr Arg Arg Pro Val Gly Ile Ser Ser Met Val Glu Ala Met Val Ser
705 710 715 720

Arg Ala Arg Ile Asp Ala Arg Ile Asp Phe Glu Ser Gly Arg Ile Lys
725 730 735

Lys Glu Glu Phe Ser Glu Ile Met Lys Ile Cys Ser Thr Ile Glu Glu
740 745 750

Leu Arg Arg Gln Lys Gln
755

<210> SEQ ID NO 33
<211> LENGTH: 442
<212> TYPE: DNA
<213> ORGANISM: Artificial Sequence
<220> FEATURE:
<223> OTHER INFORMATION: NS2 NS2 R76G

<400> SEQUENCE: 33
agcagaagca gaggatttgt ttagtcactg gcaaacagga aaaatggcgg acaatatgac 60
cacaacacaa attgagtgga ggatgaagaa gatggccatc ggatcctcaa ttcactcttc 120
gagcgtctta atgaaggaca ttcaaagcca attcgagcag ctgaaactgc ggtgggagtc 180
ttatcccaat ttggtcaaga gcaccgatta tcaccagaag agggagacaa ttagactggt 240
cacggaagaa ctttatcttt taagtaaagg aattgatgat aacatattgt tccacaaaac 300
agtaatagct aacagctcca taatagctga catggttgta tcattatcat tattagaaac 360
attgtatgaa atgaaggatg tggttgaagt gtacagcagg cagtgcttgt gaatttaaaa 420
taaaaatcct cttgttacta ct 442

<210> SEQ ID NO 34
<211> LENGTH: 119
<212> TYPE: PRT
<213> ORGANISM: Artificial Sequence
<220> FEATURE:
<223> OTHER INFORMATION: NS2 NS2 R76G

<400> SEQUENCE: 34

Met Ala Asp Asn Met Thr Thr Thr Gln Ile Glu Trp Arg Met Lys Lys
1 5 10 15

Met Ala Ile Gly Ser Ser Ile His Ser Ser Ser Val Leu Met Lys Asp
20 25 30

Ile Gln Ser Gln Phe Glu Gln Leu Lys Leu Arg Trp Glu Ser Tyr Pro
35 40 45

Asn Leu Val Lys Ser Thr Asp Tyr His Gln Lys Arg Glu Thr Ile Arg
50 55 60

Leu Val Thr Glu Glu Leu Tyr Leu Leu Ser Lys Gly Ile Asp Asp Asn
65 70 75 80

Ile Leu Phe His Lys Thr Val Ile Ala Asn Ser Ser Ile Ile Ala Asp
85 90 95

Met Val Val Ser Leu Ser Leu Leu Glu Thr Leu Tyr Glu Met Lys Asp
100 105 110

Val Val Glu Val Tyr Ser Arg
115

<210> SEQ ID NO 35
<211> LENGTH: 1716
<212> TYPE: DNA
<213> ORGANISM: Artificial Sequence
<220> FEATURE:
<223> OTHER INFORMATION: PB1 E97G

<400> SEQUENCE: 35
cacaaagaac aataggaaag aaaaagcaga gagtgaacaa gagaagctat ctaataagag 60
cattaacttt gaacacaatg accaaagatg cagaaagagg taaattaaag agaagagcta 120
ttgcaacacc cgggatgcaa atcagagggt tcgtgtactt tgttgaaact ctagctagga 180
gcatttgtga gaagcttgaa cagtctggac ttccagtagg aggtaatgaa aagaaggcca 240
aactggcaaa tgttgtgaga aagatgatga ctaattcaca agacacagag ctttctttca 300
caattactgg agacaatact aagtggaatg aaaatcaaaa tcctcgaatg ttcctggcga 360
tgattacata tatcacaaaa aatcaacctg aatggttcag aaacatcctg agcatcgcac 420
ccataatgtt ctcaaacaaa atggcgagac tagggaaagg atacatgttc gaaagtaaga 480
gaatgaagct ccgaacacaa ataccagcag aaatgctagc aagcattgac ctaaagtatt 540
tcaatgaatc aacaagaaag aaaattgaga aaataaggcc tcttctaata gatggcacag 600
cgtcattgag ccctggaatg atgatgggca tgttcaacat gctaagtacg gttttaggag 660
tctcaatact gaatcttggg caaaagaaat acaccaaaac aacatactgg tgggatgggc 720
ttcaatcctc tgatgatttt gctctcatag tgaatgcacc aaatcatgag ggaatacaag 780
caggagtgga tagattctac agaacctgca agctagtcgg aatcaatatg agcaagaaga 840
agtcctatat aaataggaca ggaacatttg aattcacaag ctttttttat cgctatggat 900
ttgtggccaa ttttagcatg gagctgccca gttttggagt gtctgggatt aatgaatcag 960

```
ctgatatgag cattggagta acagtgataa agaacaacat gataaacaat gaccttggac   1020

cagcaacagc ccagatggct cttcaactgt tcatcaagga ctacagatat acatatcggt   1080

gccacagagg agacacacaa attcagacga ggagatcatt tgagctaaag aagctgtggg   1140

agcaaacccg atcaaaggca ggactattgg tttcagatgg aggaccgaac ttatacaata   1200

tccggaatct tcacatccct gaagtctgct taaagtggga gctaatggat gaagactatc   1260

agggaagact ttgtaatccc ctgaatccat ttgtcagcca taaagagatt gagtctgtaa   1320

acaatgctgt ggtaatgcca gctcatggtc cagccaagag catggaatat gacgctgttg   1380

caactacaca ctcctggatt cccaagagga accgctctat tctcaacaca agccaaaggg   1440

gaattcttga ggatgaacag atgtatcaga agtgctgcaa cctgttcgag aaatttttcc   1500

ccagtagttc atacaggaga ccggttggaa tttccagcat ggtggaggcc atggtgtcta   1560

gggcccggat tgatgccaga attgacttcg agtctggacg gattaagaaa gaagagttct   1620

ccgagatcat gaagatctgt tccaccattg aagagctcag acggcaaaaa caatgaattt   1680

agcttgtcct tcatgaaaaa atgccttgtt tctact                             1716
```

<210> SEQ ID NO 36
<211> LENGTH: 2341
<212> TYPE: DNA
<213> ORGANISM: Artificial Sequence
<220> FEATURE:
<223> OTHER INFORMATION: PB1 S678N

<400> SEQUENCE: 36

```
agcgaaagca ggcaaaccat ttgaatggat gtcaatccga ctttactttt cttgaaaatt     60

ccagcgcaaa atgccataag caccacattc ccttatactg gagatcctcc atacagccat    120

ggaacaggaa caggatacac catggacaca gttaacagaa cacatcaata ttcagaaaaa    180

gggaaatgga caacaaacac agaaactggg gcgccccaac ttaacccgat tgatggacca    240

ctacctgagg ataatgagcc aagtggatat gcacaaacag actgtgtcct ggaagctatg    300

gctttccttg aggaatccca cccagggatc tttgaaaact cgtgccttga aacaatggaa    360

gtcgttcaac aaacaagagt ggacagactg acccaaggtc gtcagaccta tgattggaca    420

ttaaacagaa atcaaccagc cgcaactgca ttagccaaca ctatagaagt tttcagatcg    480

aatggtctaa cagctaatga gtcgggaagg ctaatagatt tcctcaagga tgtgatggaa    540

tcaatggata aagaggaaat agagataaca acacacttcc aaagaaaaag aagagtaaga    600

gacaacatga ccaagaaaat ggtcacacaa agaacaatag gaaagaaaaa gcagagagtg    660

aacaagagaa gctatctaat aagagcatta actttgaaca caatgaccaa agatgcagaa    720

agaggtaaat taaagagaag agctattgca acacccggga tgcaaatcag agggttcgtg    780

tactttgttg aaactctagc taggagcatt tgtgagaagc ttgaacagtc tggacttcca    840

gtaggaggta atgaaaagaa ggccaaactg gcaaatgttg tgagaaagat gatgactaat    900

tcacaagaca cagagctttc tttcacaatt actggagaca atactaagtg gaatgaaaat    960

caaaatcctc gaatgttcct ggcgatgatt acatatatca caaaaaatca acctgaatgg   1020

ttcagaaaca tcctgagcat cgcacccata atgttctcaa acaaaatggc gagactaggg   1080

aaaggataca tgttcgaaag taagagaatg aagctccgaa cacaaatacc agcagaaatg   1140

ctagcaagca ttgacctaaa gtatttcaat gaatcaacaa gaaagaaaat tgagaaaata   1200

aggcctcttc taatagatgg cacagcgtca ttgagccctg gaatgatgat gggcatgttc   1260

aacatgctaa gtacggtttt aggagtctca atactgaatc ttgggcaaaa gaaatacacc   1320
```

aaaacaacat actggtggga tgggcttcaa tcctctgatg attttgctct catagtgaat 1380
gcaccaaatc atgagggaat acaagcagga gtggatagat tctacagaac ctgcaagcta 1440
gtcggaatca atatgagcaa gaagaagtcc tatataaata ggacaggaac atttgaattc 1500
acaagctttt tttatcgcta tggatttgtg gccaatttta gcatggagct gcccagtttt 1560
ggagtgtctg ggattaatga atcagctgat atgagcattg gagtaacagt gataaagaac 1620
aacatgataa acaatgacct tggaccagca acagcccaga tggctcttca actgttcatc 1680
aaggactaca gatatacata tcggtgccac agaggagaca cacaaattca gacgaggaga 1740
tcatttgagc taaagaagct gtgggagcaa acccgatcaa aggcaggact attggtttca 1800
gatggaggac cgaacttata caatatccgg aatcttcaca tccctgaagt ctgcttaaag 1860
tgggagctaa tggatgaaga ctatcaggga agactttgta atcccctgaa tccatttgtc 1920
agccataaag agattgagtc tgtaaacaat gctgtggtaa tgccagctca tggtccagcc 1980
aagagcatgg aatatgacgc tgttgcaact acacactcct ggattcccaa gaggaaccgc 2040
tctattctca acacaaacca aaggggaatt cttgaggatg aacagatgta tcagaagtgc 2100
tgcaacctgt tcgagaaatt tttccccagt agttcataca ggagaccggt tggaatttcc 2160
agcatggtgg aggccatggt gtctagggcc cggattgatg ccagaattga cttcgagtct 2220
ggacggatta agaaagaaga gttctccgag atcatgaaga tctgttccac cattgaagag 2280
ctcagacggc aaaaacaatg aatttagctt gtccttcatg aaaaaatgcc ttgtttctac 2340
t 2341

<210> SEQ ID NO 37
<211> LENGTH: 758
<212> TYPE: PRT
<213> ORGANISM: Artificial Sequence
<220> FEATURE:
<223> OTHER INFORMATION: PB1 E97G

<400> SEQUENCE: 37

Met Asp Val Asn Pro Thr Leu Leu Phe Leu Lys Ile Pro Ala Gln Asn
1 5 10 15

Ala Ile Ser Thr Thr Phe Pro Tyr Thr Gly Asp Pro Pro Tyr Ser His
20 25 30

Gly Thr Gly Thr Gly Tyr Thr Met Asp Thr Val Asn Arg Thr His Gln
35 40 45

Tyr Ser Glu Lys Gly Lys Trp Thr Thr Asn Thr Glu Thr Gly Ala Pro
50 55 60

Gln Leu Asn Pro Ile Asp Gly Pro Leu Pro Glu Asp Asn Glu Pro Ser
65 70 75 80

Gly Tyr Ala Gln Thr Asp Cys Val Leu Glu Ala Met Ala Phe Leu Gly
85 90 95

Gly Ser His Pro Gly Ile Phe Glu Asn Ser Cys Leu Glu Thr Met Glu
100 105 110

Val Val Gln Gln Thr Arg Val Asp Arg Leu Thr Gln Gly Arg Gln Thr
115 120 125

Tyr Asp Trp Thr Leu Asn Arg Asn Gln Pro Ala Ala Thr Ala Leu Ala
130 135 140

Asn Thr Ile Glu Val Phe Arg Ser Asn Gly Leu Thr Ala Asn Glu Ser
145 150 155 160

Gly Arg Leu Ile Asp Phe Leu Lys Asp Val Met Glu Ser Met Asp Lys
165 170 175

```
Glu Glu Ile Glu Ile Thr Thr His Phe Gln Arg Lys Arg Arg Val Arg
            180                 185                 190

Asp Asn Met Thr Lys Lys Met Val Thr Gln Arg Thr Ile Gly Lys Lys
        195                 200                 205

Lys Gln Arg Val Asn Lys Arg Ser Tyr Leu Ile Arg Ala Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Ser Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285

Met Met Thr Asn Ser Gln Asp Thr Glu Leu Ser Phe Thr Ile Thr Gly
    290                 295                 300

Asp Asn Thr Lys Trp Asn Glu Asn Gln Asn Pro Arg Met Phe Leu Ala
305                 310                 315                 320

Met Ile Thr Tyr Ile Thr Lys Asn Gln Pro Glu Trp Phe Arg Asn Ile
                325                 330                 335

Leu Ser Ile Ala Pro Ile Met Phe Ser Asn Lys Met Ala Arg Leu Gly
            340                 345                 350

Lys Gly Tyr Met Phe Glu Ser Lys Arg Met Lys Leu Arg Thr Gln Ile
        355                 360                 365

Pro Ala Glu Met Leu Ala Ser Ile Asp Leu Lys Tyr Phe Asn Glu Ser
    370                 375                 380

Thr Arg Lys Lys Ile Glu Lys Ile Arg Pro Leu Leu Ile Asp Gly Thr
385                 390                 395                 400

Ala Ser Leu Ser Pro Gly Met Met Met Gly Met Phe Asn Met Leu Ser
                405                 410                 415

Thr Val Leu Gly Val Ser Ile Leu Asn Leu Gly Gln Lys Lys Tyr Thr
            420                 425                 430

Lys Thr Thr Tyr Trp Trp Asp Gly Leu Gln Ser Ser Asp Asp Phe Ala
        435                 440                 445

Leu Ile Val Asn Ala Pro Asn His Glu Gly Ile Gln Ala Gly Val Asp
    450                 455                 460

Arg Phe Tyr Arg Thr Cys Lys Leu Val Gly Ile Asn Met Ser Lys Lys
465                 470                 475                 480

Lys Ser Tyr Ile Asn Arg Thr Gly Thr Phe Glu Phe Thr Ser Phe Phe
                485                 490                 495

Tyr Arg Tyr Gly Phe Val Ala Asn Phe Ser Met Glu Leu Pro Ser Phe
            500                 505                 510

Gly Val Ser Gly Ile Asn Glu Ser Ala Asp Met Ser Ile Gly Val Thr
        515                 520                 525

Val Ile Lys Asn Asn Met Ile Asn Asn Asp Leu Gly Pro Ala Thr Ala
    530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Leu
                565                 570                 575

Lys Lys Leu Trp Glu Gln Thr Arg Ser Lys Ala Gly Leu Leu Val Ser
            580                 585                 590
```

Asp Gly Gly Pro Asn Leu Tyr Asn Ile Arg Asn Leu His Ile Pro Glu
        595                 600                 605

Val Cys Leu Lys Trp Glu Leu Met Asp Glu Asp Tyr Gln Gly Arg Leu
    610                 615                 620

Cys Asn Pro Leu Asn Pro Phe Val Ser His Lys Glu Ile Glu Ser Val
625                 630                 635                 640

Asn Asn Ala Val Val Met Pro Ala His Gly Pro Ala Lys Ser Met Glu
                645                 650                 655

Tyr Asp Ala Val Ala Thr Thr His Ser Trp Ile Pro Lys Arg Asn Arg
            660                 665                 670

Ser Ile Leu Asn Thr Ser Gln Arg Gly Ile Leu Glu Asp Glu Gln Met
        675                 680                 685

Tyr Gln Lys Cys Cys Asn Leu Phe Glu Lys Phe Phe Pro Ser Ser Ser
    690                 695                 700

Tyr Arg Arg Pro Val Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                725                 730                 735

Lys Glu Glu Phe Ser Glu Ile Met Lys Ile Cys Ser Thr Ile Glu Glu
            740                 745                 750

Leu Arg Arg Gln Lys Gln
        755

<210> SEQ ID NO 38
<211> LENGTH: 758
<212> TYPE: PRT
<213> ORGANISM: Artificial Sequence
<220> FEATURE:
<223> OTHER INFORMATION: PB1 S678N

<400> SEQUENCE: 38

Met Asp Val Asn Pro Thr Leu Leu Phe Leu Lys Ile Pro Ala Gln Asn
1               5                   10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
        35                  40                  45

Tyr Ser Glu Lys Gly Lys Trp Thr Thr Asn Thr Glu Thr Gly Ala Pro
    50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Gly Ser His Pro Gly Ile Phe Glu Asn Ser Cys Leu Glu Thr Met Glu
            100                 105                 110

Val Val Gln Gln Thr Arg Val Asp Arg Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Gly Leu Thr Ala Asn Glu Ser
145                 150                 155                 160

Gly Arg Leu Ile Asp Phe Leu Lys Asp Val Met Glu Ser Met Asp Lys
                165                 170                 175

Glu Glu Ile Glu Ile Thr Thr His Phe Gln Arg Lys Arg Arg Val Arg
            180                 185                 190

-continued

```
Asp Asn Met Thr Lys Lys Met Val Thr Gln Arg Thr Ile Gly Lys Lys
        195                 200                 205

Lys Gln Arg Val Asn Lys Arg Ser Tyr Leu Ile Arg Ala Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Ser Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285

Met Met Thr Asn Ser Gln Asp Thr Glu Leu Ser Phe Thr Ile Thr Gly
    290                 295                 300

Asp Asn Thr Lys Trp Asn Glu Asn Gln Asn Pro Arg Met Phe Leu Ala
305                 310                 315                 320

Met Ile Thr Tyr Ile Thr Lys Asn Gln Pro Glu Trp Phe Arg Asn Ile
                325                 330                 335

Leu Ser Ile Ala Pro Ile Met Phe Ser Asn Lys Met Ala Arg Leu Gly
            340                 345                 350

Lys Gly Tyr Met Phe Glu Ser Lys Arg Met Lys Leu Arg Thr Gln Ile
        355                 360                 365

Pro Ala Glu Met Leu Ala Ser Ile Asp Leu Lys Tyr Phe Asn Glu Ser
    370                 375                 380

Thr Arg Lys Lys Ile Glu Lys Ile Arg Pro Leu Leu Ile Asp Gly Thr
385                 390                 395                 400

Ala Ser Leu Ser Pro Gly Met Met Met Gly Met Phe Asn Met Leu Ser
                405                 410                 415

Thr Val Leu Gly Val Ser Ile Leu Asn Leu Gly Gln Lys Lys Tyr Thr
            420                 425                 430

Lys Thr Thr Tyr Trp Trp Asp Gly Leu Gln Ser Ser Asp Asp Phe Ala
        435                 440                 445

Leu Ile Val Asn Ala Pro Asn His Glu Gly Ile Gln Ala Gly Val Asp
    450                 455                 460

Arg Phe Tyr Arg Thr Cys Lys Leu Val Gly Ile Asn Met Ser Lys Lys
465                 470                 475                 480

Lys Ser Tyr Ile Asn Arg Thr Gly Thr Phe Glu Phe Thr Ser Phe Phe
                485                 490                 495

Tyr Arg Tyr Gly Phe Val Ala Asn Phe Ser Met Glu Leu Pro Ser Phe
            500                 505                 510

Gly Val Ser Gly Ile Asn Glu Ser Ala Asp Met Ser Ile Gly Val Thr
        515                 520                 525

Val Ile Lys Asn Asn Met Ile Asn Asn Asp Leu Gly Pro Ala Thr Ala
    530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Leu
                565                 570                 575

Lys Lys Leu Trp Glu Gln Thr Arg Ser Lys Ala Gly Leu Leu Val Ser
            580                 585                 590

Asp Gly Gly Pro Asn Leu Tyr Asn Ile Arg Asn Leu His Ile Pro Glu
        595                 600                 605

Val Cys Leu Lys Trp Glu Leu Met Asp Glu Asp Tyr Gln Gly Arg Leu
```

-continued

```
    610                 615                 620

Cys Asn Pro Leu Asn Pro Phe Val Ser His Lys Glu Ile Glu Ser Val
625                 630                 635                 640

Asn Asn Ala Val Val Met Pro Ala His Gly Pro Ala Lys Ser Met Glu
                645                 650                 655

Tyr Asp Ala Val Ala Thr Thr His Ser Trp Ile Pro Lys Arg Asn Arg
            660                 665                 670

Ser Ile Leu Asn Thr Asn Gln Arg Gly Ile Leu Glu Asp Glu Gln Met
        675                 680                 685

Tyr Gln Lys Cys Cys Asn Leu Phe Glu Lys Phe Phe Pro Ser Ser Ser
    690                 695                 700

Tyr Arg Arg Pro Val Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                725                 730                 735

Lys Glu Glu Phe Ser Glu Ile Met Lys Ile Cys Ser Thr Ile Glu Glu
            740                 745                 750

Leu Arg Arg Gln Lys Gln
        755
```

RECOMBINANT HIGH GROWTH RATE INFLUENZA VIRUS COMPRISING MUTATIONS IN M1, NS2, AND PB2

CROSS-REFERENCE TO RELATED APPLICATIONS

This application is the U.S. national stage of International Patent Application No. PCT/EP2020/051728, filed on Jan. 24, 2020 and entitled HIGH GROWTH INFLUENZA VIRUS, which claims the benefit of priority under 35 U.S.C. § 119(e) from U.S. Patent Application No. 62/796,544, filed Jan. 24, 2019, and under 35 U.S.C. § 119(a) from European Patent Application No. 19160992.4, filed Mar. 6, 2019. The disclosures of the foregoing applications are incorporated herein by reference in their entirety.

SEQUENCE LISTING

The entire content of a Sequence Listing titled "Sequence-_Listing.txt," created on Jul. 5, 2021 and having a size of 112 kilobytes, which has been submitted in electronic form in connection with the present application, is hereby incorporated by reference herein in its entirety.

FIELD OF THE INVENTION

The present invention provides recombinant influenza virus and influenza virus vectors comprising amino acid modifications in the PB2, PB1, M and/or NS2 proteins which exhibit highly increased growth rates compared to unmodified influenza virus.

Further provided are pharmaceutical compositions comprising reassortant virus and viral vectors comprising said modifications and their use for vaccination purposes.

BACKGROUND OF THE INVENTION

Epidemics and pandemics caused by viral diseases are still claiming human lives and are impacting global economy. Influenza is responsible for millions of lost work days and visits to the doctor, hundreds of thousands of hospitalizations worldwide (Couch 1993, Ann. NY. Acad. Sci 685;803), tens of thousands of excess deaths (Collins & Lehmann 1953 Public Health Monographs 213:1; Glezen 1982 Am. J. Public Health 77:712) and billions of Euros in terms of health-care costs (Williams et al. 1988, Ann. Intern. Med. 108:616). When healthy adults get immunized, currently available vaccines prevent clinical disease in 70-90% of cases. This level is reduced to 30-70% in those over the age of 65 and drops still further in those over 65 living in nursing homes (Strategic Perspective 2001: The Antiviral Market. Datamonitor. p. 59). The virus's frequent antigenic changes further contribute to a large death toll because not even annual vaccination can guarantee protection. Hence, the U.S. death toll rose from 16,363 people in 1976/77 to four times as many deaths in 1998/99. In the 2017-2018 season, flu-related deaths reached about 80.000.

Human influenza virus reference strains have to be prepared when an antigenically new strain is recommended by the World Health Organisation (WHO) for being included in the current vaccine formulation. The segmented nature of the influenza virus genome allows for reassortment of segments during virus replication in cells infected with two or more influenza viruses. The reassortment of segments, combined with genetic mutation and drift, can give rise to a myriad of divergent strains of influenza virus over time. The new strains exhibit antigenic variation in their hemagglutinin (HA) and/or neuraminidase (NA) proteins, and in particular the gene coding for the HA protein has a high rate of variability.

Currently, influenza strains for vaccination can be prepared by classic reassortment of the recommended strain and a laboratory strain or by reverse genetics technology wherein the gene segments coding for the surface proteins are derived from the recommended strain and other gene segments are derived from high growth virus strains.

The predominant current practice for the prevention of influenza is vaccination. As the influenza HA protein is the major target antigen for the protective immune responses of a host to the virus and is highly variable, the isolation of influenza virus and the identification and characterization of the HA antigen in viruses associated with recent outbreaks is important for vaccine production. Based on prevalence and prediction, a vaccine is designed to stimulate a protective immune response against the predominant and expected influenza virus strains.

There are three general types of influenza viruses, Type A, Type B and Type C, which are defined by the absence of serological cross-reactivity between their internal proteins. Influenza Type A viruses are further classified into subtypes based on antigenic and genetic differences of their glycoproteins, the HA and NA proteins. Most of all the known HA and NA subtypes (H1 to H17 and N1 to N10) have been isolated from birds, which are thought to act as a natural reservoir for influenza.

The influenza virions consist of an internal ribonucleoprotein core (a helical nucleocapsid) containing the single-stranded RNA genome, and an outer lipoprotein envelope lined inside by a matrix protein (M1). The segmented genome of influenza A virus consists of eight molecules of linear, negative polarity, single-stranded RNAs which encodes eleven (some influenza A strains ten) polypeptides, including: the RNA-dependent RNA polymerase proteins (PB2, PB1 and PA) and nucleoprotein (NP) which form the nucleocapsid; the matrix membrane proteins (M1, M2); two surface glycoproteins which project from the lipid containing envelope: hemagglutinin (HA) and neuraminidase (NA); the nonstructural protein (NS1) and nuclear export protein (NEP). Most influenza A strains also encode an eleventh protein (PB1-F2) believed to have proapoptotic properties.

Transcription and replication of the genome takes place in the nucleus and assembly occurs via budding on the plasma membrane. The viruses can reassort genes during mixed infections. Influenza virus adsorbs via HA to sialyloligosaccharides in cell membrane glycoproteins and glycolipids. Following endocytosis of the virion, a conformational change in the HA molecule occurs within the cellular endosome which facilitates membrane fusion, thus triggering uncoating. The nucleocapsid migrates to the nucleus where viral mRNA is transcribed by a unique mechanism in which viral endonuclease cleaves the capped 5'-terminus from cellular heterologous mRNAs which then serve as primers for transcription of viral RNA templates by the viral transcriptase. Transcripts terminate at sites 15 to 22 bases from the ends of their templates, where oligo (U) sequences act as signals for the addition of poly(A) tracts. Of the eight viral RNA molecules so produced, six are monocistronic messages that are translated directly into the proteins representing HA, NA, NP and the viral polymerase proteins, PB2, PB1 and PA. The other two transcripts undergo splicing, each yielding two mRNAs which are translated in different reading frames to produce M1, M2, NS1 and NEP.

In other words, the eight viral RNA segments code for eleven proteins: nine structural and 2 non-structural (NS1 and PB1-F2) proteins.

Growth of viruses, especially of influenza virus in embryonated chicken eggs have been shown to result in effective production of influenza virus particles which can be either used for production of inactivated or live attenuated influenza virus vaccine strains. Nevertheless, during the last years intensive efforts have been made in establishing production systems of virus using cell culture because egg-based method requires a steady supply of specific pathogen-free eggs which could be problematic in case of pandemic. The cell-based technology is an alternative production process that is independent of eggs suppliers and can be started as soon as the seed virus is available. Besides this, inactivated influenza vaccine prepared from the virus grown in mammalian cells was shown to induce more cross-reactive serum antibodies and reveals better protection than egg-grown vaccine (Alymova et al., 1998, J Virol 72, 4472-7).

WO2009/080806A2 and WO2017/143236A1 describe influenza virus comprising M gene modifications.

Ping J. et al. report influenza virus mutants having various modifications within the PA, PB1, PB2, NP, NS and M viral segments (Proc. Natl. Acad. Sci., 113, 51, 2016, pp. E8296-E8305).

Generally, in view of the tight timelines from getting access to the influenza strains as recommended by WHO for production of interpandemic or pandemic vaccine compositions and producing said viruses, it is of utmost importance to have virus strains providing the viral backbone for developing vaccine virus particles which are of high yield for vaccine production and which can be produced in cell culture.

SUMMARY OF THE INVENTION

Modifications such as mutations that increase the replicative ability of influenza viruses in cell culture are useful to amplify these viruses and to establish robust influenza vaccine platforms. The herein identified amino acid substitutions result in higher virus titers in cell culture, especially in Vero cells but may also increase virus titers in MDCK cells, embryonated chicken eggs and any other cells useful for virus propagation, thereby allowing more efficient influenza virus growth and more cost-effective vaccine production. The mutations can be used in any combinations, depending on the selected virus backbone, on the respective cell line (or egg) in use and the desired level of increase in the replication of the virus.

The virus of the invention can thus be used as high yield influenza virus master strain or, as an alternative, as influenza virus vector further expressing heterologous genes of interest.

The invention provides isolated recombinant, e.g., reassortant, influenza viruses with increased yield lacking the functional NS1 protein and having selected amino acid residues at one or more selected positions in one, two or more gene segments coding for PB1, PB2, M (encoding M1 and M2), and/or NS proteins (encoding NS2 protein), e.g., in selected amino acid residues at positions specifically disclosed herein of M1 and NS2, M1, PB2 and NS2, PB1, M1 and/or NS2, PB1 and/or PB2; and comprising HA and NA sequences of interest, e.g. from annual and pandemic strains, which are produced more efficiently and cost-effectively via cell culture, such as in Vero, MDCK or PerC6 cells or in embryonated chicken eggs.

Specifically, the host cells for cell culture propagation of the inventive delNS1 virus are interferon deficient, such as Vero cells.

According to an embodiment of the invention, herein provided is a recombinant influenza B virus with increased growth rate lacking the functional NS1 protein (delNS1 influenza) comprising

- an M1 protein having an amino acid substitution at position 89 according to the numbering of SEQ ID No. 6, specifically having serine at amino acid position 89, and
- NS and PB gene segments comprising one or more nucleotide modifications resulting in
  - an NS2 protein having an amino acid substitution at positions 75 and/or 76 according to the numbering of SEQ ID No. 10, specifically having glycine at position 75 and/or arginine at position 76, and/or
  - a PB2 protein having an amino acid substitution at position 427 according to the numbering of SEQ ID No. 2, specifically having serine at position 427.

SEQ ID No.6 represents a wild type M protein sequence.

SEQ ID No.10 represents a wild type NS2 protein sequence.

According to an embodiment of the invention, herein provided is a recombinant influenza B virus with increased growth rate lacking the functional NS1 protein (delNS1 influenza) comprising

- an M1 protein comprising the amino acid sequence SEQ ID No. 6 with an amino acid substitution at position 89, specifically having serine at amino acid position 89, and
- NS2 and PB2 proteins comprising amino acid sequences SEQ ID No. 10 and SEQ ID No. 2, wherein
  - the NS2 protein contains an amino acid substitution at positions 75 and/or 76, specifically glycine at position 75 and/or arginine at position 76, and/or
  - the PB2 protein contains an amino acid substitution at position 427, specifically serine at position 427.

SEQ ID No.2 represents a wild type PB2 protein sequence.

According to a further embodiment, the recombinant influenza B virus comprises the amino acid sequences SEQ ID No. 4, SEQ ID No. 8 and SEQ ID No. 12 and/or comprises the nucleotide sequences SEQ ID No. 3, SEQ ID No. 7, and SEQ ID No. 11.

Specifically, the recombinant influenza B virus as described herein comprises the amino acid sequences SEQ ID No. 4, SEQ ID No. 8 and SEQ ID No. 12 or any amino acid sequence which is at least 95%, specifically 96%, 97%, 98% or 99% identical with any one of SEQ ID No. 4, SEQ ID No. 8 and SEQ ID No. 12 with the proviso that position 427 of SEQ ID No. 4, positions 75 and 76 of SEQ ID NO. 10 and/or position 89 of SEQ ID No. 8 are conserved.

According to a further embodiment the recombinant influenza B virus comprises the amino acid sequences SEQ ID No. 4, SEQ ID No. 8 and SEQ ID No. 34 and/or the nucleotide sequences SEQ ID No. 3, SEQ ID No. 7, and SEQ ID No. 33.

Specifically, the recombinant influenza B virus as described herein comprises the amino acid sequences SEQ ID No. 4, SEQ ID No. 8 and SEQ ID No. 34 or any amino acid sequence which is at least 95%, specifically 96%, 97%, 98% or 99% identical with any one of SEQ ID No. 4, SEQ ID No. 8 and SEQ ID No. 34 with the proviso that position 427 of SEQ ID No. 4, position 76 of SEQ ID NO. 34 and/or position 89 of SEQ ID No. 8 are conserved.

According to a further embodiment, the recombinant influenza B virus comprises the amino acid sequences SEQ ID No. 8 and SEQ ID No. 12 and/or the nucleotide sequences SEQ ID No. 7, and SEQ ID No. 11.

Specifically, the recombinant influenza B virus as described herein comprises the amino acid sequences SEQ ID No. 8 and SEQ ID No. 12 or any amino acid sequence which is at least 95%, specifically 96%, 97%, 98% or 99% identical with any one of SEQ ID No. 8 and SEQ ID No. 12 with the proviso that positions 76 and 75 of SEQ ID NO. 12 and position 89 of SEQ ID No. 8 are conserved.

According to a further embodiment, the recombinant influenza B virus comprises the amino acid sequences SEQ ID No. 8 and SEQ ID No. 34 and/or the nucleotide sequences SEQ ID No. 7, and SEQ ID No. 33.

Specifically, the recombinant influenza B virus as described herein comprises the amino acid sequences SEQ ID No. 8 and SEQ ID No. 34 or any amino acid sequence which is at least 95%, specifically 96%, 97%, 98% or 99% identical with any one of SEQ ID No. 8 and SEQ ID No. 34 with the proviso that positions 76 of SEQ ID NO. 34 and position 89 of SEQ ID No. 8 are conserved. According to an alternative embodiment, herein provided is a recombinant delNS1 influenza B virus comprising M, PB and NS gene segments comprising one or more nucleotide modifications resulting in

- an M1 protein having an amino acid substitution at position 89 and/or 93, according to the numbering of SEQ ID No. 6, and/or
- an NS2 protein having an amino acid substitution at positions 75, 76 and/or 117, according to the numbering of SEQ ID No. 10, and/or
- a PB2 protein having an amino acid substitution at position 427 according to the numbering of SEQ ID No. 2 and/or
- a PB1 protein having an amino acid substitution at position 67 according to the numbering of SEQ ID No. 14, or any combinations thereof.

One specific embodiment provided herein is a recombinant influenza B virus comprising M and NS gene segments which contain nucleotide modifications encoding

- an M1 protein having an amino acid substitution at position 89, according to the numbering of SEQ ID No. 6, and
- an NS2 protein having an amino acid substitution at position 76, according to the numbering of SEQ ID No. 10.

According to an embodiment as described herein, the recombinant influenza B virus further comprises a PB2 gene encoding a PB2 protein having an amino acid substitution at position 427 according to the numbering of SEQ ID No. 2.

According to a further embodiment, the recombinant influenza B virus further comprises an NS gene encoding an NS2 protein having an amino acid substitution at position 75 according to the numbering of SEQ ID No. 10.

According to a further embodiment, the recombinant influenza B virus comprises

- an M1 protein having an amino acid substitution at position 89, according to the numbering of SEQ ID No. 6, specifically having serine at amino acid position 89;
- a PB2 protein having an amino acid substitution at position 427 according to the numbering of SEQ ID No. 2, specifically having serine at amino acid position 427; and
- an NS2 protein having amino acid substitutions at positions 75 and/or 76, according to the numbering of SEQ ID No. 10, specifically having glycine at amino acid position 76 and/or arginine at amino acid position 75.

In an embodiment, B/Thüringen/02/06, a B/Jinagsu/10/03-like virus from the B Yamagata lineage, may serve as genetic backbone for generating influenza virus vaccine, specifically B/Thüringen/02/06 comprising gene segments encoding amino acid substitutions at positions specified herein and HA and NA proteins may be derived from any strain such as but not limited to B/Murmansk/3/2010. According to a specific embodiment, herein provided is a recombinant influenza B virus with increased growth rate lacking the functional NS1 protein (delNS1 influenza) comprising at least two gene segments comprising one or more nucleotide modifications resulting in

- an M1 protein having an amino acid substitution at position 93 according to the numbering of SEQ ID No. 6, specifically having arginine at amino acid position 93, and/or
- a PB1 protein having an amino acid substitution at position 67 according to the numbering of SEQ ID No. 14, specifically having asparagine at amino acid position 67, and/or
- an NS2 protein having an amino acid substitution at position 117 according to the numbering of SEQ ID No. 10, specifically having histidine at amino acid position 117.

SEQ ID No.14 represents a wild type PB1 protein sequence.

According to a specific embodiment, herein provided is a recombinant influenza B virus with increased growth rate lacking the functional NS1 protein (delNS1 influenza) comprising

- an M1 protein comprising the amino acid sequence SEQ ID No. 6 having an amino acid substitution at position 93, specifically having arginine at amino acid position 93, and/or
- a PB1 protein comprising the amino acid sequence SEQ ID No. 14 having an amino acid substitution at position 67, specifically having asparagine at amino acid position 67, and/or
- an NS2 protein comprising the amino acid sequence SEQ ID No. 10 having an amino acid substitution at position 117, specifically having histidine at amino acid position 17.

Specifically, the recombinant influenza B virus described herein comprises at least two of the amino acid sequences SEQ ID No. 16, SEQ ID No. 20 and SEQ ID No. 24 and/or comprising at least two nucleotide sequences of SEQ ID No. 15, SEQ ID No. 19 and SEQ ID No. 23.

Specifically, the recombinant influenza B virus as described herein comprises at least two of the amino acid sequences SEQ ID No. 16, SEQ ID No. 20 and SEQ ID No. 24 or any amino acid sequence which is at least 95%, specifically 96%, 97%, 98% or 99% identical with any one of SEQ ID No. 16, SEQ ID No. 20 and SEQ ID No. 24 with the proviso that position 67 of SEQ ID No. 16, position 93 of SEQ ID NO. 20 and/or position 117 of SEQ ID No. 24 are conserved.

According to a further embodiment, herein provided is a recombinant delNS1 influenza B with increased yield virus comprising PB1, M and NS genes which contain at least two nucleotide modifications encoding

- a PB1 protein having an amino acid substitution at position 67 according to the numbering of SEQ ID No. 14, an M1 protein having an amino acid substitution at position 93 according to the numbering of SEQ ID No. 6, and/or an NS2 protein having an amino acid substitution at position 117 according to the numbering of SEQ ID No. 10.

In a further embodiment, the recombinant influenza B virus as described herein comprises modified proteins selected from the group consisting of a PB1 protein having asparagine at amino acid position 67 with reference to the numbering of SEQ ID No. 14, an M1 protein having arginine at amino acid position 93 with reference to the numbering of SEQ ID No. 6, and/or an NS2 protein having histidine at amino acid position 117 with reference to the numbering of SEQ ID No. 10, Further provided is the recombinant influenza B virus as described herein comprising a PB1 protein having an amino acid substitution at position 67 according to the numbering of SEQ ID No. 14, an M1 protein having an amino acid substitution at position 93 according to the numbering of SEQ ID No. 6, and an NS2 protein having an amino acid substitution at position 117 according to the numbering of SEQ ID No. 10.

In an embodiment, influenza virus B/Thüringen/02/06 may serve as genetic backbone, with HA and/or NA proteins may be derived from any strain such as but not limited to B/Phuket/3073/2013. for generating influenza virus vaccine, specifically B/Thüringen/02/06 comprising gene segments encoding amino acid substitutions at positions specified herein. According to a further embodiment, herein provided is a recombinant influenza A virus with increased growth rate lacking the functional NS1 protein (delNS1 influenza) comprising a PB2 protein having an amino acid substitution at position 80 according to the numbering of SEQ ID No. 26, specifically having arginine at amino acid position 80 and a PB1 gene which contains at least one nucleotide modifications encoding a PB1 protein having an amino acid substitution at position 97 and 678 according to the numbering of SEQ ID No. 30, specifically having glycine at amino acid position 97 and asparagine at amino acid position 678.

According to a further embodiment, herein provided is a recombinant influenza A virus with increased growth rate lacking the functional NS1 protein (delNS1 influenza) comprising a PB2 protein containing amino acid sequence SEQ ID No. 26 having an amino acid substitution at position 80, specifically having arginine at amino acid position 80 and a PB1 protein containing the amino acid sequence SEQ ID No. 30 having an amino acid substitution at position 97 and 678, specifically having glycine at amino acid position 97 and asparagine at amino acid position 678.

Specifically, the recombinant influenza A virus comprises the nucleotide sequence of SEQ ID No. 27 in combination with any one of SEQ ID Nos. 31, 35 and 36.

Specifically, the recombinant influenza A virus comprises the amino acid sequence of SEQ ID No. 28 in combination with any one of SEQ ID Nos. 32, 37 and 38.

Specifically, the recombinant influenza A virus as described herein comprises the amino acid sequences SEQ ID No. 28, in combination with any one of SEQ ID No. 32, 37 and 38 or any amino acid sequence which is at least 95%, specifically 96%, 97%, 98% or 99% identical with any one of SEQ ID No. 28, SEQ ID No. 32, 37 and 38, with the proviso that position 80 of SEQ ID No. 28 and any one of position 97 and 678 of SEQ ID NO. 32, position 97 or SEQ ID NO. 37 and/or position 678 of SEQ ID No. 24 are conserved.

According to a further embodiment, herein provided is a recombinant influenza A virus comprising PB1 and PB2 genes which contain at least two nucleotide modifications encoding a PB1 protein having an amino acid substitution at position 97 and 678 according to the numbering of SEQ ID No. 30, and/or a PB2 protein having an amino acid substitution at position 80 according to the numbering of SEQ ID No. 26.

According to a further embodiment, the recombinant influenza A virus described herein comprises a PB1 protein having glycine at amino acid position 97 and asparagine at amino acid position 678 with reference to the numbering of SEQ ID No. 30, and/or a PB2 protein having arginine at amino acid position 80 with reference to the numbering of SEQ ID No. 26.

According to the embodiment of the present invention, the recombinant influenza virus disclosed herein is a reassortant virus, specifically wherein said virus comprises at least two gene segments of a seasonal or pandemic strain origin, specifically the virus is attenuated or replication deficient, preferably it is completely replication deficient.

The recombinant influenza virus as described herein can comprise one or more modifications within the HA and/or NA genes.

According to a specific embodiment, the recombinant delNS1 influenza encompassed herein contains a modified NS1 encoding gene segment which codes for an NS1 protein lacking a functional RNA binding domain, a functional carboxy terminal domain or lacking both functional RNA binding domain and/or functional carboxy terminal domain or a combination thereof.

In a further embodiment herein provided is a vaccine composition comprising an immunogenicity inducing effective amount of influenza virus in a mixture with a pharmaceutically acceptable carrier.

According to a further embodiment, herein provided is an isolated nucleic acid encoding the recombinant influenza virus described herein.

In a further embodiment, the influenza virus as described herein is for use in the manufacture of a medicament.

In a further embodiment, the influenza virus described herein is used in therapeutic or prophylactic treatment of an influenza virus infection.

In some embodiments, a plurality of vectors incorporating at least the 6 internal genome segments of a one influenza A or B strain along with one or more genome segments encoding immunogenic influenza surface antigens of a different influenza strain are introduced into a population of host cells. For example, at least the 6 internal genome segments ("the backbone") of a selected influenza A or B strain, e.g., an artificially engineered influenza A or B strain including an amino acid substitution at one or more of the positions specified above, e.g. but not limited to B/Thüringen/02/06 or A/IVR-116 are introduced into a population of host cells along with one or more segments encoding immunogenic antigens derived from another virus strain. Typically, the immunogenic surface antigens include either or both of the hemagglutinin (HA) and/or neuraminidase (NA) antigens. In embodiments where a single segment encoding an immunogenic surface antigen is introduced, the 7 complementary segments of the selected virus are also introduced into the host cells.

In a further embodiment, herein provided is a plurality of influenza virus vectors for preparing a reassortant deINS1 influenza B virus described herein, comprising a) a vector for vRNA production comprising a promoter operably linked to an influenza virus PA DNA linked to a transcription termination sequence, a vector for vRNA production comprising a promoter operably linked to an influenza virus PB1 DNA linked to a transcription termination sequence, a vector for vRNA production comprising a promoter operably linked to an influenza virus PB2 DNA linked to a transcription termination sequence, a vector for vRNA production comprising a promoter operably linked to an influenza virus HA DNA linked to a transcription termination sequence, a vector for vRNA production comprising a promoter operably linked to an influenza virus NP DNA linked to a transcription termination sequence, a vector for vRNA production comprising a promoter operably linked to an influenza virus NA DNA linked to a transcription termination sequence, a vector for vRNA production comprising a promoter operably linked to an influenza virus M DNA linked to a transcription termination sequence, and a vector for vRNA production comprising a promoter operably linked to an influenza virus NS cDNA or part thereof linked to a transcription termination sequence, wherein the PB1, PB2, PA, NP, NS, and M DNAs in the vectors for vRNA production encode M1 with a serine at position 89, and at least one of NS2 with glycine at position 76, NS2 with an arginine at position 75, PB2 serine at position 427, and optionally b) a vector for mRNA production comprising a promoter operably linked to a DNA segment encoding influenza virus PA, a vector for mRNA production comprising a promoter operably linked to a DNA segment encoding influenza virus PB1, a vector for mRNA production comprising a promoter operably linked to a DNA segment encoding influenza virus PB2, and a vector for mRNA production comprising a promoter operably linked to a DNA segment encoding influenza virus NP, and optionally a vector for mRNA production comprising a promoter operably linked to a DNA segment encoding influenza virus HA, a vector for mRNA production comprising a promoter operably linked to a DNA segment encoding influenza virus NA, a vector for mRNA production comprising a promoter operably linked to a DNA segment encoding influenza virus M1, a vector for mRNA production comprising a promoter operably linked to a DNA segment encoding influenza virus M2, or a vector for mRNA production comprising a promoter operably linked to a DNA segment encoding influenza virus NS2.

In a further embodiment, herein provided is a plurality of influenza virus vectors, comprising a) a vector for vRNA production comprising a promoter operably linked to an influenza virus PA DNA linked to a transcription termination sequence, a vector for vRNA production comprising a promoter operably linked to an influenza virus PB1 DNA linked to a transcription termination sequence, a vector for vRNA production comprising a promoter operably linked to an influenza virus PB2 DNA linked to a transcription termination sequence, a vector for vRNA production comprising a promoter operably linked to an influenza virus HA DNA linked to a transcription termination sequence, a vector for vRNA production comprising a promoter operably linked to an influenza virus NP DNA linked to a transcription termination sequence, a vector for vRNA production comprising a promoter operably linked to an influenza virus NA DNA linked to a transcription termination sequence, a vector for vRNA production comprising a promoter operably linked to an influenza virus M DNA linked to a transcription termination sequence, and a vector for vRNA production comprising a promoter operably linked to an influenza virus NS cDNA or part thereof linked to a transcription termination sequence, wherein the PB1, PB2, PA, NP, NS, and M DNAs in the vectors for vRNA production encode M1 with an arginine at position 93 and at least one of: NS2 with histidine at position 117, PB1 with an asparagine at position 67, b) a vector for mRNA production comprising a promoter operably linked to a DNA segment encoding influenza virus PA, a vector for mRNA production comprising a promoter operably linked to a DNA segment encoding influenza virus PB1, a vector for mRNA production comprising a promoter operably linked to a DNA segment encoding influenza virus PB2, and a vector for mRNA production comprising a promoter operably linked to a DNA segment encoding influenza virus NP, and optionally a vector for mRNA production comprising a promoter operably linked to a DNA segment encoding influenza virus HA, a vector for mRNA production comprising a promoter operably linked to a DNA segment encoding influenza virus NA, a vector for mRNA production comprising a promoter operably linked to a DNA segment encoding influenza virus M1, a vector for mRNA production comprising a promoter operably linked to a DNA segment encoding influenza virus M2, or a vector for mRNA production comprising a promoter operably linked to a DNA segment encoding influenza virus NS2.

In a further embodiment, herein provided is a plurality of influenza virus vectors, comprising a) a vector for vRNA production comprising a promoter operably linked to an influenza virus PA DNA linked to a transcription termination sequence, a vector for vRNA production comprising a promoter operably linked to an influenza virus PB1 DNA linked to a transcription termination sequence, a vector for vRNA production comprising a promoter operably linked to an influenza virus PB2 DNA linked to a transcription termination sequence, a vector for vRNA production comprising a promoter operably linked to an influenza virus HA DNA linked to a transcription termination sequence, a vector for vRNA production comprising a promoter operably linked to an influenza virus NP DNA linked to a transcription termination sequence, a vector for vRNA production comprising a promoter operably linked to an influenza virus NA DNA linked to a transcription termination sequence, a vector for vRNA production comprising a promoter operably linked to an influenza virus M DNA linked to a transcription termination sequence, and a vector for vRNA production comprising a promoter operably linked to an influenza virus NS cDNA or part thereof linked to a transcription termination sequence, wherein the PB1, PB2, PA, NP, NS, and M DNAs in the vectors for vRNA production encode at least two of: PB1 with a glycine at position 97, PB1 with an asparagine at position 678, PB2 with arginine at position 80, b) a vector for mRNA production comprising a promoter operably linked to a DNA segment encoding influenza virus PA, a vector for mRNA production comprising a promoter operably linked to a DNA segment encoding influenza virus PB1, a vector for mRNA production comprising a promoter operably linked to a DNA segment encoding influenza virus PB2, and a vector for mRNA production comprising a promoter operably linked to a DNA segment encoding influenza virus NP, and optionally a vector for mRNA production comprising a promoter operably linked to a DNA segment encoding influenza virus HA, a vector for mRNA production comprising a promoter operably linked to a DNA segment encoding influenza virus NA, a vector for mRNA production comprising a promoter operably linked to a DNA segment encoding influenza virus M1, a vector for mRNA production comprising a promoter operably linked to a DNA segment encoding influenza virus M2, or a vector for mRNA production comprising a promoter operably linked to a DNA segment encoding influenza virus NS2.

According to yet a further embodiment of the invention, herein provided is a method for preparing an influenza virus B described herein, by contacting a cell with a) a vector for vRNA production comprising a promoter operably linked to an influenza virus PA DNA linked to a transcription termination sequence, a vector for vRNA production comprising a promoter operably linked to an influenza virus PB1 DNA linked to a transcription termination sequence, a vector for vRNA production comprising a promoter operably linked to an influenza virus PB2 DNA linked to a transcription termination sequence, a vector for vRNA production comprising a promoter operably linked to an influenza virus HA DNA linked to a transcription termination sequence, a vector for vRNA production comprising a promoter operably linked to an influenza virus NP DNA linked to a transcription termination sequence, a vector for vRNA production comprising a promoter operably linked to an influenza virus NA DNA linked to a transcription termination sequence, a vector for vRNA production comprising a promoter operably linked to an influenza virus M DNA linked to a transcription termination sequence, and a vector for vRNA production comprising a promoter operably linked to an influenza virus NS cDNA or part thereof linked to a transcription termination sequence, wherein the PB1, PB2, PA, NP, NS, and M DNAs in the vectors for vRNA production encode M1 with a serine at position 89 and at least one of: NS2 with glycine at position 76, NS2 with an arginine at position 75, PB2 serine at position 427, and optionally b) a vector for mRNA production comprising a promoter operably linked to a DNA segment encoding influenza virus PA, a vector for mRNA production comprising a promoter operably linked to a DNA segment encoding influenza virus PB1, a vector for mRNA production comprising a promoter operably linked to a DNA segment encoding influenza virus PB2, and a vector for mRNA production comprising a promoter operably linked to a DNA segment encoding influenza virus NP, and optionally a vector for mRNA production comprising a promoter operably linked to a DNA segment encoding influenza virus HA, a vector for mRNA production comprising a promoter operably linked to a DNA segment encoding influenza virus NA, a vector for mRNA production comprising a promoter operably linked to a DNA segment encoding influenza virus M1, a vector for mRNA production comprising a promoter operably linked to a DNA segment encoding influenza virus M2, or a vector for mRNA production comprising a promoter operably linked to a DNA segment encoding influenza virus NS2.

Further provided in an embodiment is a method for preparing an influenza virus B of the present invention, by contacting a cell with a) a vector for vRNA production comprising a promoter operably linked to an influenza virus PA DNA linked to a transcription termination sequence, a vector for vRNA production comprising a promoter operably linked to an influenza virus PB1 DNA linked to a transcription termination sequence, a vector for vRNA production comprising a promoter operably linked to an influenza virus PB2 DNA linked to a transcription termination sequence, a vector for vRNA production comprising a promoter operably linked to an influenza virus HA DNA linked to a transcription termination sequence, a vector for vRNA production comprising a promoter operably linked to an influenza virus NP DNA linked to a transcription termination sequence, a vector for vRNA production comprising a promoter operably linked to an influenza virus NA DNA linked to a transcription termination sequence, a vector for vRNA production comprising a promoter operably linked to an influenza virus M DNA linked to a transcription termination sequence, and a vector for vRNA production comprising a promoter operably linked to an influenza virus NS cDNA or part thereof linked to a transcription termination sequence, wherein the PB1, PB2, PA, NP, NS, and M DNAs in the vectors for vRNA production encode M1 with an arginine at position 93 and at least one of: NS2 with histidine at position 117, and/or PB1 with an asparagine at position 67, b) a vector for mRNA production comprising a promoter operably linked to a DNA segment encoding influenza virus PA, a vector for mRNA production comprising a promoter operably linked to a DNA segment encoding influenza virus PB1, a vector for mRNA production comprising a promoter operably linked to a DNA segment encoding influenza virus PB2, and a vector for mRNA production comprising a promoter operably linked to a DNA segment encoding influenza virus NP, and optionally a vector for mRNA production comprising a promoter operably linked to a DNA segment encoding influenza virus HA, a vector for mRNA production comprising a promoter operably linked to a DNA segment encoding influenza virus NA, a vector for mRNA production comprising a promoter operably linked to a DNA segment encoding influenza virus M1, a vector for mRNA production comprising a promoter operably linked to a DNA segment encoding influenza virus M2, or a vector for mRNA production comprising a promoter operably linked to a DNA segment encoding influenza virus NS2.

In a further aspect, provided herein is a method for preparing an influenza virus A described herein, by contacting a cell with a) a vector for vRNA production comprising a promoter operably linked to an influenza virus PA DNA linked to a transcription termination sequence, a vector for vRNA production comprising a promoter operably linked to an influenza virus PB1 DNA linked to a transcription termination sequence, a vector for vRNA production comprising a promoter operably linked to an influenza virus PB2 DNA linked to a transcription termination sequence, a vector for vRNA production comprising a promoter operably linked to an influenza virus HA DNA linked to a transcription termination sequence, a vector for vRNA production comprising a promoter operably linked to an influenza virus NP DNA linked to a transcription termination sequence, a vector for vRNA production comprising a promoter operably linked to an influenza virus NA DNA linked to a transcription termination sequence, a vector for vRNA production comprising a promoter operably linked to an influenza virus M DNA linked to a transcription termination sequence, and a vector for vRNA production comprising a promoter operably linked to an influenza virus NS cDNA linked to a transcription termination sequence, wherein the PB1, PB2, PA, NP, NS, and M DNAs in the vectors for vRNA production encode at least two of: PB1 with a glycine at position 97, PB1 with an asparagine at position 678, and PB2 with arginine at position 80, b) a vector for mRNA production comprising a promoter operably linked to a DNA segment encoding influenza virus PA, a vector for mRNA production comprising a promoter operably linked to a DNA segment encoding influenza virus PB1, a vector for mRNA production comprising a promoter operably linked to a DNA segment encoding influenza virus PB2, and a vector for mRNA production comprising a promoter operably linked to a DNA segment encoding influenza virus NP, and optionally a vector for mRNA production comprising a promoter operably linked to a DNA segment encoding influenza virus HA, a vector for mRNA production comprising a promoter operably linked to a DNA segment encoding influenza virus NA, a vector for mRNA production comprising a promoter operably linked to a DNA segment encoding influenza virus M1, a vector for mRNA production comprising a promoter operably linked to a DNA segment encoding influenza virus M2, or a vector for mRNA production comprising a promoter operably linked to a DNA segment encoding influenza virus NS2.

Specifically, the NS1 encoding gene segment encodes a truncated NS1 protein or functionally knocked out or deleted NS1 protein as described herein.

In a further aspect provided herein is a method of making a virus described herein, wherein the method comprises introducing the recombinant vectors described herein and expressing an influenza virus particle as described herein in a reverse genetics system.

In a further embodiment, provided herein is a method of increasing growth rate of influenza viruses wherein said method comprises the step of introducing a modification into the influenza virus PB2, PB1, M and/or NS gene that results in a recombinant influenza virus described herein. Specifically, provided herein is a method, wherein the PB1, PB2, PA, NP, NS, and M DNAs in the vectors for vRNA productions have a sequence that corresponds to one that encodes a polypeptide having at least 98% amino acid sequence identity to a corresponding polypeptide encoded by SEQ ID Nos. 2, 4, 6, 8, 10, 12, 14, 16, 20, 24, 26, 28, 30, 32, 34, 37 and 38.

In a specific embodiment, provided herein is also a virus obtained by the method of the invention.

In one embodiment, the isolated recombinant influenza viruses comprise heterologous influenza virus NA and/or HA gene segments.

In an embodiment, A/IVR-116 may serve as genetic backbone for generating influenza virus vaccine, specifically H3N2 viruses, more specifically A/Hong Kong/4801/14 comprising gene segments encoding amino acid substitutions at positions specified herein.

Herein provided are influenza virus vectors as described herein, e.g., those useful to prepare reassortant viruses including 6:1:1 reassortants, 6:2 reassortants and 7:1 reassortants. A 6:1:1 reassortant according to the present invention is an influenza virus with 6 internal gene segments, an NA gene segment from a different, second, viral isolate, and a HA gene segment from a third isolate; a 6:2 reassortant is an influenza virus with 6 internal gene segments, and an NA gene segment and a HA gene segment from a different (second) viral isolate; and a 7:1 reassortant is an influenza virus with 6 internal gene segments and an NA gene segment from a vaccine virus, and a HA gene segment from a different viral source than the vaccine virus, or an influenza virus with 6 internal gene segments and a HA gene segment, and an NA gene segment is from a different viral source than the vaccine virus. As an alternative, 5:1:2 reassortants are also encompassed herein.

Specific examples of 6:2 reassortants are A/IVR-116: A/Hong Kong/4801/2014 comprising a functionally deleted NS1 protein or B/Thüringen/02/06:B/Murmansk/3/2010 comprising a functionally deleted NS1 protein.

According to a specific embodiment, the influenza virus may be of human or avian origin.

Viruses that may provide the internal genes for reassortants include viruses that have high titers in MDCK cells, e.g., titers of at least about $10^5$ PFU/mL; high titers in embryonated eggs, e.g. titers of at least about $10^7$ $EID_{50}$/mL, high titers in VERO cells, e.g. titers of at least about $10^7$ PFU/mL.

In one embodiment, the titers of the viruses of the invention in cells such as MDCK cells or Vero cells may be over 1 log, 2 logs, 3 logs, or greater, than titers of the corresponding virus without particular residues at the selected positions.

The respective measurements can be performed using an FFA assay, TCID50 and Plaque.

In an embodiment also vaccines comprising an immunogenicity inducing effective amount of recombinant virus as described herein in admixture with a pharmaceutically acceptable carrier are provided.

FIGURES

Figure 2:
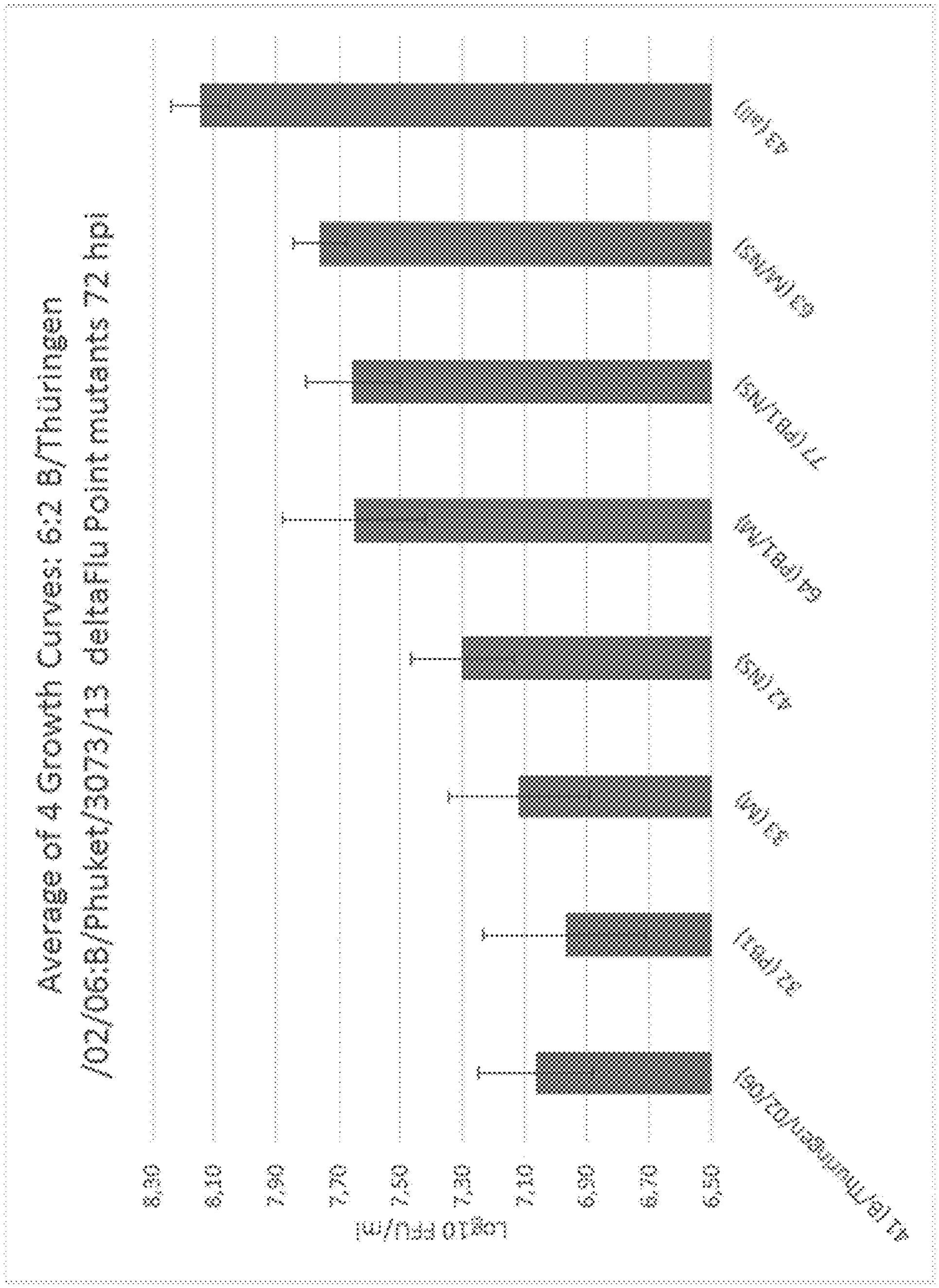
Figure 3:
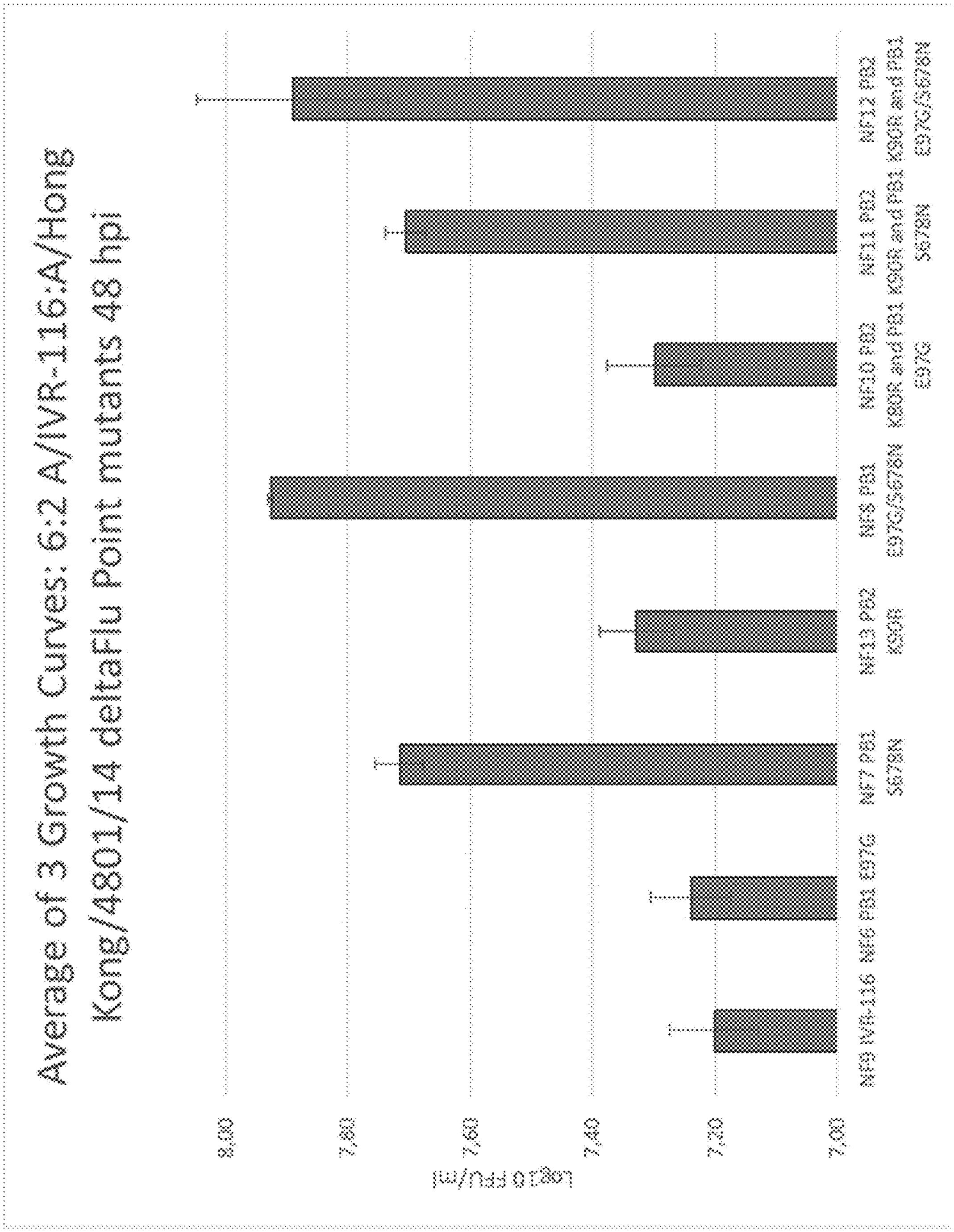

FIG. 1: Average of 3 Growth Curves: 6:2 B/Thüringen/02/06:B/Murmansk/3/10 deltaFlu Point mutants 72 hpi FIG. 2: Average of 4 Growth Curves: 6:2 B/Thüringen/02/06:B/Phuket/3073/13 deltaFlu Point mutants 72 hpi FIG. 3: Average of 3 Growth Curves: 6:2 A/IVR-116:A/Hong Kong/4801/14 deltaFlu Point mutants 48 hpi FIG. 4: Influenza sequences

DETAILED DESCRIPTION

As used herein the numbering of the modified amino acid positions refers to the numbering of the amino acid sequences of PB1, PB2, M1 and NS2 as provided herein with SEQ ID Nos. 2, 6, 10, 14, 26, 30, 32, 34, 37 and 38.

As used herein the numbering of the modified nucleotide positions refers to the numbering of the amino acid sequences of PB1, PB2, M1 and NS2 as provided herein with SEQ ID Nos. 1, 5, 9, 13, 25, 29, 31, 33, 35 and 36.

The terms “nucleic acid,” “polynucleotide,” “polynucleotide sequence” and “nucleic acid sequence” refer to single-stranded or double-stranded deoxyribonucleotide or ribonucleotide polymers, or chimeras or analogues thereof. As used herein, the term optionally includes polymers of analogs of naturally occurring nucleotides having the essential nature of natural nucleotides in that they hybridize to single-stranded nucleic acids in a manner similar to naturally occurring nucleotides (e.g., peptide nucleic acids). Unless otherwise indicated, a particular nucleic acid sequence of this invention encompasses complementary sequences, in addition to the sequence explicitly indicated.

As used herein, the term “gene” is used broadly to refer to any nucleic acid associated with a biological function. Thus, genes include coding sequences and/or the regulatory sequences required for their expression. The term “gene” applies to a specific genomic sequence, as well as to a cDNA or an mRNA encoded by that genomic sequence. Genes also include non-expressed nucleic acid segments that, for example, form recognition sequences for other proteins. Non-expressed regulatory sequences include “promoters” and “enhancers,” to which regulatory proteins such as transcription factors bind, resulting in transcription of adjacent or nearby sequences.

The term “vector” refers to the means by which a nucleic can be propagated and/or transferred between organisms, cells, or cellular components. Vectors include plasmids, viruses, bacteriophage, pro-viruses, phagemids, transposons, and artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that are not autonomously replicating. Most commonly, the vectors of the present invention are plasmids or linear expression constructs as described in WO20100063804A1.

An "expression vector" is a vector, such as a plasmid, which is capable of promoting expression, as well as replication of a nucleic acid incorporated therein. Typically, the nucleic acid to be expressed is "operably linked" to a promoter and/or enhancer, and is subject to transcription regulatory control by the promoter and/or enhancer. Also bi-directional vectors are encompassed by the term vector.

A "bi-directional expression vector" is typically characterized by two alternative promoters oriented in the opposite direction relative to a nucleic acid situated between the two promoters, such that expression can be initiated in both orientations resulting in, e.g., transcription of both plus (+) or sense strand, and negative (−) or antisense strand RNAs. Alternatively, the bi-directional expression vector can be an ambisense vector, in which the viral mRNA and viral genomic RNA (as a cRNA) are expressed from the same strand.

As used herein, the term "isolated" refers to an in vitro preparation and/or isolation of a nucleic acid molecule, e.g., a vector or plasmid, peptide or polypeptide (protein), or the virus of the invention, so that it is not associated with in vivo substances, or is substantially purified from in vitro substances. An isolated virus preparation is generally obtained by in vitro culture and propagation, and/or via passage in eggs, and is substantially free from other infectious agents.

As used herein, "substantially purified" means the object species is the predominant species, e.g., on a molar basis it is more abundant than any other individual species in a composition, and preferably is at least about 80% of the species present, and optionally 90% or greater, e.g., 95%, 98%, 99% or more, of the species present in the composition.

As used herein, "substantially free" means below the level of detection for a particular infectious agent using standard detection methods for that agent.

A "recombinant" virus is one which has been manipulated in vitro, e.g., using recombinant DNA techniques, to introduce changes to the viral genome. Reassortant viruses can be prepared by recombinant or non-recombinant techniques.

As used herein, the term "recombinant nucleic acid" or "recombinant DNA/RNA sequence or segment" refers to a nucleic acid, e.g., to DNA or RNA, that has been derived or isolated from a source, that may be subsequently chemically altered in vitro, so that its sequence is not naturally occurring, or corresponds to naturally occurring sequences that are not positioned as they would be positioned in the native genome. An example of DNA "derived" from a source would be a DNA sequence that is identified as a useful fragment, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

As used herein, a "heterologous" influenza virus gene or gene segment is from an influenza virus source that is different than a majority of the other influenza viral genes or gene segments in a recombinant, e.g., reassortant, influenza virus.

The terms "isolated polypeptide", "isolated peptide" or "isolated protein" include a polypeptide, peptide or protein encoded by cDNA or recombinant RNA including one of synthetic origin, or some combination thereof.

The term "recombinant protein" or "recombinant polypeptide" as used herein refers to a protein molecule expressed from a recombinant DNA molecule. In contrast, the term "native protein" is used herein to indicate a protein isolated from a naturally occurring (i.e., a non-recombinant) source. Molecular biological techniques may be used to produce a recombinant form of a protein with identical properties as compared to the native form of the protein.

Amino acid modifications refer to the exchange (substitution) of amino acids of the same polarity and/or charge but can also be of different polarity and/or charge. In this regard, amino acids refer to twenty naturally occurring amino acids encoded by sixty-four triplet codons. These 20 amino acids can be split into those that have neutral charges, positive charges, and negative charges:

The "neutral" amino acids are shown below along with their respective three-letter and single-letter code and polarity:

Alanine: (Ala, A) nonpolar, neutral;
Asparagine: (Asn, N) polar, neutral;
Cysteine: (Cys, C) nonpolar, neutral;
Glutamine: (Gln, Q) polar, neutral;
Glycine: (Gly, G) nonpolar, neutral;
Isoleucine: (Ile, I) nonpolar, neutral;
Leucine: (Leu, L) nonpolar, neutral;
Methionine: (Met, M) nonpolar, neutral;
Phenylalanine: (Phe, F) nonpolar, neutral;
Proline: (Pro, P) nonpolar, neutral;
Serine: (Ser, S) polar, neutral;
Threonine: (Thr, T) polar, neutral;
Tryptophan: (Trp, W) nonpolar, neutral;
Tyrosine: (Tyr, Y) polar, neutral;
Valine: (Val, V) nonpolar, neutral; and
Histidine: (His, H) polar, positive (10%) neutral (90%).

The "positively" charged amino acids are:
Arginine: (Arg, R) polar, positive; and
Lysine: (Lys, K) polar, positive.

The "negatively" charged amino acids are:
Aspartic acid: (Asp, D) polar, negative; and
Glutamic acid: (Glu, E) polar, negative.

Within the scope of the invention, the term "cells" or "cell culture" means the cultivation of individual cells, tissues, organs, insect cells, avian cells, mammalian cells, hybridoma cells, primary cells, continuous cell lines, and/or genetically engineered cells, such as recombinant cells expressing a recombinant influenza virus or influenza virus vector described herein, optionally expressing a heterologous gene of interest. These can be for example BSC-1 cells, LLC-MK cells, CV-1 cells, CHO cells, COS cells, murine cells, human cells, HeLa cells, 293 cells, VERO cells, MDBK cells, MDCK cells, MDOK cells, CRFK cells, RAF cells, TCMK cells, LLC-PK cells, PK15 cells, WI-38 cells, MRC-5 cells, T-FLY cells, BHK cells, SP2/0 cells, NS0, PerC6 (human retina cells), chicken embryo cells or derivatives, embryonated egg cells, embryonated chicken eggs or derivatives thereof.

A number of mammalian cell lines are known in the art and include Vero cells (anchorage dependent or suspension grown), PER.C6, HEK cells, human embryonic kidney cells (293 cells), HeLa cells, CHO cells, avian cells (continuous or primary), Vero cells being preferred for the method of the invention.

The cells may be cultivated in any system applicable for propagating influenza virus in said cells. Specifically the medium can be supplemented with antibiotics such as amphothericin B.

The recombinant influenza virus described herein is useful as master donor virus (MDV). The MDV thus comprises one or more of the herein modified M1, PB1, PB2 and NS2 proteins together with the other segments and PA and NP from a common MDV such as B/Thüringen, A/IVR-116, Jiangsu or virus from Yamagata lineage as described herein. Typically, a single MDV strain is selected for each of the A and B subtypes. In the case of a live attenuated vaccine, the MDV strain is typically chosen for its favorable properties, e.g., temperature sensitivity, cold adaptation and/or attenuation, relative to vaccine production. For example, a selected master donor type A virus (MDV-A), or master donor type B virus (MDV-B), is produced from a plurality of cloned viral cDNAs constituting the viral genome. In an exemplary embodiment, recombinant viruses are produced from eight cloned viral cDNAs. Eight viral cDNAs representing either the selected MDV-A or MDV-B sequences of PB2, PB 1, PA, NP, HA, NA, M and NS are cloned into a bi-directional expression vector, such as a plasmid or liner expression construct, such that the viral genomic RNA can be transcribed from an RNA polymerase I (pol I) promoter from one strand and the viral mRNAs can be synthesized from an RNA polymerase II (pol II) promoter from the other strand. Optionally, any gene segment can be modified, including the HA segment (e.g., to remove the multi-basic cleavage site). Infectious recombinant MDV-A or MDV-B virus is then recovered following transfection of plasmids bearing the eight viral cDNAs into appropriate host cells, e.g., Vero cells, or MDCK cells. Using the plasmids and methods described herein, the invention is useful, e.g., for generating 6:2 reassortant influenza vaccines by co-transfection of the 6 internal genes (PB1, PB2, PA, NP, M and NS), containing the specific amino acid modifications as described herein, of the selected virus (e.g., MDV-A, MDV-B) together with the HA and NA derived from different corresponding type (A or B) influenza viruses. For example, the HA segment is favorably selected from a pathogenically relevant H1, H3 or B strain, as is routinely performed for vaccine production. Similarly, the HA segment can be selected from a strain with emerging relevance as a pathogenic strain such as an H2 strain (e.g., H2N2), an H5 strain (e.g., H5N1) or an H7 strain (e.g., H7N7). Reassortants incorporating seven genome segments of the MDV and either the HA or NA gene of a selected strain (7:1 reassortants) can also be produced.

Non-limiting examples of influenza B virus include strains and clinical isolates such as, but not limited to B/Thüringen, B/Colorado, B/Maryland, B/Iowa or B/Phuket. A vaccine of the invention comprises an isolated recombinant influenza virus of the invention, and optionally one or more other components such as other isolated viruses including influenza viruses, one or more immunogenic proteins or glycoproteins of one or more isolated influenza viruses or one or more other pathogens, e.g. from bacteria, non-influenza viruses, yeast or fungi, or isolated nucleic acid encoding one or more viral proteins. In one embodiment, the influenza viruses of the invention may be vaccine vectors for influenza virus or heterologous sequences such as, but not limited to, cytokines, chemokines, growth factors or pathogens.

A complete virus vaccine may be concentrated by ultrafiltration and then purified by zonal centrifugation or by chromatography. Viruses other than the virus of the invention, such as those included in a multivalent vaccine, may be inactivated before or after purification using formalin or beta-propiolactone, for instance.

A subunit vaccine comprises purified glycoproteins. Such a vaccine may be prepared as follows: using viral suspensions fragmented by treatment with detergent, the surface antigens are purified, by ultracentrifugation for example. The subunit vaccines thus contain mainly HA protein, and also NA. The detergent used may be cationic detergent for example, such as hexadecyl trimethyl ammonium bromide, an anionic detergent such as ammonium deoxycholate; or a nonionic detergent such as TRITON X100. The hemagglutinin may also be isolated after treatment of the virions with a protease such as bromelin, and then purified. The subunit vaccine may be combined with an influenza virus of the invention in a multivalent vaccine.

A split vaccine comprises virions, entire virus particles, which have been subjected to treatment with agents that dissolve lipids. A split vaccine can be prepared as follows: an aqueous suspension of the purified virus obtained as above, inactivated or not, is treated, under stirring, by lipid solvents such as ethyl ether or chloroform, associated with detergents. The dissolution of the viral envelope lipids results in fragmentation of the viral particles. The aqueous phase is recuperated containing the split vaccine, constituted mainly of hemagglutinin and neuraminidase with their original lipid environment removed, and the core or its degradation products. Then the residual infectious particles are inactivated if this has not already been done. The split vaccine may be combined with an attenuated virus of the invention in a multivalent vaccine.

Inactivated influenza virus vaccines are provided by inactivating replicated virus using known methods, such as, but not limited to, formalin or 3-propiolactone treatment. Inactivated vaccine types that can be used in the invention can include whole-virus vaccines or subvirion (split) vaccines. The whole virus vaccine contains intact, inactivated virus, while the split vaccine contains purified virus disrupted with detergents that solubilize the lipid-containing viral envelope, followed by chemical inactivation of residual virus.

The influenza virus as described herein may also comprise a heterologous gene or open reading frame of interest, such as a foreign gene encoding an immunogenic peptide or protein useful as a vaccine or in gene replacement, for instance, may encode an epitope useful in a cancer therapy or vaccine, or a peptide or polypeptide useful in gene therapy. When preparing the influenza virus, the vector or plasmid comprising the gene or cDNA of interest may substitute for a vector or plasmid for an influenza viral gene or may be in addition to vectors or plasmids for all influenza viral genes.

Thus, another embodiment of the invention comprises a composition or plurality of vectors as described above in which one of the vectors is replaced with, or further comprises, 5' influenza virus sequences optionally including 5' influenza virus coding sequences or a portion thereof, linked to a desired nucleic acid sequence, e.g., a desired cDNA, linked to 3' influenza virus sequences optionally including 3' influenza virus coding sequences or a portion thereof. In one embodiment, the desired nucleic acid sequence such as a cDNA is in an antisense (antigenomic) orientation. The introduction of such a vector in conjunction with the other vectors described above to a host cell permissive for influenza virus replication results in recombinant virus comprising vRNA corresponding to the heterologous sequences of the vector.

Additionally, vaccines also include those containing the isolated HA and NA surface proteins, which are referred to as surface antigen or subunit vaccines. Live, attenuated influenza virus vaccines, such as those including a recombinant virus of the invention can be used for preventing or treating influenza virus infection.

The influenza virus according to the invention comprises a deletion or modification within the NS1 gene (ANSI virus, deINS1 virus) as described in WO99/64571 and WO99/64068. These viruses are replication deficient as they undergo abortive replication in the respiratory tract of animals. Upon intranasal administration, the vaccine virus is able to initiate abortive infection in mucosal tissues, without the effect of viral shedding. At the same time the virus stimulates local cytokine response and evokes a T-cell mediated protective immune response.

According to the invention, the term "replication deficient" is defined as replication rate in interferon competent host cells that is at least less than 5%, preferably less than 1%, preferably less than 0.1% compared to wild type influenza virus replication rate, determined by hemagglutination assay, TCID50 assay or plaque assay as well known in the art.

The term "lacking the functional NS1 protein" refers to influenza virus which is replication deficient, i.e. its replication rate in interferon competent host cells that is at least less than 5%, preferably less than 1%, preferably less than 0.1% compared to wild type influenza virus replication rate, determined by hemagglutination assay, TCID50 assay or plaque assay as well known in the art.

In an embodiment, the NS1 protein comprises a deletion of at least 60% of the NS1 amino acids, preferably of at least 70%, more preferably of at least 90%. Alternatively, the functionality of the NS1 protein can be completely diminished. The NS1 protein can lack the functional RNA binding domain and/or the carboxy terminal domain or both domains of the influenza B NS1 protein thus rendered non-functional. This domain can be completely or partially deleted as well as amino acids can be substituted or inserted and the remaining domain can be tested for functionality as described in the art (Dauber et al, J Virol. 2006, December; 80(23): 11667-77).

In an alternative embodiment, the influenza virus vector comprises a truncated NS1 protein that contains up to 122 amino acids, preferably up to 121 amino acids, preferably up to 120 amino acids, preferably up to 119 amino acids, preferably up to 118 amino acids, preferably up to 117 amino acids, preferably up to 116 amino acids, preferably up to 115 amino acids, preferably up to 114 amino acids, preferably up to 113 amino acids, preferably up to 112 amino acids, preferably up to 111 amino acids, preferably up to 110 amino acids, preferably up to 109 amino acids, preferably up to 108 amino acids, preferably up to 107 amino acids, preferably up to 106 amino acids, preferably up to 105 amino acids, preferably up to 104 amino acids, preferably up to 103 amino acids, preferably up to 102 amino acids, preferably up to 101 amino acids, preferably up to 100 amino acids, preferably up to 99 amino acids, preferably up to 98 amino acids, preferably up to 97 amino acids, preferably up to 96 amino acids, preferably up to 95 amino acids, preferably up to 94 amino acids, preferably up to 93 amino acids, preferably up to 92 amino acids, preferably up to 91 amino acids, preferably up to 90 amino acids, preferably up to 89 amino acids, preferably up to 88 amino acids, preferably up to 87 amino acids, preferably up to 86 amino acids, preferably up to 85 amino acids, preferably up to 84 amino acids, preferably up to 83 amino acids, preferably up to 82 amino acids, preferably up to 81 amino acids, preferably up to 80 amino acids, preferably up to 79 amino acids, preferably up to 78 amino acids, preferably up to 77 amino acids, preferably up to 76 amino acids, preferably up to 75 amino acids, preferably up to 74 amino acids, preferably up to 73 amino acids of the N-terminus of the NS1 protein.

In a specific embodiment, the influenza virus comprises an NS gene encoding a truncated NS1 protein of up to 123 amino acids, specifically up to 117 amino acids of the N-terminus of the respective wild type NS1 protein, thereby efficiently replicating in IFN-sensitive tumor cells while being attenuated and replication-deficient in normal, non-tumor cells. More specifically, the virus comprises 106 amino acids of the N-terminus of the respective wild type NS1 protein.

It was demonstrated that deletion of the NS1 protein or functional knock-out of the protein leads to a significant attenuation of influenza virus due to lack of replication in interferon competent cells or organisms (replication deficient phenotype). Viruses lacking the NS1 protein are not able to antagonize cytokine production of infected cells, therefore inducing self-adjuvanting and immune modulating effects. The hallmark of immune response after immunization with DeINS1 virus is triggering of Th1 type of immune response associated with predominant IgG2A antibody isotype response (Ferko B. et al. J. Virol., 80(23), 2006, pp. 11621-11627).

Since resistance to influenza virus is mediated primarily by the development of an immune response to the HA and/or NA glycoproteins, the genes coding for these surface antigens come from the reassorted viruses or clinical isolates. The attenuated genes are derived from an attenuated parent. In this approach, genes that confer attenuation generally do not code for the HA and NA glycoproteins.

Viruses (donor influenza viruses) are available that are capable of reproducibly attenuating influenza viruses, e.g., a cold adapted (ca) donor virus can be used for attenuated vaccine production. Live, attenuated reassortant virus vaccines can be generated by mating the ca donor virus with a virulent replicated virus. Reassortant progeny are then selected at 25° C. (restrictive for replication of virulent virus), in the presence of an appropriate antiserum, which inhibits replication of the viruses bearing the surface antigens of the attenuated ca donor virus. Useful reassortants are infectious, attenuated for seronegative non-adult mammals and immunologically primed adult mammals, immunogenic and genetically stable.

Other attenuating mutations can be introduced into influenza virus genes by site-directed mutagenesis to rescue infectious viruses bearing these mutant genes. Attenuating mutations can be introduced into non-coding regions of the genome, as well as into coding regions. Such attenuating mutations can also be introduced into genes other than the HA or NA, e.g., the PB2 polymerase gene. Thus, new donor viruses can also be generated bearing attenuating mutations introduced by site-directed mutagenesis, and such new donor viruses can be used in the production of live attenuated reassortant vaccine candidates in a manner analogous to that described above for the ca donor virus. Similarly, other known and suitable attenuated donor strains can be reassorted with influenza virus to obtain attenuated vaccines suitable for use in the vaccination of mammals.

In one embodiment, such attenuated viruses maintain the genes from the virus that encode antigenic determinants substantially similar to those of the original clinical isolates. The purpose of the attenuated vaccine is to provide substantially the same antigenicity as the original clinical isolate of the virus, while at the same time lacking pathogenicity to the degree that the vaccine causes minimal chance of inducing a serious disease condition in the vaccinated mammal.

The viruses in a multivalent vaccine can thus be attenuated or inactivated, formulated and administered, according to known methods, as a vaccine to induce an immune response in an animal, e.g., a mammal. Methods are well-known in the art for determining whether such attenuated or inactivated vaccines have maintained similar antigenicity to that of the clinical isolate or high growth strain derived therefrom. Such known methods include the use of antisera or antibodies to eliminate viruses expressing antigenic determinants of the donor virus; chemical selection (e.g., amantadine or rimantidine); HA and NA activity and inhibition; and nucleic acid screening (such as probe hybridization or PCR) to confirm that donor genes encoding the antigenic determinants (e.g. HA or NA genes) are not present in the attenuated viruses.

Pharmaceutical compositions of the present invention, suitable for inoculation, e.g., nasal, mucosal, parenteral or oral administration, comprise one or more influenza virus isolates, e.g., one or more attenuated or inactivated influenza viruses, a subunit thereof, isolated protein(s) thereof, and/or isolated nucleic acid encoding one or more proteins thereof, optionally further comprising sterile aqueous or non-aqueous solutions, suspensions, and emulsions. The compositions can further comprise auxiliary agents or excipients, as known in the art. The composition of the invention is generally presented in the form of individual doses (unit doses).

Conventional vaccines generally contain about 0.1 to 200 μg, e.g. 30 to 100 μg, of HA from each of the strains entering into their composition. The vaccine forming the main constituent of the vaccine composition of the invention may comprise a single influenza virus, or a combination of influenza viruses, for example, at least two or three influenza viruses, including one or more reassortant(s).

Preparations for parenteral administration include sterile aqueous or non-aqueous solutions, suspensions, and/or emulsions, which may contain auxiliary agents or excipients known in the art.

When a composition of the present invention is used for administration to an individual, it can further comprise salts, buffers, adjuvants, or other substances which are desirable for improving the efficacy of the composition.

The composition can also contain variable but small quantities of endotoxin-free formaldehyde, and preservatives, which have been found safe and not contributing to undesirable effects in the organism to which the composition is administered.

The administration of the composition may be for either a "prophylactic" or "therapeutic" purpose.

Specifically, the term "therapy" refers to therapeutic measures which are intended to encompass administration to cure the disease or reduce the symptoms of disease.

Specifically, the term "prophylaxis" refers to preventive measures which are intended to reduce the risk of disease occurrence, or recurrence of disease.

When provided prophylactically, the compositions of the invention which are vaccines are provided before any symptom or clinical sign of a pathogen infection becomes manifest. The prophylactic administration of the composition serves to prevent or attenuate any subsequent infection. When provided prophylactically, the composition of the invention, is provided before any symptom or clinical sign of a disease becomes manifest. The prophylactic administration of the composition serves to prevent or attenuate one or more symptoms or clinical signs associated with the disease.

When provided therapeutically, a viral vaccine is provided upon the detection of a symptom or clinical sign of actual infection.

Thus, a vaccine composition of the present invention may be provided either before the onset of infection (so as to prevent or attenuate an anticipated infection) or after the initiation of an actual infection.

A "pharmacologically acceptable" composition refers to a composition that can be tolerated by a recipient mammal. Such a composition is said to be administered in a "therapeutically effective amount" if the amount administered is physiologically significant. A composition of the present invention is physiologically significant if its presence results in a detectable change in the physiology of a recipient subject, e.g., enhances at least one primary or secondary humoral or cellular immune response against at least one strain of an infectious influenza virus.

The "protection" provided need not be absolute, i.e., an influenza infection need not be totally prevented or eradicated, as long as there is a statistically significant improvement compared with a control population or set of mammals, specifically of humans. Protection may be limited to reducing the severity or rapidity of onset of symptoms or clinical signs of the influenza virus infection.

A composition of the present invention may confer resistance to one or more pathogens, e.g. one or more influenza virus strains, by either passive immunization or active immunization. In active immunization, an attenuated live vaccine composition is administered prophylactically to a subject (e.g., a mammal), and the subject's immune response to the administration provides protection against infection and/or disease. For passive immunization, the antisera can be recovered and administered to a recipient suspected of having an infection caused by at least one influenza virus strain.

As referred herein, a vaccine is said to prevent or attenuate a disease if its administration results either in the total or partial attenuation (i.e., suppression) of a clinical sign or condition of the disease, or in the total or partial immunity of the individual to the disease.

A composition having at least one influenza virus of the present invention, including one which is attenuated and one or more other isolated viruses, one or more isolated viral proteins thereof, one or more isolated nucleic acid molecules encoding one or more viral proteins thereof, or a combination thereof, may be administered by any means that achieve the intended purposes.

For example, administration of such a composition may be by various parenteral routes such as subcutaneous, intravenous, intradermal, intramuscular, intraperitoneal, intranasal, oral or transdermal routes. Parenteral administration can be accomplished by bolus injection or by gradual perfusion over time.

A typical regimen for preventing, suppressing, or treating an influenza virus related pathology, comprises administration of an effective amount of a vaccine composition as described herein, administered as a single treatment, or repeated as enhancing or booster dosages, over a period up to and including between one week and about 24 months, or any range or value therein.

According to the present invention, an "effective amount" of a composition is one that is sufficient to achieve a desired effect. It is understood that the effective dosage may be dependent upon the species, age, sex, health, and weight of the recipient, kind of concurrent treatment, if any, frequency of treatment, and the nature of the effect wanted. The ranges of effective doses provided below are not intended to limit the invention and represent dose ranges.

The dosage of a live, attenuated or killed virus vaccine for an animal such as a mammalian adult organism may be from about $10^2$-$10^{15}$, e.g., $10^3$-$10^{12}$, plaque forming units (PFU)/kg, or any range or value therein. The dose of inactivated vaccine may range from about 0.1 to 1000, e.g., 30 to 100 μg, of HA protein. However, the dosage should be a safe and effective amount as determined by conventional methods, using existing vaccines as a starting point.

The dosage of immunoreactive HA in each dose of replicated virus vaccine may be standardized to contain a suitable amount, e.g., 30 to 100 μg or any range or value therein, or the amount recommended by government agencies or recognized professional organizations. The quantity of NA can also be standardized; however, this glycoprotein may be labile during purification and storage.

The dosage of immunoreactive HA in each dose of replicated virus vaccine can be standardized to contain a suitable amount, e.g., 1-50 μg or any range or value therein, or the amount recommended by the U.S. Public Health Service (PHS), which is usually 15 μg, per component for older children >3 years of age, and 7.5 μg per component for older children <3 years of age. Each 0.5-ml dose of vaccine may contain approximately 1-50 billion virus particles, and preferably 10 billion particles.

The influenza virus can be selected from the group of human influenza virus, avian influenza virus, equine influenza virus, swine influenza virus, feline influenza virus. Influenza virus is from strains A and B. Influenza antigens may be derived from interpandemic (annual or seasonal) influenza strains. Alternatively, influenza antigens may be derived from strains with the potential to cause a pandemic outbreak; i.e., influenza strains with new hemagglutinin compared to hemagglutinin in currently circulating strains, or influenza strains which are pathogenic in avian subjects and have the potential to be transmitted horizontally in the human population or influenza strains which are pathogenic to humans.

Specifically, influenza A viruses can be categorized into two phylogenetic groups (group 1 and group 2; Joyce M G. et al., Cell 166, 609-623, 2016), each containing diverse subtypes. Currently, group 1 influenza viruses from the H1 subtype (1918 and 2009 H1N1 pandemics), and the group 2 H3 subtype (1968 H3N2 pandemic), co-circulate and cause seasonal infections in over 10% of the human population each year. Other subtypes include the group 1 H2 subtype, endemic in humans from 1957-1968, the group 1 H5 subtype, including lethal avian strains and the group 1 H6 and H9 and the group 2 H7 and H10 subtypes, Potential approaches to a universal influenza vaccine involve the elicitation of neutralizing antibodies that recognize the influenza hemagglutinin (HA) from multiple subtypes.

Gene segments for of PB1, PB2, M and/or NS that have the residues at the specified positions may be combined with a gene segment for HA, e.g., H1, H2, H3, H4, H5, H6, H7, H8, H9, H10, H11, H12, H13, H14, H15, H16, or H17 and a gene segment for NA, e.g., N1, N2, N3, N4, N5, N6, N7, N8, N9, or N10, and any combination of HA and NA, to provide the reassortant vaccine viruses of the invention. Non-limiting examples of influenza A viruses include subtype H10N4, H10N5, H10N7, H10N8, H10N9, H11N1, H11N13, H11N2, H11N4, H11N6, H11N8, H11N9, H12N1, H12N4, H12N5, H12N8, H13N2, H13N3, H13N6, H13N7, H14N5, H14N6, H15N8, H15N9, H16N3, H1N1, H1N2, H1N3, H1N6, H1N9, H2N1, H2N2, H2N3, H2N5, H2N7, H2N8, H2N9, H3N1, H3N2, H3N3, H3N4, H3N5, H3N6, H3N8, H3N9, H4N1, H4N2, H4N3, H4N4, H4N5, H4N6, H4N8, H4N9, H5N1, H5N2, H5N3, H5N4, H5N6, H5N7, H5N8, H5N9, H6N1, H6N2, H6N3, H6N4, H6N5, H6N6, H6N7, H6N8, H6N9, H7N1, H7N2, H7N3, H7N4, H7N5, H7N7, H7N8, H7N9, H8N4, H8N5, H9N1, H9N2, H9N3, H9N5, H9N6, H9N7, H9N8, and H9N9.

The invention further encompasses following items:

1. A recombinant influenza B virus comprising M, PB and NS gene segments comprising one or more nucleotide modifications resulting in
   - an M1 protein having an amino acid substitution at position 89 and/or 93, according to the numbering of SEQ ID No. 6, and/or
   - an NS2 protein having an amino acid substitution at positions 75, 76 and/or 117, according to the numbering of SEQ ID No. 10, and/or
   - a PB2 protein having an amino acid substitution at position 427 according to the numbering of SEQ ID No. 2 and/or
   - a PB1 protein having an amino acid substitution at position 67 according to the numbering of SEQ ID No. 14, or
   - any combinations thereof.

2. A recombinant influenza B virus of item 1 comprising M and NS gene segments which contain nucleotide modifications encoding
   - an M1 protein having an amino acid substitution at position 89, according to the numbering of SEQ ID No. 6,
   - an NS2 protein having an amino acid substitution at position 76, according to the numbering of SEQ ID No. 10.

3. The recombinant influenza B virus according to item 1, further comprising a PB2 gene encoding a PB2 protein having an amino acid substitution at position 427 according to the numbering of SEQ ID No. 2.

4. The recombinant influenza B virus according to item 2 or 3, further comprising an NS gene encoding an NS2 protein having an amino acid substitution at position 75 according to the numbering of SEQ ID No. 10.

5. The recombinant influenza B virus according to item 2 to 4, comprising
   - an M1 protein having an amino acid substitution at position 89, according to the numbering of SEQ ID No. 6, specifically having serine at amino acid position 89;
   - a PB2 protein having an amino acid substitution at position 427 according to the numbering of SEQ ID No. 2, specifically having serine at amino acid position 427; and
   - an NS2 protein having amino acid substitutions at positions 75 and/or 76, according to the numbering of SEQ ID No. 10, specifically having glycine at amino acid position 76 and/or arginine at amino acid position 75.

6. The recombinant influenza B virus of any one of items 2 to 5, comprising the amino acid sequences SEQ ID No. 4, SEQ ID No. 8 and SEQ ID No. 12.

7. The recombinant influenza B virus according to any one of items 2 to 6, comprising the nucleotide sequences SEQ ID No. 3, SEQ ID No. 7, and SEQ ID No. 11.

8. A recombinant influenza B virus comprising PB1, M and NS genes which contain at least two nucleotide modifications encoding a PB1 protein having an amino acid substitution at position 67 according to the numbering of SEQ ID No. 14, an M1 protein having an amino acid substitution at position 93 according to the numbering of SEQ ID No. 6, and/or an NS2 protein having an amino acid substitution at position 117 according to the numbering of SEQ ID No. 10.

9. The recombinant influenza B virus according to item 7, comprising modified proteins selected from the group consisting of a PB1 protein having asparagine at amino acid position 67, an M1 protein having arginine at amino acid position 93, and/or an NS2 protein having histidine at amino acid position 117.

10. The recombinant influenza B virus of item 7 or 8, comprising a PB1 protein having an amino acid substitution at position 67 according to the numbering of SEQ ID No. 14, an M1 protein having an amino acid substitution at position 93 according to the numbering of SEQ ID No. 6, and an NS2 protein having an amino acid substitution at position 117 according to the numbering of SEQ ID No. 10.

11. The recombinant influenza B virus according to items 7 to 9, comprising at least two of the amino acid sequences SEQ ID No. 16, SEQ ID No. 20 and SEQ ID No. 24.

12. The recombinant influenza B virus according to any one of items 8 to 10, comprising at least two nucleotide sequences of SEQ ID No. 15, SEQ ID No. 19 and SEQ ID No. 23.

13. A recombinant influenza A virus comprising PB1 and PB2 genes which contain at least two nucleotide modifications encoding a PB1 protein having an amino acid substitution at position 97 and 678 according to the numbering of SEQ ID No. 30, and/or a PB2 protein having an amino acid substitution at position 80 according to the numbering of SEQ ID No. 26.

14. The recombinant influenza A virus of item 12, comprising a PB1 protein having glycine at amino acid position 97 and asparagine at amino acid position 678, and/or a PB2 protein having arginine at amino acid position 80.

15. The recombinant influenza A virus according to items 12 or 13, comprising at least one nucleotide sequence as shown in any one of SEQ ID Nos 27 and 31.

16. The recombinant influenza A virus according to item 12 or 13, comprising at least one amino acid sequence of SEQ ID Nos 28 and 32.

17. The recombinant influenza virus according to any one of items 1 to 15, wherein said virus is a reassortant virus, specifically wherein said virus comprises at least two gene segments of a seasonal or pandemic strain origin.

18. The recombinant influenza virus according to any one of items 1 to 16, wherein the virus is attenuated or replication deficient, preferably it is completely replication deficient.

19. The recombinant influenza virus according to any one of items 1 to 17, wherein the virus comprises one or more modifications within the HA and/or NA genes.

20. The recombinant influenza according to any one of items 1 to 18, further comprising a modified NS1 gene segment which codes for an NS1 protein lacking a functional RNA binding domain and a functional carboxy terminal domain.

21. A vaccine composition comprising an immunogenicity inducing effective amount of influenza virus according to any one of items 1 to 19 in admixture with a pharmaceutically acceptable carrier.

22. An isolated nucleic acid encoding the recombinant influenza virus according to any one of items 1 to 19.

23. The influenza virus according to any one of items 1 to 19 for use in the manufacture of a medicament.

24. The influenza virus according to any one of items 1 to 19 for use in therapeutic or prophylactic treatment of an influenza virus infection.

25. A plurality of influenza virus vectors for preparing a reassortant influenza B virus according to any one of items 1 to 6, comprising a) a vector for vRNA production comprising a promoter operably linked to an influenza virus PA DNA linked to a transcription termination sequence, a vector for vRNA production comprising a promoter operably linked to an influenza virus PB1 DNA linked to a transcription termination sequence, a vector for vRNA production comprising a promoter operably linked to an influenza virus PB2 DNA linked to a transcription termination sequence, a vector for vRNA production comprising a promoter operably linked to an influenza virus HA DNA linked to a transcription termination sequence, a vector for vRNA production comprising a promoter operably linked to an influenza virus NP DNA linked to a transcription termination sequence, a vector for vRNA production comprising a promoter operably linked to an influenza virus NA DNA linked to a transcription termination sequence, a vector for vRNA production comprising a promoter operably linked to an influenza virus M DNA linked to a transcription termination sequence, and a vector for vRNA production comprising a promoter operably linked to an influenza virus NS cDNA or part thereof linked to a transcription termination sequence, wherein the PB1, PB2, PA, NP, NS, and M DNAs in the vectors for vRNA production encode at least one of: M1 with a serine at position 89, NS2 with glycine at position 76, NS2 with an arginine at position 75, PB2 serine at position 427, and optionally b) a vector for mRNA production comprising a promoter operably linked to a DNA segment encoding influenza virus PA, a vector for mRNA production comprising a promoter operably linked to a DNA segment encoding influenza virus PB1, a vector for mRNA production comprising a promoter operably linked to a DNA segment encoding influenza virus PB2, and a vector for mRNA production comprising a promoter operably linked to a DNA segment encoding influenza virus NP, and optionally a vector for mRNA production comprising a promoter operably linked to a DNA segment encoding influenza virus HA, a vector for mRNA production comprising a promoter operably linked to a DNA segment encoding influenza virus NA, a vector for mRNA production comprising a promoter operably linked to a DNA segment encoding influenza virus M1, a vector for mRNA production comprising a promoter operably linked to a DNA segment encoding influenza virus M2, or a vector for mRNA production comprising a promoter operably linked to a DNA segment encoding influenza virus NS2.

26. A plurality of influenza virus vectors for preparing a reassortant influenza B virus according to any one of items 7 to 11, comprising a) a vector for vRNA production comprising a promoter operably linked to an influenza virus PA DNA linked to a transcription termination sequence, a vector for vRNA production comprising a promoter operably linked to an influenza virus PB1 DNA linked to a transcription termination sequence, a vector for vRNA production comprising a promoter operably linked to an influenza virus PB2 DNA linked to a transcription termination sequence, a vector for vRNA production comprising a promoter operably linked to an influenza virus HA DNA linked to a transcription termination sequence, a vector for vRNA production comprising a promoter operably linked to an influenza virus NP DNA linked to a transcription termination sequence, a vector for vRNA production comprising a promoter operably linked to an influenza virus NA DNA linked to a transcription termination sequence, a vector for vRNA production comprising a promoter operably linked to an influenza virus M DNA linked to a transcription termination sequence, and a vector for vRNA production comprising a promoter operably linked to an influenza virus NS cDNA or part thereof linked to a transcription termination sequence, wherein the PB1, PB2, PA, NP, NS, and M DNAs in the vectors for vRNA production encode at least one of: M1 with an arginine at position 93, NS2 with histidine at position 117, PB1 with an asparagine at position 67, b) a vector for mRNA production comprising a promoter operably linked to a DNA segment encoding influenza virus PA, a vector for mRNA production comprising a promoter operably linked to a DNA segment encoding influenza virus PB1, a vector for mRNA production comprising a promoter operably linked to a DNA segment encoding influenza virus PB2, and a vector for mRNA production comprising a promoter operably linked to a DNA segment encoding influenza virus NP, and optionally a vector for mRNA production comprising a promoter operably linked to a DNA segment encoding influenza virus HA, a vector for mRNA production comprising a promoter operably linked to a DNA segment encoding influenza virus NA, a vector for mRNA production comprising a promoter operably linked to a DNA segment encoding influenza virus M1, a vector for mRNA production comprising a promoter operably linked to a DNA segment encoding influenza virus M2, or a vector for mRNA production comprising a promoter operably linked to a DNA segment encoding influenza virus NS2.

27. A plurality of influenza virus vectors for preparing a reassortant influenza A virus according to any one of items 12 to 13, comprising a) a vector for vRNA production comprising a promoter operably linked to an influenza virus PA DNA linked to a transcription termination sequence, a vector for vRNA production comprising a promoter operably linked to an influenza virus PB1 DNA linked to a transcription termination sequence, a vector for vRNA production comprising a promoter operably linked to an influenza virus PB2 DNA linked to a transcription termination sequence, a vector for vRNA production comprising a promoter operably linked to an influenza virus HA DNA linked to a transcription termination sequence, a vector for vRNA production comprising a promoter operably linked to an influenza virus NP DNA linked to a transcription termination sequence, a vector for vRNA production comprising a promoter operably linked to an influenza virus NA DNA linked to a transcription termination sequence, a vector for vRNA production comprising a promoter operably linked to an influenza virus M DNA linked to a transcription termination sequence, and a vector for vRNA production comprising a promoter operably linked to an influenza virus NS cDNA or part thereof linked to a transcription termination sequence, wherein the PB1, PB2, PA, NP, NS, and M DNAs in the vectors for vRNA production encode at least one of: PB1 with a glycine at position 97, PB1 with an asparagine at position 678, PB2 with arginine at position 80, b) a vector for mRNA production comprising a promoter operably linked to a DNA segment encoding influenza virus PA, a vector for mRNA production comprising a promoter operably linked to a DNA segment encoding influenza virus PB1, a vector for mRNA production comprising a promoter operably linked to a DNA segment encoding influenza virus PB2, and a vector for mRNA production comprising a promoter operably linked to a DNA segment encoding influenza virus NP, and optionally a vector for mRNA production comprising a promoter operably linked to a DNA segment encoding influenza virus HA, a vector for mRNA production comprising a promoter operably linked to a DNA segment encoding influenza virus NA, a vector for mRNA production comprising a promoter operably linked to a DNA segment encoding influenza virus M1, a vector for mRNA production comprising a promoter operably linked to a DNA segment encoding influenza virus M2, or a vector for mRNA production comprising a promoter operably linked to a DNA segment encoding influenza virus NS2.

28. A method for preparing an influenza virus B according to any one of items 1 to 6, by contacting a cell with a) a vector for vRNA production comprising a promoter operably linked to an influenza virus PA DNA linked to a transcription termination sequence, a vector for vRNA production comprising a promoter operably linked to an influenza virus PB1 DNA linked to a transcription termination sequence, a vector for vRNA production comprising a promoter operably linked to an influenza virus PB2 DNA linked to a transcription termination sequence, a vector for vRNA production comprising a promoter operably linked to an influenza virus HA DNA linked to a transcription termination sequence, a vector for vRNA production comprising a promoter operably linked to an influenza virus NP DNA linked to a transcription termination sequence, a vector for vRNA production comprising a promoter operably linked to an influenza virus NA DNA linked to a transcription termination sequence, a vector for vRNA production comprising a promoter operably linked to an influenza virus M DNA linked to a transcription termination sequence, and a vector for vRNA production comprising a promoter operably linked to an influenza virus NS cDNA or part thereof linked to a transcription termination sequence, wherein the PB1, PB2, PA, NP, NS, and M DNAs in the vectors for vRNA production encode at least one of: M1 with a serine at position 89, NS2 with glycine at position 76, NS2 with an arginine at position 75, PB2 serine at position 427, and optionally b) a vector for mRNA production comprising a promoter operably linked to a DNA segment encoding influenza virus PA, a vector for mRNA production comprising a promoter operably linked to a DNA segment encoding influenza virus PB1, a vector for mRNA production comprising a promoter operably linked to a DNA segment encoding influenza virus PB2, and a vector for mRNA production comprising a promoter operably linked to a DNA segment encoding influenza virus NP, and optionally a vector for mRNA production comprising a promoter operably linked to a DNA segment encoding influenza virus HA, a vector for mRNA production comprising a promoter operably linked to a DNA segment encoding influenza virus NA, a vector for mRNA production comprising a promoter operably linked to a DNA segment encoding influenza virus M1, a vector for mRNA production comprising a promoter operably linked to a DNA segment encoding influenza virus M2, or a vector for mRNA production comprising a promoter operably linked to a DNA segment encoding influenza virus NS2.

29. A method for preparing an influenza virus B according to any one of items 7 to 11, by contacting a cell with a) a vector for vRNA production comprising a promoter operably linked to an influenza virus PA DNA linked to a transcription termination sequence, a vector for vRNA production comprising a promoter operably linked to an influenza virus PB1 DNA linked to a transcription termination sequence, a vector for vRNA production comprising a promoter operably linked to an influenza virus PB2 DNA linked to a transcription termination sequence, a vector for vRNA production comprising a promoter operably linked to an influenza virus HA DNA linked to a transcription termination sequence, a vector for vRNA production comprising a promoter operably linked to an influenza virus NP DNA linked to a transcription termination sequence, a vector for vRNA production comprising a promoter operably linked to an influenza virus NA DNA linked to a transcription termination sequence, a vector for vRNA production comprising a promoter operably linked to an influenza virus M DNA linked to a transcription termination sequence, and a vector for vRNA production comprising a promoter operably linked to an influenza virus NS cDNA or part thereof linked to a transcription termination sequence, wherein the PB1, PB2, PA, NP, NS, and M DNAs in the vectors for vRNA production encode at least one of: M1 with an arginine at position 93, NS2 with histidine at position 117, PB1 with an asparagine at position 67, b) a vector for mRNA production comprising a promoter operably linked to a DNA segment encoding influenza virus PA, a vector for mRNA production comprising a promoter operably linked to a DNA segment encoding influenza virus PB1, a vector for mRNA production comprising a promoter operably linked to a DNA segment encoding influenza virus PB2, and a vector for mRNA production comprising a promoter operably linked to a DNA segment encoding influenza virus NP, and optionally a vector for mRNA production comprising a promoter operably linked to a DNA segment encoding influenza virus HA, a vector for mRNA production comprising a promoter operably linked to a DNA segment encoding influenza virus NA, a vector for mRNA production comprising a promoter operably linked to a DNA segment encoding influenza virus M1, a vector for mRNA production comprising a promoter operably linked to a DNA segment encoding influenza virus M2, or a vector for mRNA production comprising a promoter operably linked to a DNA segment encoding influenza virus NS2.

30. A method for preparing an influenza virus A according to any one of items 12 to 13, by contacting a cell with a) a vector for vRNA production comprising a promoter operably linked to an influenza virus PA DNA linked to a transcription termination sequence, a vector for vRNA production comprising a promoter operably linked to an influenza virus PB1 DNA linked to a transcription termination sequence, a vector for vRNA production comprising a promoter operably linked to an influenza virus PB2 DNA linked to a transcription termination sequence, a vector for vRNA production comprising a promoter operably linked to an influenza virus HA DNA linked to a transcription termination sequence, a vector for vRNA production comprising a promoter operably linked to an influenza virus NP DNA linked to a transcription termination sequence, a vector for vRNA production comprising a promoter operably linked to an influenza virus NA DNA linked to a transcription termination sequence, a vector for vRNA production comprising a promoter operably linked to an influenza virus M DNA linked to a transcription termination sequence, and a vector for vRNA production comprising a promoter operably linked to an influenza virus NS cDNA linked to a transcription termination sequence, wherein the PB1, PB2, PA, NP, NS, and M DNAs in the vectors for vRNA production encode at least one of: PB1 with a glycine at position 97, PB1 with an asparagine at position 678, PB2 with arginine at position 80, b) a vector for mRNA production comprising a promoter operably linked to a DNA segment encoding influenza virus PA, a vector for mRNA production comprising a promoter operably linked to a DNA segment encoding influenza virus PB1, a vector for mRNA production comprising a promoter operably linked to a DNA segment encoding influenza virus PB2, and a vector for mRNA production comprising a promoter operably linked to a DNA segment encoding influenza virus NP, and optionally a vector for mRNA production comprising a promoter operably linked to a DNA segment encoding influenza virus HA, a vector for mRNA production comprising a promoter operably linked to a DNA segment encoding influenza virus NA, a vector for mRNA production comprising a promoter operably linked to a DNA segment encoding influenza virus M1, a vector for mRNA production comprising a promoter operably linked to a DNA segment encoding influenza virus M2, or a vector for mRNA production comprising a promoter operably linked to a DNA segment encoding influenza virus NS2.

31. A method of making a virus according to any one of items 1 to 19, wherein the method comprises introducing the recombinant vectors according to any one of claims 24 to 26 expressing an influenza virus particle according to any one of claims 1 to 19 in a reverse genetics system.

31. A method of increasing growth rate of influenza viruses wherein said method comprises the step of introducing a modification into the influenza virus PB2, PB1, M and/or NS gene that results in a recombinant influenza virus according to any one of items 1 to 19.

32. The method according to any one of items 27 to 31, wherein the PB1, PB2, PA, NP, NS, and M DNAs in the vectors for vRNA productions have a sequence that corresponds to one that encodes a polypeptide having at least 98% amino acid sequence identity to a corresponding polypeptide encoded by SEQ ID Nos. 2, 4, 6, 8, 10, 12, 14, 16, 20, 24, 26, 28, 30 and 32.

33. A virus obtained by the method according to any one of items 27 to 32.

34. The recombinant influenza according to any of the items 1 to 19 containing Group 1 HA genes.

35. The recombinant influenza according to any of the items 1 to 19 containing Group 2 HA genes.

36. The recombinant influenza according to item 20, used for prime boost immunisations with different Group 1 HA genes.

37. The recombinant influenza according to item 21, used for prime boost immunisations with different Group 2 HA genes.

38. The recombinant influenza according to any of the items 1 to 19, expressing foreign antigens.

The examples described herein are set forth to aid in the understanding of the invention but are not intended to, and should not be construed to limit the scope of the invention in any way. The examples do not include detailed descriptions of conventional methods, e.g., cloning, transfection, and basic aspects of methods for protein expressing in microbial host cells. Such methods are well known to those of ordinary skill in the art.

EXAMPLES

Example 1

Purpose:

To test the growth of the 6:2 B/Thüringen/02/06:B/Murmansk/3/2010 deINS1 point mutants in a growth curve assay to determine mutations which are responsible for the improved virus growth.

Methods

Generation of 6:2 Recombinant Viruses with Specific Amino Acid Changes

In order to create the amino acid changes in the internal genes, point mutations were made in the plasmids containing the gene of interest by subjecting each plasmid to site directed mutagenesis by using QuikChange Lightning site directed mutagenesis kit (Agilent, Santa Clara, CA). 6:2 reassortant viruses were generated by reverse genetics. Six pHW2000 derivatives (plasmids) containing the segments PB2, PB1, PA, NP, M, deltaNS1 derived from B/Thüringen/02/06 (a B/Jiangsu/10/03-like virus from the B Yamagata lineage) as well as a protein expression plasmid coding for Influenza A PR8 NS1 (pCAGGS-NS1 (SAM)) with the pHW2000 derivative plasmid containing the HA and NA genes from B/Murmansk/3/2010 were co-transfected into Vero cells. The transfected cell supernatants were collected 3-8 days post transfection and used to infect Vero cells (CP1) in serum free medium. The CP0 or CP1 stocks were used to infect the growth curves.

Growth Curves:

Vero cells were infected at an MOI of 0.005 with serum free media (Opti-Pro) containing recombinant Trypsin.Input virus was titered and actual MOIs were back calculated for each infection. Time points were collected at 24 h, 48 h, 72 h and 96 h post infection by removing 1 ml media and centrifuging 10 minutes at 2,000×g. Samples were stored at −80 C and titered on the FFA assay at least one time. At least three and up to eight separate growth curves were performed with each sample. Each virus was tested in the growth curve at least three times.

Results

Plasmid Constructs:

PB2: G427S

M: T89S

NS-A: K75R

NS-B: R76G

NS-A/NS-B: K75R and T76G

Virus Rescue:

Rescue 6:2 B/Thüringen/02/06/B/Murmansk/3/2010 delNS with PB2, M and/or NS mutations:

TABLE 1

| Virus | Mutations | | |
|---|---|---|---|
| Lot No. | PB2 | M | NS |
| NF38 | B/Thüringen/02/06 | B/Thüringen/02/06 | B/Thüringen/02/06 |
| NF26 | B/Thüringen/02/06 | T89S | B/Thüringen/02/06 |
| NF86 | B/Thüringen/02/06 | B/Thüringen/02/06 | K75R |
| NF69 | B/Thüringen/02/06 | B/Thüringen/02/06 | R76G |
| NF65 | G427S | T89S | B/Thüringen/02/06 |
| NF88 | G427S | B/Thüringen/02/06 | K75R |
| NF90 | B/Thüringen/02/06 | T89S | K75R |

TABLE 1-continued

| Virus | Mutations | | |
|---|---|---|---|
| Lot No. | PB2 | M | NS |
| NF73 | B/Thüringen/02/06 | T89S | R76G |
| NF67 | B/Thüringen/02/06 | T89S | K75R/R76G |
| NF95 | G427S | T89S | R76G |
| NF40 | G427S | T89S | K75R/R76G |

The rescue supernatant (PO) and the first cell passage on Vero cells (CP1) was titered by FFA.

TABLE 2

| | | CP0 | | CP1 | |
|---|---|---|---|---|---|
| NF | Mutations | Titer | Day Collected | Titer | Day Collected |
| 38 | None | 6.13 | 7 | 6.22 | 6 |
| 26 | M | 5.8 | 8 | 6.24 | 6 |
| 86 | NS-A | 6.48 | 6 | 5.91 | 4 |
| 69 | NS-B | 6.48 | 6 | 6.28 | 4 |
| 65 | PB2/M | 7.3 | 4 | 6.56 | 4 |
| 88 | PB2/NS-A | 6.82 | 6 | 5.67 | 4 |
| 90 | M/NS-A | 6.68 | 6 | 5.8 | 4 |
| 73 | M/NS-B | 6.68 | 6 | 6.91 | 4 |
| 67 | M/NS-A/NS-B | 6.92 | 4 | 6.89 | 4 |
| 95 | PB2/M/NS-B | 6.29 | 6 | 6.55 | 4 |
| 40 | PB2/M/NS-A/NS-B | 7.06 | 4 | 7.3 | 4 |

CP0 = The supernatant from the rescue

CP1 = The first cell passage following the rescue

Control Virus:

The control virus (NF38) is the 6:2 reassortant virus with the 6 internal genes with the original sequence of B/Thüringen/02/06 and the 2 surface genes from B/Murmansk/03/010. The original transfection supernatant (PO) was used in all growth curve infections.

TABLE 3

| Summary of averaged titers: | | | | | | |
|---|---|---|---|---|---|---|
| | 48 h | | 72 h | | 96 h | |
| | Ave | Stdev | Ave | Stdev | Ave | Stdev |
| 38 (B/Thüringen/02/06) P0 | 3.50 | 0.00 | 3.50 | 0.00 | 3.50 | 0.00 |
| 26 (M) | 5.12 | 0.32 | 6.03 | 0.75 | 6.08 | 0.93 |
| 86 (NS-A) | 5.13 | 0.31 | 5.66 | 0.54 | 5.65 | 0.82 |
| 69 (NS-B) | 5.31 | 0.18 | 5.91 | 0.40 | 5.74 | 0.60 |
| 65 (PB2/M) | 5.52 | 0.46 | 5.79 | 0.44 | 5.76 | 0.94 |
| 88 (PB2/NS-A) | 4.65 | 0.54 | 4.75 | 0.50 | 4.92 | 0.57 |
| 90 (M/NS-A) | 4.82 | 0.37 | 5.15 | 0.43 | 5.14 | 0.53 |
| 73 (M/NS-B) | 6.54 | 0.12 | 7.36 | 0.19 | 7.35 | 0.16 |
| 67 (M/NS-A/NS-B) | 6.61 | 0.12 | 7.49 | 0.16 | 7.48 | 0.19 |
| 95 (PB2/M/NS-B) | 7.09 | 0.11 | 7.61 | 0.16 | 7.50 | 0.17 |
| 40 (PB2/M/NS-A/NS-B) | 6.83 | 0.13 | 7.64 | 0.11 | 7.55 | 0.16 |

SUMMARY

Overall, there were high standard deviations for all the viruses except for five: NF73, 67, 95, 40 and the original virus control. All these five viruses contain two mutations in common: M T89S and NS R76G. The standard deviations were low for all three time points tested: 48, 72 and 96 hours post infection. Two of these viruses consistently reached the highest titers: NF95 and 40. NF95 and 40 contain three mutations in common: PB2 G427S, M T89S and NS R76G. There does not appear to be any additional titer increase from the NS mutation K75R. All the viruses that contain the K75R NS mutation only grew poorly and had high standard deviations.

There was high variability in the measured titer for the viruses that had no or few mutations. To test this hypothesis, the PO sample was included in the last three growth curves as a comparator. The input titer was tested and infection was performed at an MOI of 0.005. There was no measurable titer for this virus at any time point tested. This indicates that the B/Thüringen/02/06/B/Murmansk/3/10 deltaNS1 rescued with the original plasmids containing none of the mutations grows extremely poorly, whereas the viruses NF73, 67, 95, 40 that had low standard deviations as mentioned above appear to be stable.

Because the titer of the B/Murmansk delta NS1 virus with the original plasmids was below the limit of detection for all time points tested, we assumed the titers at our limit of detection of 3.5 log. With this assumption, the two viruses with the 3 common mutations (NF40 and 95) produce a titer increase of approximately 4 log. NF40: PB2 G427S, M T89S and NS K75R and R76G produced a titer increase of 4.14 log +/−0.11 at 72 hours post infection and NF 95 (PB2 G427S, M T89S and R76G) has a 4.11 log +/−0.16 titer increase at 72 hours post infection.

Example 2

Purpose:

To test 6:2 B/Thüringen/02/06: B/Phuket/3073/2013 delNS point mutants in a growth curve assay to determine mutations which are responsible for the improved virus growth

Methods

Generation of 6:2 Recombinant Viruses with Specific Amino Acid Changes

In order to create the amino acid changes in the internal genes, point mutations were made in the plasmids containing the gene of interest by subjecting each plasmid to site directed mutagenesis by using QuikChange Lightning site directed mutagenesis kit (Agilent, Santa Clara, CA). 6:2 reassortant viruses were generated by reverse genetics. Six pHW2000 derivatives (plasmids) containing the segments PB2, PB1, PA, NP, M, deltaNS1 derived from B/Thüringen/02/06 (a B/Jiangsu/10/03-like virus from the B Yamagata lineage) as well as a protein expression plasmid coding for Influenza A PR8 NS1 (pCAGGS-NS1 (SAM)) with the pHW2000 derivative plasmid containing the HA and NA genes from B/Phuket/3073/2013 were co-transfected into Vero cells. The transfected cell supernatants were collected 3-8 days post transfection and used to infect Vero cells (CP1) in serum free medium. The CP1 stocks were used to infect the growth curves.

Growth Curves:

Vero cells were infected at an MOI of 0.005 with serum free media (Opti-Pro) containing recombinant Trypsin.Input virus was titered and actual MOIs were back calculated for each infection. Time points were collected at 24 h, 48 h, 72 h and 96 h post infection by removing 1 ml media and centrifuging 10 minutes at 2,000×g. Samples were stored at −80 C and titered on the FFA assay at least one time. At least three and up to eight separate growth curves were performed with each sample. Each virus was tested in the growth curve at least three times.

Results

Plasmid Constructs:

PB1: D67N

M: K93R

NS: Y117H

Virus Rescue:

TABLE 4

Rescue 6:2 B/Thüringen/02/06/B/Phuket/3073/2013 delNS with PB1 and/or PB2 mutations:

| Virus Lot No. | Mutations PB1 | M | NS |
|---|---|---|---|
| NF41 | B/Thüringen/02/06 | B/Thüringen/02/06 | B/Thüringen/02/06 |
| NF32 | D67N | B/Thüringen/02/06 | B/Thüringen/02/06 |
| NF33 | B/Thüringen/02/06 | K93R | B/Thüringen/02/06 |
| NF64 | D67N | K93R | B/Thüringen/02/06 |
| NF77 | D67N | B/Thüringen/02/06 | Y117H |
| NF63 | B/Thüringen/02/06 | K93R | Y117H |
| NF43 | D67N | K93R | Y117H |

The rescue supernatant (PO) and the first cell passage on Vero cells (CP1) was titered by FFA.

TABLE 5

| NF | Mutations | CP0 | CP1 |
|---|---|---|---|
| 41 | None | 6.22 | 5.86 |
| 32 | PB1 | 6.40 | 6.12 |
| 33 | M | 6.70 | 6.45 |
| 64 | PB1/M | 7.79 | 6.98 |
| 77 | PB1/NS | ND | 7.02 |
| 63 | M/NS | 7.44 | 6.94 |
| 43 | PB1/M/NS | 7.43 | 7.43 |

ND = not determined

Control Virus:

The control virus is the 6:2 reassortant virus with the 6 internal genes with the original sequence of B/Thüringen/02/06 and the 2 surface genes from B/Phuket/3073/2013. The original transfection supernatant (PO) was passaged one time on serum free Vero cells and the CP1 was used in all growth curve infections.

BD=Below Detection Limit (3.5 log 10 FFU/ml)

ND=Not Determined

TABLE 6

Average of growth curve titers:

| Virus Lot | Mutations PB1 | M | NS | Average log10FFU/ml 24 h | 48 h | 72 h | 96 h | STDEV 24 h | 48 h | 72 h | 96 h |
|---|---|---|---|---|---|---|---|---|---|---|---|
| NF41 | B/Thüringen/02/06 | B/Thüringen/02/06 | B/Thüringen/02/06 | BD | 5.63 | 7.06 | 7.42 | | 0.09 | 0.18 | 0.15 |

TABLE 6-continued

| Average of growth curve titers: | | | | | | | | | | | |
|---|---|---|---|---|---|---|---|---|---|---|---|
| Virus | Mutations | | | Average log10FFU/ml | | | | STDEV | | | |
| Lot | PB1 | M | NS | 24 h | 48 h | 72 h | 96 h | 24 h | 48 h | 72 h | 96 h |
| NF32 | D67N | B/ Thüringen/ 02/06 | B/ Thüringen/ 02/06 | BD | 6.00 | 6.97 | 7.19 | | 0.26 | 0.26 | 0.21 |
| NF33 | B/ Thüringen/ 02/06 | K93R | B/ Thüringen/ 02/06 | BD | 6.38 | 7.12 | 7.37 | | 0.21 | 0.23 | 0.20 |
| NF42 | B/ Thüringen/ 02/06 | B/ Thüringen/ 02/06 | Y117H | BD | 6.55 | 7.30 | 7.23 | | 0.11 | 0.17 | 0.17 |
| NF64 | D67N | K93R | B/ Thüringen/ 02/06 | BD | 7.24 | 7.65 | 7.61 | | 0.06 | 0.23 | 0.13 |
| NF77 | D67N | B/ Thüringen/ 02/06 | Y117H | BD | 6.85 | 7.65 | 7.46 | | 0.28 | 0.15 | 0.20 |
| NF63 | B/ Thüringen/ 02/06 | K93R | Y117H | BD | 7.50 | 7.76 | 7.59 | | 0.06 | 0.09 | 0.11 |
| NF43 | D67N | K93R | Y117H | 4.81 | 8.01 | 8.14 | 8.02 | 0.73 | 0.14 | 0.09 | 0.10 |

SUMMARY

All growth curves consistently defined 3 distinct populations. NF 43 always grew to highest titer and in the all assays, NF43 surpassed 8.0 log FFU/ml. NF41 has the original plasmids as described above and grew to the lowest titers. The single mutations NF32 (PB1) and NF33 (M) were similar in growth properties to the original plasmids. The viruses with the 2 mutant mixtures NF64 (PB1/M), NF77 (PB1/NS) and NF64 (M/NS), grew to a significantly higher titer than the single mutants but were not as high as NF43 which contains all 3 mutations.

The combination of the all three PB1, M and NS mutations lead to an increase in virus growth. At the peak titers the three mutations increase the titer by approximately 0.8-1.14 log.

Example 3

Purpose:

To test the growth of the 6:2 A/IVR-116:A/Hong Kong/4801/2014 deINS1 point mutants in a growth curve assay to determine mutations which are responsible for the improved virus growth.

Methods

Generation of 6:2 Recombinant Viruses with Specific Amino Acid Changes

In order to create the amino acid changes in the internal genes, point mutations were made in the plasmids containing the gene of interest by subjecting each plasmid to site directed mutagenesis by using QuikChange Lightning site directed mutagenesis kit (Agilent, Santa Clara, CA). 6:2 reassortant viruses were generated by reverse genetics. Six pHW2000 derivatives (plasmids) containing the segments PB2, PB1, PA, NP, M, deltaNS1 derived from A/IVR-116 (a lab strain A virus that contains PB2, PA, NP, M and NS genes from A/Puerto Rico/08/1934 and PB1 from A/Texas/1/1977) as well as a protein expression plasmid coding for Influenza A PR8 NS1 (pCAGGS-NS1 (SAM)) with the pHW2000 derivative plasmid containing the HA and NA genes from A/Hong Kong/4801/2014 were co-transfected into Vero cells. The transfected cell supernatants were collected 3-4 days post transfection and used to infect Vero cells (CP1) in serum free medium. The CP1 stocks were used to infect the growth curves.

Growth Curves:

Vero cells were infected at an MOI of 0.005 with serum free media (Opti-Pro) containing recombinant Trypsin.Input virus was titered and actual MOIs were back calculated for each infection. Time points were collected at 24 h, 48 h and 72 h post infection by removing 1 ml media and centrifuging 10 minutes at 2,000×g. Samples were stored at −80 C and titered on the FFA assay at least one time. At least three and up to eight separate growth curves were performed with each sample. Each virus was tested in the growth curve at least three times.

Results

Plasmid Constructs:

PB2: K80R

PB1-1: E97G

PB1-2: S678N

PB1-3: E97G and S678N

Virus Rescue:

TABLE 7

| Rescue 6:2 AGHB: A/Hong Kong/4801/2014 deINS with PB1 and/or PB2 mutations: | | |
|---|---|---|
| | Mutations | |
| Virus Lot No. | PB2 | PB1 |
| NF6 | IVR-116 | A314G |
| NF7 | IVR-116 | G2057A |
| NF8 | IVR-116 | A314G/G2057A |
| NF9 | IVR-116 | IVR-116 |
| NF10 | A266G | A314G |
| NF11 | A266G | G2057A |
| NF12 | A266G | A314G/G2057A |
| NF13 | A266G | IVR-116 |

TABLE 8

| The rescue supernatant (P0) and the first cell passage on Vero cells (CP1) was titered by FFA. | | | | |
|---|---|---|---|---|
| NF | PB1 | PB2 | CP0 | CP1 |
| 6 | PB1-1 | IVR-116 | 6.72 | 6.88 |
| 7 | PB1-2 | IVR-116 | 7.33 | 7.45 |
| 8 | PB1-1/ PB1-2 | IVR-116 | 7.33 | 7.43 |
| 9 | IVR-116 | IVR-116 | 6.70 | 6.66 |
| 10 | PB1-1 | PB2-1 | 7.11 | 7.1 |
| 11 | PB1-2 | PB2-1 | 7.31 | 7.47 |
| 12 | PB1-1/ PB1-2 | PB2-1 | 6.88 | 7.66 |
| 13 | IVR-116 | PB2-1 | 7.00 | 7.14 |

Control Virus:

The control virus is the 6:2 reassortant virus with the 6 internal genes with the original sequence of IVR-116 and the 2 surface genes from A/Hong Kong/4801/2014. The original transfection supernatant (PO) was passaged one time on serum free Vero cells and the CP1 was used in all growth curve infections.

TABLE 9

| Average of three growth curve titers: | | | | | | | | |
|---|---|---|---|---|---|---|---|---|
| Virus | Mutations | | Average log10FFU/ml | | | STDEV | | |
| Lot | PB2 | PB1 | 24 h | 48 h | 72 h | 24 | 48 | 72 |
| NF6 | IVR-116 | A314G | 5.68 | 7.24 | 7.27 | 0.32 | 0.07 | 0.10 |
| NF7 | IVR-116 | G2057A | 6.61 | 7.72 | 7.74 | 0.57 | 0.04 | 0.06 |
| NF8 | IVR-116 | A314G/ G2057A | 7.03 | 7.93 | 7.89 | 0.39 | 0.00 | 0.09 |
| NF9 | IVR-116 | IVR-116 | 5.79 | 7.20 | 7.19 | 0.49 | 0.07 | 0.09 |
| NF10 | A266G | A314G | 6.06 | 7.30 | 7.31 | 0.38 | 0.08 | 0.10 |
| NF11 | A266G | G2057A | 6.80 | 7.71 | 7.77 | 0.57 | 0.03 | 0.08 |
| NF12 | A266G | A314G/ G2057A | 6.89 | 7.89 | 7.78 | 0.47 | 0.16 | 0.12 |
| NF13 | A266G | IVR-116 | 6.00 | 7.33 | 7.33 | 0.65 | 0.06 | 0.05 |

SUMMARY

All three growth curves consistently defined 4 distinct populations. NF 8 and 12 always grew to highest titer and in the third assay surpassed 8.0 log FFU/ml at 48 hours post infection. NF8 and NF12 have the 2 PB1 mutations and 12 has the additional PB2 mutation. NF11 has the additional PB2 mutation. The next group is NF10 and NF13 which both have the PB2 mutation. NF10 has the additional A314G mutation while NF13 has the original PB1 plasmid. The last and lowest group is NF9 and NF6. NF9 has the original PB2 and PB1 plasmids while NF6 has the PB1 A314G plasmid.

The combination of the two PB1 mutations is responsible for a significant increase in virus growth.

Materials and Methods

Master Donor Virus with Same Internal Genes, Internal Gene Sequencing:

RNA Extraction:

RNA was extracted using QIAamp Viral Mini kit from Qiagen. RNA was eluted in 60 ul buffer AVE and stored at −80 C.

RT-PCR:

RT-PCR was performed using either SuperScript III One-Step RT-PCR kit (Thermo Fisher Scientific) or QIAGEN OneStep RT-PCR Kit (Qiagen). Superscript reactions were set up as follows: 25 uL 2× SuperScript III buffer, 1 uL enzyme mix, 19 uL RNAse-free water, 1 uL Forward Primer (10 uM), 1 uL Reverse primer (10 uM) and 3 uL RNA. The thermocycler conditions were as follows: 45° C. for 30 minutes, 94° C. for 2 minutes and 40 cycles of 94° C. for 15 seconds, 55° C. for 30 seconds and 68° C. for 2 minutes. There was a 10 minutes extension time at 68° C. See tables 1 and 2 for RT-PCR Primer combinations and sequences.

Qiagen OneStep RT-PCR reactions were set up as follows: 10 uL 5× QIAGEN OneStep RT-PCR Buffer, 2 uL dNTP Mix, 2 uL enzyme mix, 2 uL Forward Primer (10 uM), 2 uL Reverse Primer (10 uM), 29 uL RNA-free water and 3 uL RNA. The thermocycler conditions were as follows: 50° C. for 30 minutes, 95° C. for 15 minutes and 40 cycles of 94° C. for 30 seconds, 55° C. 30 seconds and 72° C. for 2 minutes. There was a 10 minute extension at 72° C. See tables 1 and 2 for RT-PCR Primer combinations and sequences.

Gel Purification:

RT-PCR samples were run on a 0.8-1% Agarose gel and the correct size band was cut out and purified using QIAquick Gel Extraction Kit (Qiagen). DNA was eluted in DNase/RNase free water and diluted to 4-10 ng/ul for sequencing.

Sequencing:

All sequencing reactions were performed by Genewiz. Sequencing samples were prepared by mixing 10 ul of 4-10 ng/ul DNA with 5 uL of the sequencing primer (5 uM). Sequencing chromatograms were analyzed by Vector NTI (Thermo Fisher Scientific). See tables 3 and 4 for sequencing primers.

Subcloning HA and NA into pHW2006 Vector:

RNA Extraction:

RNA was extracted using QIAamp Viral Mini kit from Qiagen. RNA was eluted in 60 ul buffer AVE and stored at −80 C.

RT-PCR:

RT-PCR was performed using either SuperScript III One-Step RT-PCR kit (Thermo Fisher Scientific) or QIAGEN OneStep RT-PCR Kit (Qiagen). Superscript reactions were set up as follows: 25 uL 2× SuperScript III buffer, 1 uL enzyme mix, 19 uL RNAse-free water, 1 uL Forward Primer (10 uM), 1 uL Reverse primer (10 uM) and 3 uL RNA. The thermocycler conditions were as follows: 45° C. for 30 minutes, 94° C. for 2 minutes and 40 cycles of 94° C. for 15 seconds, 55° C. for 30 seconds and 68° C. for 2 minutes. There was a 10 minute extension time at 68° C. See table 5 for RT-PCR primers.

Gel Purification:

RT-PCR samples were run on a 0.8-1% Agarose gel and the correct size band was cut out and purified using QIAquick Gel Extraction Kit (Qiagen). DNA was eluted in DNase/RNase free water. The purified DNA was restriction digested with BsmBI (NEB) at 55 C for 2 hours. QIAquick Nucleotide Removal Kit was used to purify the digested DNA. The DNA was eluted in DNA/RNAase free water. 2 ug of pHW2006 vector was also digested with BsmBI and purified in the same manner. 180 ng HA and 140 ng NA DNA was ligated with 1 ug pHW2006 DNA using Accupower Ligation PreMix (Bioneer) for 15 minutes at room temperature. DH5a Max Efficiency Competent cells (Thermofisher Scientific) were transformed with 2 uL ligation mix and grown on LB/Ampicillin plates overnight. Isolated colonies were screened for the correct insert using Accustart II PCR SuperMix (Quanta Bio) and vector specific primers (P3pHW: CCCACTGCTTACTGGCTTAT (SEQ ID No. 21) and P5pHW: CAGATGGCTGGC AACTAGAA) (SEQ ID No. 22). Three clones with the correct sized band were grown overnight in LB media with ampicillin and DNA was purified using QIAprep Spin Miniprep Kit. Miniprep DNA was diluted to 80 ng/ul using DNA/RNAase free water.

Sequencing:

All sequencing reactions were performed by Genewiz. Sequencing samples were prepared by mixing 10 ul of 80 ng/ul DNA with 5 uL of the sequencing primer (5 uM). Sequencing chromatograms were analyzed by Vector NTI (Thermo Fisher Scientific). See table 6 for sequencing primers.

RACE (Rapid Amplification of cDNA Ends):

RNA Extraction:

RNA was extracted using QIAamp Viral Mini kit from Qiagen. RNA was eluted in 60 ul buffer AVE and stored at −80 C.

Polyadenylation of vRNA

Polyadenylation was performed using Poly(A) Tailing Kit (Ambion). Briefly, the vRNA was used in a 40 ul reaction with 8 ul 5× E-PAP buffer, 4 ul 25 mM $MnCl_2$, 2 ul 10 mM ATP, 1 ul RNAsin Plus (Promega), 1 ul E-PAP (polymerase) and 22 ul vRNA. The reaction was incubated at 37° C. for 1 hour.

cDNA Synthesis

Polyadenylated vRNA was used in the cDNA synthesis using Superscript II Reverse Transcriptase (Thermo Fisher Scientific). The 20 ul reverse transcriptase reaction was assembled as follows: 2 uL 5×FS Buffer, 1 ul TRSA Oligo (CGCAGTCGGTACTTTTTTTTTTTTTTTTTTTVN, SEQ ID NO. 17), 1 ul TS oligo (AAGCAGTGGTATCAACGCAGAGTACGCrGrGrG, SEQ ID No. 18), 1 ul 10 mM dNTPs, 2 ul 0.1M DTT, 1 ul RNAsin Plus (Promega), 1 uL Superscript II enzyme and 9 ul polyadenylated vRNA. The reaction was incubated at 42° C. for 1 hour. After 1 hour incubation, 2 ul 20 mM $MgCl_2$ was added and incubated at 42° C. for 15 additional minutes. These samples were stored at −20° C. Dissolve oligos TRSA and TS in RNase-free TE pH 7.0:water=1:1 at a concentration of 10 uM, store at −20° C. Dissolve TS Oligos and influenza virus specific oligos at 10 uM in TE pH 8.0 or RNAase/DNAase Free water. See table 7 for RACE primer sequences.

5' and 3' RACE

PCR was used to amplify the non-coding regions (NCRs) using pfu Turbo Polymerase (Agilent) and Go Taq G2 Polymerase (Promega). The 25 ul PCR reactions were assembled by adding: 2.5 ul Pfu 10× Reaction Buffer, 2.5 uL 2 mM dNTPs, 0.5 ul sense primer (see tables 8 and 9), 0.5 ul antisense primer (see tables 8 and 9), 17.5 ul RNAse/DNAse free water, 0.3 uL Pfu Turbo Polymerase (2.5 U/ul, Agilent) and 0.2 uL Go Taq G2 Polymerase (5 U/ul, Promega) and 1 ul cDNA. Samples were amplified as follows: 95° C. 30 seconds and 40 cycles of 95° C. 30 seconds, 59 or 60° C. (see tables 10-11) 1 minute, 68° C. 1 minute, followed by a 2 minutes elongation step at 68° C. PCR products were evaluated on a 1.0% Agarose gel in 1×TAE and were gel purified using QIAquick Gel Extraction Kit (Qiagen). DNA was eluted in DNase/RNase free water and diluted to 4-10 ng/ul for sequencing with gene specific primers.

Sequencing:

All sequencing reactions were performed by Genewiz. Sequencing samples were prepared by mixing 10 ul of 4-10 ng/ul DNA with 5 uL of the sequencing primer (5 uM). Sequencing chromatograms were analyzed by Vector NTI (Thermo Fisher Scientific).

T4 RNA Ligase Method for Sequencing the 3' and 5' Non Coding Region:

RNA extraction:

RNA was extracted using QIAamp Viral Mini kit from Qiagen. RNA was eluted in 60 ul buffer AVE and stored at −80 C.

Denature RNA:

In a 16.5 ul reaction, 13 ul vRNA, 0.5 ul RNAsin Plus (Promega) and 3 ul 10 T4 RNA ligase buffer (New England Biolabs) were combined and incubated at 65 C for 5 minutes. Transfer to ice immediately.

vRNA Ligation:

To the 16.5 ul denatured vRNA following was added: 4 ul T4 RNA ligase (10 U/ul, New England Biolabs) 0.5 ul RNAsin Plus (Promega), 6 ul 50% PEG 8000 and 3 ul 10 uM ATP. The 30 ul reaction was incubated at 37° C. for 1 hour followed by a 10 minute 65° C. inactivation, store at −80° C.

RT-PCR

RT-PCR using the Superscript III RT-PCR One-step RT-PCR System (Thermo Fisher Scientific). The T4 RNA ligation primers and a gene specific primer were used (see tables 12-13) for each reaction. Set up the 25 ul reactions was as follows: 12.5 ul 2× Reaction Mix, 1 ul RNAsin (Promega), 1 ul 10 uM Sense primer, 1 ul 10 uM antisense primer, 2 ul Superscript III RT/Platinum Taq Mix and 7.5 ul ligated vRNA (from previous step). Samples were amplified as follows: 45° C. 60 minutes, 94 C 2 minutes and 40 cycles of 94° C. 15 seconds, 50 to 60° C. 30 seconds, 68° C. 1 minute, followed by a 10 minutes elongation step at 68° C. PCR products were evaluated on a 1.0% Agarose gel in 1×TAE and were gel purified using QIAquick Gel Extraction Kit (Qiagen). DNA was eluted in DNase/RNase free water and diluted to 4-10 ng/ul for sequencing with gene specific primers.

TABLE 10

Overview on SEQ IDs of the modified sequences described herein:

| | | nt sequence | aa sequence |
|---|---|---|---|
| B/Murmansk/3/10-PB2 | Wt sequence | SEQ ID No. 1 | SEQ ID No. 2 |
| G427S | Mutant sequence | SEQ ID No. 3 | SEQ ID No. 4 |
| M1 | Wt sequence | SEQ ID No. 5 | SEQ ID No. 6 |
| T89S | Mutant sequence | SEQ ID No. 7 | SEQ ID No. 8 |
| NS2 | Wt sequence | SEQ ID No. 9 | SEQ ID No. 10 |
| K75R R76G | Mutant Sequence | SEQ ID No. 11 | SEQ ID No. 12 |
| NS2 R76G | Mutant Sequence | SEQ ID No. 33 | SEQ ID No. 34 |
| B/Phuket/3073/14 PB1 | Wt sequence | SEQ ID No. 13 | SEQ ID No. 14 |
| D67N | Mutant sequence | SEQ ID No. 15 | SEQ ID No. 16 |
| M1 | Wt sequence | SEQ ID No. 5 | SEQ ID No. 6 |
| K93R | Mutant sequence | SEQ ID No. 19 | SEQ ID No. 20 |
| NS | Wt sequence | SEQ ID No. 9 | SEQ ID No. 10 |
| Y117H | Mutant sequence | SEQ ID No. 23 | SEQ ID No. 24 |
| A/HK/4801/14/delNS PB2 | Wt sequence | SEQ ID No. 25 | SEQ ID No. 26 |
| K80R | Mutant sequence | SEQ ID No. 27 | SEQ ID No. 28 |
| PB1 | Wt sequence | SEQ ID No. 29 | SEQ ID No. 30 |
| E97G S678N | Mutant sequence | SEQ ID No. 31 | SEQ ID No. 32 |
| E97G | Mutant sequence | SEQ ID No. 35 | SEQ ID No. 37 |
| S678N | Mutant sequence | SEQ ID No. 36 | SEQ ID No. 38 |

Example 4

Growth of Influenza B deltaFLU Strains Containing the HA and NA Recommended for the Seasons 2018-2020 with (YAM) and without (Original) Internal Gene Mutations.

6:2 transfectant reassortant viruses containing mutations in the internal gene segments from B/Thüringen lacking NS1 and the surface proteins from strains recommended by the WHO for the seasons 2018-2020 were obtained by reverse genetics. YAM designates viruses containing the following internal mutations: PB1: D67N, M: K93R, NS1: Y117H. Vero cells were infected at an MOI of 0.005 with passage 1 of indicated rescued delNS1 viruses. Samples were collected at 48, 72 and 96 hours post infection and titered by fluorescent focus assay (FFA).

TABLE 11

| | 48 hrs | 72 hrs | 96 hrs |
|---|---|---|---|
| B/Colorado/06/2017 del NS1 Original | 5.03 | 4.98 | 5.02 |
| B/Colorado/06/2017 del NS1 YAM | 8.22 | 8.31 | 8.28 |
| B/Maryland/15/2016 del NS1 YAM | 8.26 | 8.23 | 8.23 |
| B/Iowa/06/2017 del NS1 YAM | 7.63 | 7.91 | 7.85 |
| B/Phuket/3073/2013 del NS1 YAM | 8.10 | 8.16 | 8.22 |

The invention claimed is:

1. A recombinant influenza B virus with increased growth rate in Vero cells as compared to wild type influenza virus comprising SEQ ID NOs: 2, 6 and 10, and lacking a functional NS1 protein (delNS1 influenza), comprising:

an M gene segment resulting in an M1 protein comprising amino acid sequence SEQ ID NO:8; and an NS gene segment comprising one or more nucleotide modifications resulting in an NS2 protein comprising one of amino acid sequences SEQ ID NO:12 or 34, and optionally a PB2 gene segment resulting in a PB2 protein comprising amino acid sequence SEQ ID NO:4.

2. The recombinant influenza virus according to claim 1, wherein said virus is a reassortant virus, is attenuated or replication deficient, and/or comprises one or more modifications within the HA and/or NA genes as compared to wild type influenza virus comprising SEQ ID NOs: 2, 6 and 10.

3. The recombinant influenza virus according to claim 1, comprising a modified NS1 gene segment which codes for an NS1 protein lacking a functional RNA binding domain and/or a functional carboxy terminal domain or a combination thereof.

4. The recombinant influenza virus according to claim 1, wherein the virus comprises one or more modifications within HA and/or NA genes as compared to wild type influenza virus comprising SEQ ID NOs: 2, 6 and 10.

5. The recombinant influenza virus according to claim 1, further comprising a pharmaceutically acceptable carrier.

6. A method of treating an influenza virus infection, comprising the step of administering an immunogenically effective amount of a vaccine comprising the virus of claim 1.

7. A method of making a virus, wherein the method comprises introducing one or more recombinant vectors comprising the M gene segment, the PB2 gene segment and/or the NS gene segment of claim 1 into a reverse genetics system and expressing an influenza virus particle.

8. The recombinant influenza virus according to claim 1, wherein the virus comprises Group 1 HA or Group 2 HA genes.

9. The recombinant influenza virus according to claim 1, wherein the virus expresses foreign antigens.

10. The recombinant influenza virus according to claim 1, comprising a PB1 gene segment having one or more nucleotide modifications that result in a PB1 protein having an amino acid substitution selected from the group consisting of an asparagine at position 67 according to the numbering of SEQ ID NO:14 and an asparagine at position 678 according to the numbering of SEQ ID NO:30.

11. The recombinant influenza virus according to claim 1, wherein the NS2 protein comprises SEQ ID NO:12.

12. The recombinant influenza virus according to claim 1, wherein the NS2 protein comprises SEQ ID NO:34.

13. The recombinant influenza virus according to claim 1, wherein the PB2 protein comprises SEQ ID NO:4.

14. The method of making a virus according to claim 7 comprising the steps of contacting a cell with a vector for vRNA production comprising a promoter operably linked to an influenza virus PA DNA linked to a transcription termination sequence, a vector for vRNA production comprising a promoter operably linked to an influenza virus PB1 DNA linked to a transcription termination sequence, a vector for vRNA production comprising a promoter operably linked to an influenza virus PB2 DNA linked to a transcription termination sequence, a vector for vRNA production comprising a promoter operably linked to an influenza virus HA DNA linked to a transcription termination sequence, a vector for vRNA production comprising a promoter operably linked to an influenza virus NP DNA linked to a transcription termination sequence, a vector for vRNA production comprising a promoter operably linked to an influenza virus NA DNA linked to a transcription termination sequence, a vector for vRNA production comprising a promoter operably linked to an influenza virus M DNA linked to a transcription termination sequence, and a vector for vRNA production comprising a promoter operably linked to an influenza virus NS cDNA or part thereof linked to a transcription termination sequence, wherein the PB1, PB2, PA, NP, NS, and M DNAs in the vectors for vRNA production encode M1 with a serine at position 89, and at least one of:

NS2 with glycine at position 76 and arginine at position 75, and PB2 with serine at position 427.

* * * * *